(12) United States Patent
Johnston

(10) Patent No.: US 8,796,414 B2
(45) Date of Patent: Aug. 5, 2014

(54) IDENTIFICATION AND USE OF NOVOPEPTIDES FOR THE TREATMENT OF CANCER

(76) Inventor: Stephen A. Johnston, Tempe, AZ (US)

( * ) Notice: Subject to any disclaimer, the term of this patent is extended or adjusted under 35 U.S.C. 154(b) by 205 days.

(21) Appl. No.: 13/052,490

(22) Filed: Mar. 21, 2011

(65) Prior Publication Data

US 2013/0072660 A1     Mar. 21, 2013

Related U.S. Application Data

(62) Division of application No. 12/280,389, filed as application No. PCT/US2007/062920 on Feb. 27, 2007, now abandoned.

(60) Provisional application No. 60/777,534, filed on Feb. 27, 2006.

(51) Int. Cl.
*A61K 38/00*     (2006.01)

(52) U.S. Cl.
USPC .......................................... 530/300; 530/324

(58) Field of Classification Search
None
See application file for complete search history.

(56) References Cited

U.S. PATENT DOCUMENTS

| | | | | |
|---|---|---|---|---|
| 5,840,839 | A * | 11/1998 | Wang et al. | 530/325 |
| 8,053,552 | B2 * | 11/2011 | Von Knebel-Doeberitz et al. | 530/300 |
| 2004/0265803 | A1 * | 12/2004 | Doeberitz et al. | 435/6 |
| 2010/0111993 | A1 * | 5/2010 | Tureci et al. | 424/192.1 |

FOREIGN PATENT DOCUMENTS

WO     WO 03/084467     * 10/2003

OTHER PUBLICATIONS

Englehard (1994) Annu. Rev. Immunol. 12: 181.*
Rammenesee et al. (1993) Annu. Rev. Immunol. 11: 213.*

* cited by examiner

*Primary Examiner* — Mark Halvorson

(57) ABSTRACT

Disclosed are compositions relating to novopeptides identified by the presence of frameshift mutations in tumor genes previously not identified as being oncogenic. The disclosed peptides can be used in the disclosed methods for the treatment of cancer.

2 Claims, 12 Drawing Sheets

Figure 1A:
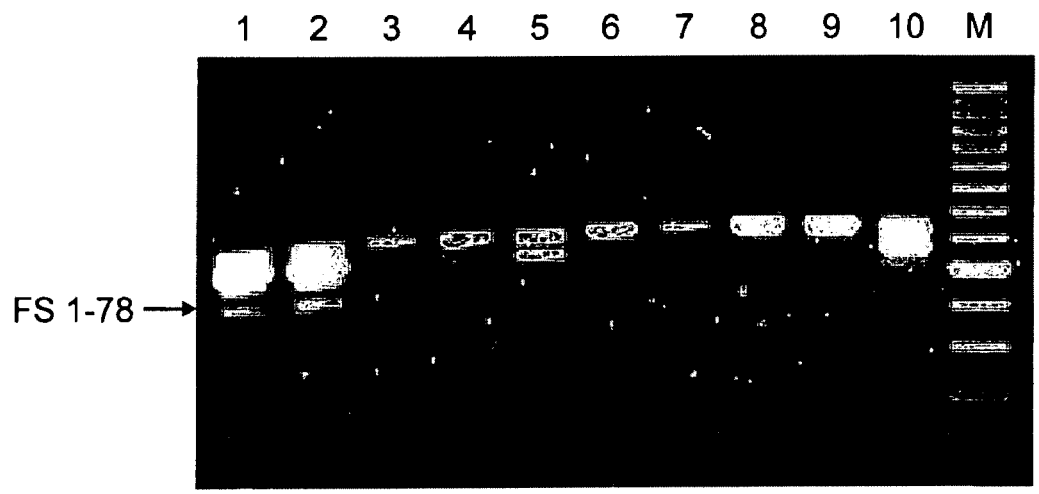

1. PCR FS seq between Promoter and Terminator

2. Assembly by PCR

3. PCR Splicing by Overlap Exptension

B16 mouse tumor cells
stained with anti-6-21 sera

Pre-immune sera on
B16 mouse tumor cells

4T1 mouse breast tumor
cells stained with anti-621

US 8,796,414 B2

IDENTIFICATION AND USE OF NOVOPEPTIDES FOR THE TREATMENT OF CANCER

This application is a division of U.S. non-provisional application Ser. No. 12/280,389, filed Jan. 15, 2009, which is a U.S. national phase application of PCT international application No. PCT/US2007/062920 filed Feb. 27, 2007, which claims the benefit of U.S. Provisional Application No. 60/777,534, filed on Feb. 27, 2006; this application claims the benefit of each of the foregoing and each is incorporated herein by reference in its entirety. The instant application contains a sequence listing which has been submitted in ASCII format via EFS-Web and is hereby incorporated by reference in its entirety. Said ASCII copy, created on Nov. 2, 2012, is named 04995400.txt and is 85,029 bytes in size.

I. BACKGROUND

It is estimated that in 2004 more than 2.4 million new cancer cases will be diagnosed in the U.S. and more than 1 million are expected to be skin cancers. Of those individuals with skin cancer, ~96,000 will be diagnosed with melanoma (4% of newly diagnosed cancers), the most deadly form of skin cancer. Furthermore, the incidence of melanoma continues to increase faster than any other cancer. The stochastic nature of 90 to 95% of all cancers means that everyone is at risk of developing a cancer. In the United States, men have a 50% lifetime risk of developing cancer, while women have a 33% chance (ACS, 2004). With an annual mortality rate of ~563,700 per year, cancer is the second leading cause of death in the U.S.

Vaccination against cancer has been proposed for treatment, and occasionally prevention, of cancer, and considerable research effort has been devoted to the exploration of a variety of cancer vaccination strategies. The goal of finding vaccine compositions and treatment methods that are capable of reliably and predictably overcoming tolerance and setting in motion an immune response against tumor cells without inducing autoimmunity has, until now, proved elusive. It is nevertheless clear that cancerous cells express proteins that can be recognized by the immune system, as demonstrated by experiments in which mice vaccinated with various kinds of tumor cell preparations show protection from tumor challenge. Antigens that are expressed in or by tumor cells are referred to as "tumor associated antigens" ("TAA's"). A particular TAA may or may not also be expressed in non-cancerous cells; TAA's that are not expressed or rarely expressed in non-cancerous cells, or whose expression in non-cancerous cells is sufficiently reduced in comparison to that in cancerous cells that an immune response induced upon vaccination is reasonably specific to cancerous cells, are referred to as "tumor specific antigens" ("TSA's").

Over the past two decades, many labs have devised numerous techniques which aim to turn the patient's immune system against a pre-existing tumor (Berzofsky et al., 2004). These include the use of whole cells, peptides, genetically modified tumor cells, heat-shock proteins or apoptotic tumor cells to stimulate the host's immune system to respond to antigens that are characteristic of cancer cells. Arguably the most elegant approach to cancer vaccination is to use vaccine formulations composed of known and defined TAA's, since this will maximize specificity. Functionally, TAA's may be classed as self and non-self. Self TAA's are derived from nonmutated genes whose expression is limited to selected normal tissues or to overexpressed proteins. While most TAA's identified to date belong to this self class, there are two large potential problems associated with such antigens: autoimmunity and tolerance. Non-self TAA's are expressed exclusively by cancer cells, and can be thought of as tumor-specific antigens (TSA's). TSA's can originate either exogenously (such as those derived from viral proteins in virally-associated tumors) or endogenously. Mutation-derived TSA's can arise from point mutations, translocations, and exon mis-splicing. Unlike self TAA's, TSA's do not pose the risk of autoimmunity and tolerance.

I. SUMMARY

Disclosed are methods for identifying and immunologically screening candidate antigens for inclusion in a prophylactic and/or therapeutic cancer vaccine. Further disclosed is a general class of antigens, referred to herein as novopeptides, as well as two specific subsets thereof, non-MS novopeptides and FS-novopeptides. Disclosed are methods and compositions related to novopeptides, unique nonsense proteins specific to a tumor, for use in diagnosing, preventing and treating cancer. Also disclosed is a method of using novopeptides to induce an immune response against cancer. Disclosed are vaccines having one or more novopeptide components, which are used prophylactically, or as a therapeutic treatment against existing cancerous cells.

III. BRIEF DESCRIPTION OF THE DRAWINGS

The accompanying drawings, which are incorporated in and constitute a part of this specification, illustrate several embodiments and together with the description illustrate the disclosed compositions and methods.

Figure 1B:

FIG. 1 demonstrates a method of determining frameshift frequency in tumor cells using a mouse melanoma model B1 6F10. FIG. 1a: cDNA was generated RNA from cultured cells. It was sequenced directly by RT-PCR sequencing. FIG. 1b: In vivo confirmation of in vitro-derived FS mutations. To confirm that the FS was expressed in vivo, RNA was extracted from B16 lung metastases after injection of cells systemically. cDNA was generated and the FS confirmed by RT-PCR sequencing.

FIGS. 2a and 2b show PCR amplification of FS1-78 and FS6-21, respectively. Arrow indicates FS band; other bands are wild type alleles. Lane 1: B16/F1 tumor cells; Lane 2: B16/F10 tumor cells; Lane 3: normal heart; Lane 4: normal intestine; Lane 5: normal kidney; Lane 6: normal liver; Lane 7: normal lung; Lane 8: normal skeletal muscle; Lane 9: normal skin; Lane 10: normal spleen; Lane M: Molecular weight marker.

Figure 3:
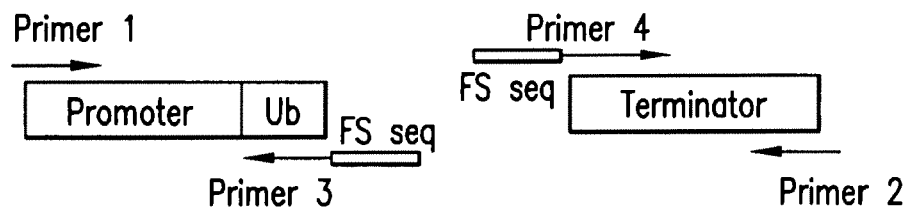
Figure 3:
Figure 3:
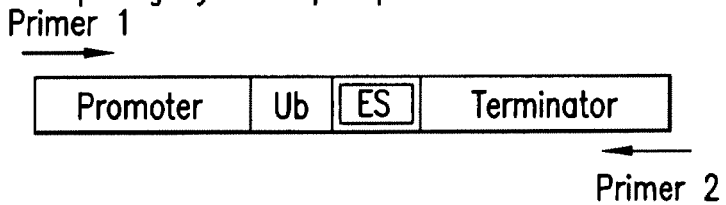

FIG. 3 shows the linear expression element construction (LEE). Each LEE is comprised of a fragment that contains a mammalian promoter (blue), the ubiquitin gene for better intracellular processing (yellow), a fragment that contains transcriptional and translational terminators (red). The two fragments are linked via the frameshift sequence (green).

Figure 4:
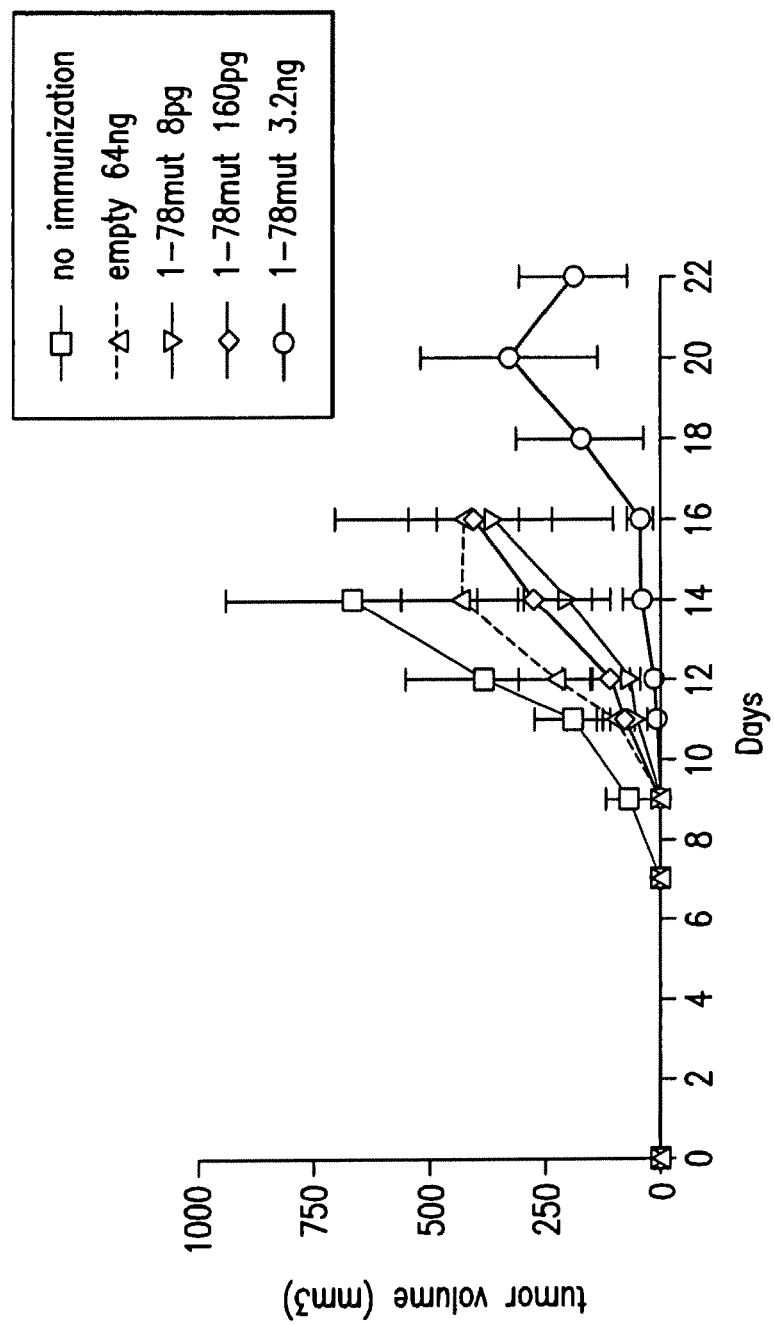

FIG. 4 shows prophylactic immunization of C57B6 mice with FS 1-78 neopeptide delays B16F10 tumor growth. C57B6 mice were immunized with the increasing amounts of LEE expressing FS 1-78 peptide and 1 μg of pGM-CSF. After a primary immunization mice were boosted 2 weeks later. One week after the boost, mice were challenged on day zero (arrow) with 1×105 B1 6F10 melanoma tumor cells.

Figure 5:
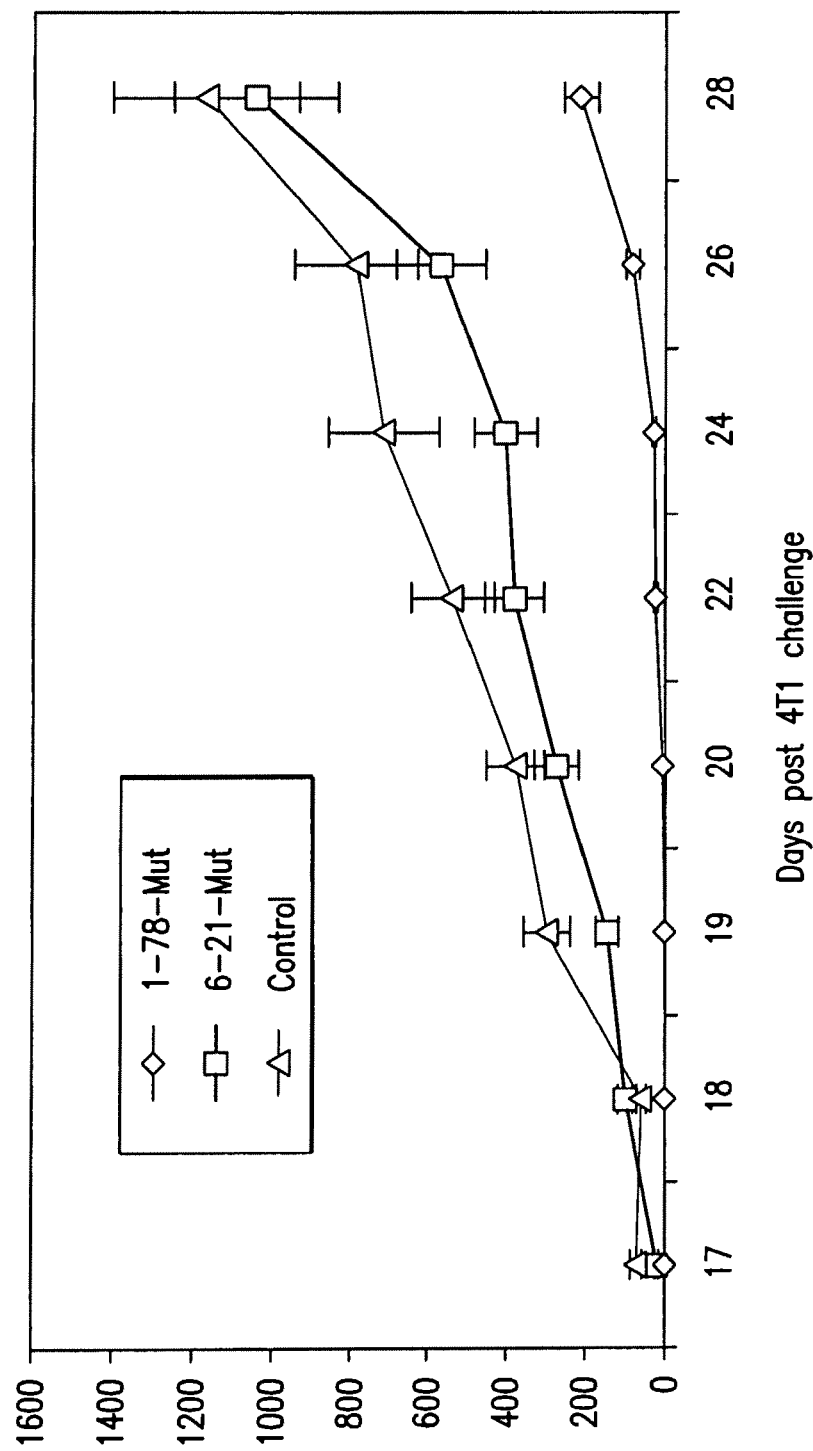

FIG. 5 shows prophylactic immunization of Balb/c mice with FS 1-78 neopeptide delays 4T1 tumor growth. Balb/c mice were immunized with 3.2 ng of FS 1-78 LEE+1 μg of pGM-CSF and boosted with the same gene vaccine after 2 weeks. One week after the boost, mice were challenged with 5×104 4T1 breast tumor cells. Seventeen days after 4T1 challenge, tumors started to grow. Control is pGM-CSF plasmid alone. 6-21-Mut is another frameshift not found in 4T1 tumors.

Figure 6:
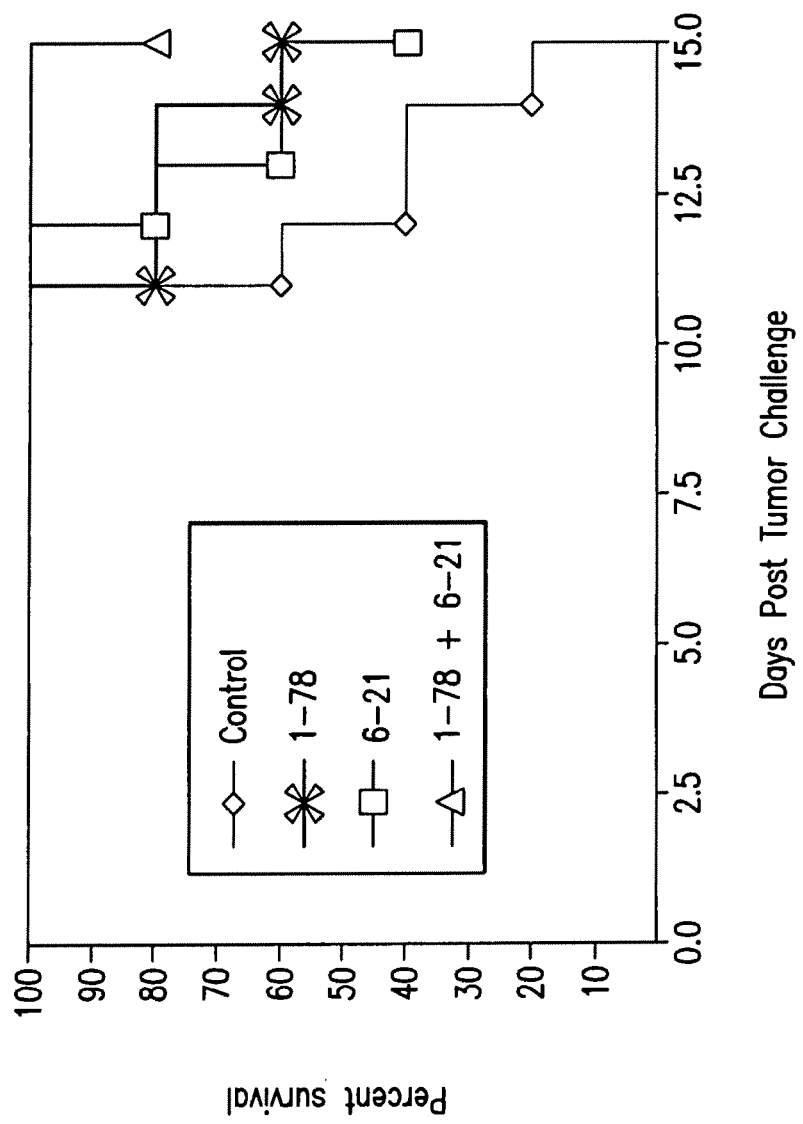

FIG. 6 shows the survival curve in response to prophylactic vaccination with frameshift peptide-encoding genetic vaccines. On Day −8, mice were immunized with the FS6-21mut peptide sequence (squares), the FS1-78mut peptide sequences (crosses), a combination of both (triangles), or an irrelevant peptide sequence (diamonds). Tumor cells were implanted on Day 0.

Figure 7A:
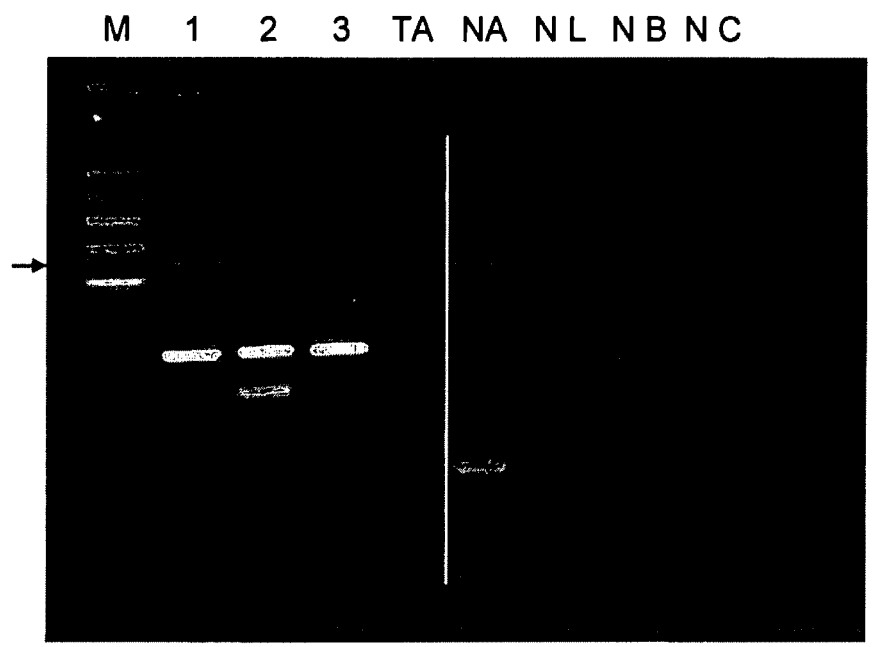
Figure 7B:
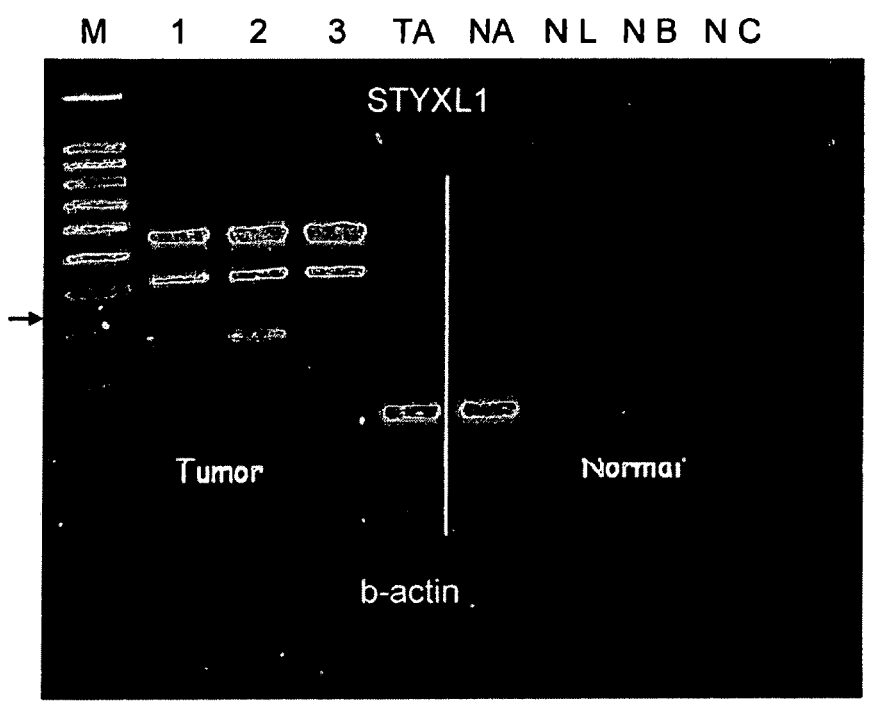
Figure 7C:
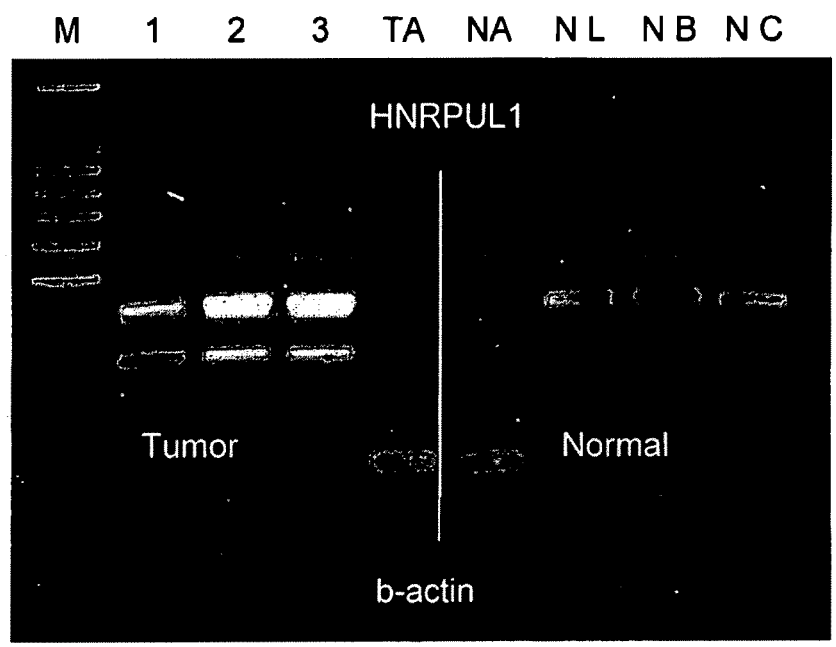

FIGS. 7a, 7b and 7c illustrate examples of a method for assessing the likely utility of a predicted candidate novopeptide as a cancer vaccine component by comparing the RNA expression level of the novopeptide in tumor cells with that in non-cancerous cells. FIG. 7a demonstrates amplification of a FS in BCL2L13 cDNA from three different human tumor cell lines, but not cDNA obtained from normal tissue. PCR primers were designed such that they flanked the BCL2L13 FS region and would amplify a FS of 253 bp indicated by the arrow. The left half of the figures are amplification of three different human tumor cDNA preparations. Lane labels in FIG. 7 are as follows. Lane M, 100 bp molecular weight marker; Lane 1, MCF-7 human breast cancer cell line; SW480 human colon cancer cell line; DU-145, human prostate cancer cell line; Lane TA beta actin from SW480 cell line. Right side of gel: Lane NA, beta actin from normal colon; Lane NL, normal lung; NB, normal breast; NC normal colon. FIGS. 7b and 7c show two more examples of amplification of cDNA from frameshifted genes called STYXL1 and HNRPUL1. The agarose gels shows frameshifts encoding a novopeptide present in tumor cells, but not present in cDNA from normal lung, breast and colon. PCR was performed as in 7a, but with primers that flank the predicted frameshifts. Arrows mark the FS bands in each figure. Lanes are the same as FIG. 7a.

Figure 8:
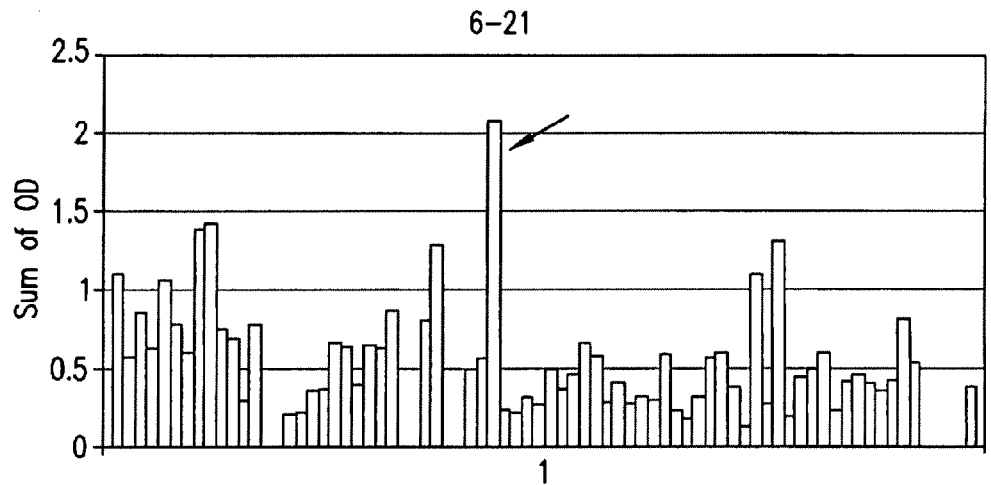

FIG. 8 shows that protective or therapeutic antibodies may be generated to FS after vaccination, serum taken from patients with different tumor types was assayed for reactivity with predicted novopeptides by standard ELISA techniques. The bar graph in FIG. 8 shows one cancer patient in 23 with antibody reactivity in sera to FS novopeptide sequences. Reactive sera is shown by the arrow.

Figure 9:
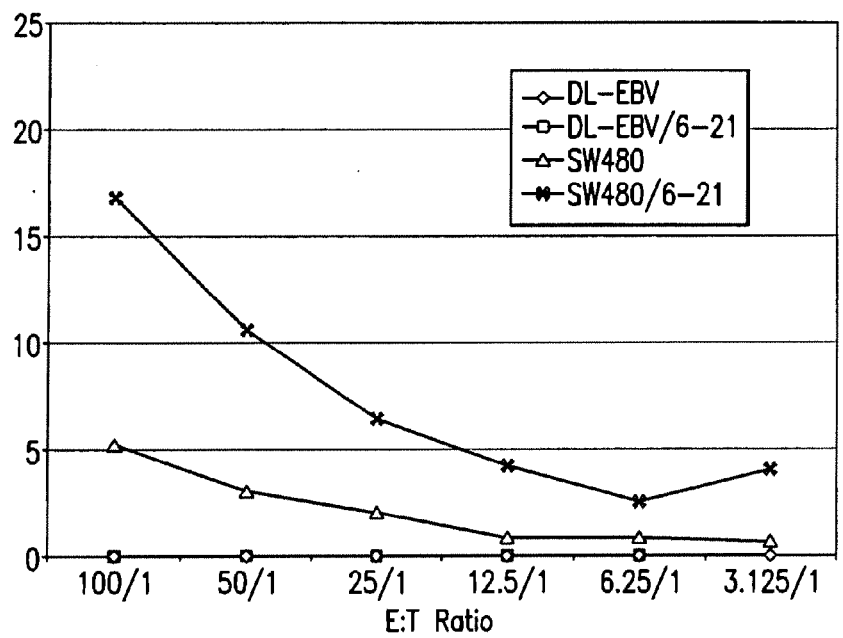

FIG. 9 shows that the probable immunoprotectiveness of a predicted novopeptide can be assayed by immunological screening via a CTL assay, and discloses one method for doing so. CTLs activated against novopeptide 6-21, described above were able to kill MHC-matched tumor cells pulsed with 6-21 novopeptide, but not unpulsed SW480 tumor cells as shown by the square symbol. Since SW480 tumor cells do not express 6-21 novopeptide endogenously, the cells required peptide pulsing.

Figure 10:
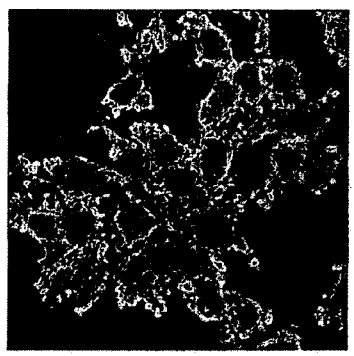
Figure 10:
Figure 10:
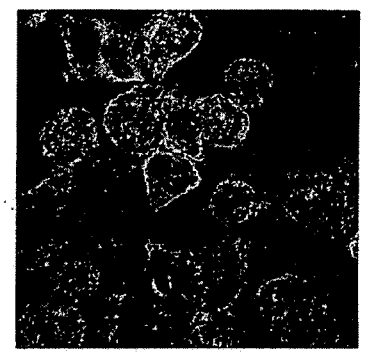

FIG. 10 shows immunofluorescence demonstrating that the B16 tumor line is presenting the FS6-21mut and FS1-78mut frameshift peptides and that the 4T1 breast tumor line is presenting the 1-78 peptide.

Figure 11:
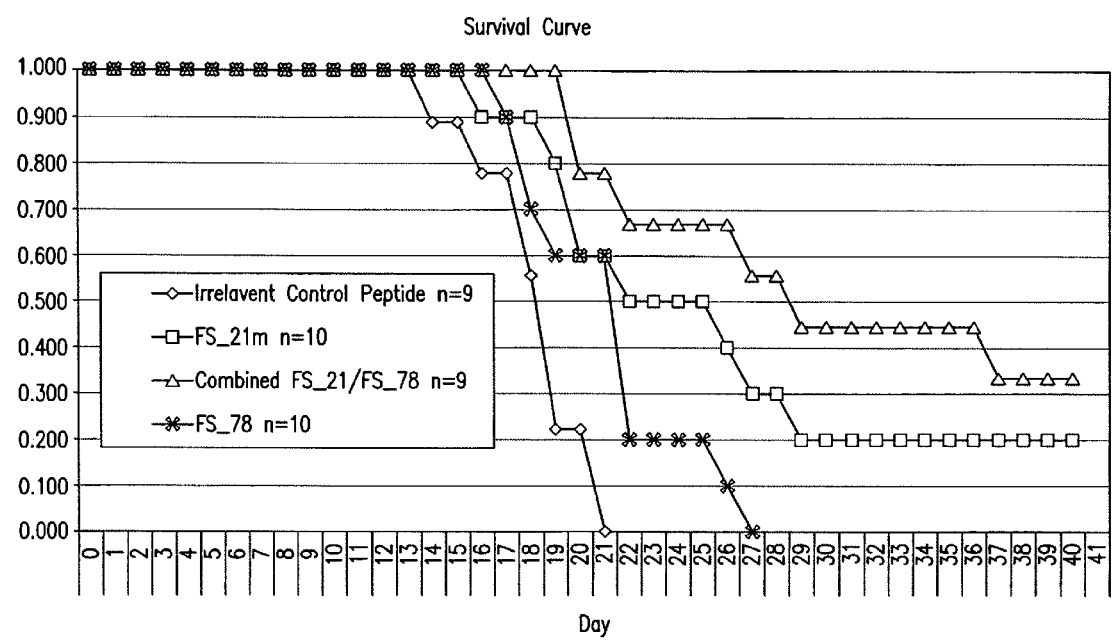

FIG. 11 shows an animal survival curve in response to therapeutic vaccination with frameshift peptide-encoding sequences. On Day 0, mice were injected with 105 tumor cells. One day later, mice were vaccinated with the FS6-21mut peptide sequence (squares), the FS1-78mut peptide sequences (crosses), a combination of both (triangles), or an irrelevant peptide sequence (diamonds).

Figure 12A:
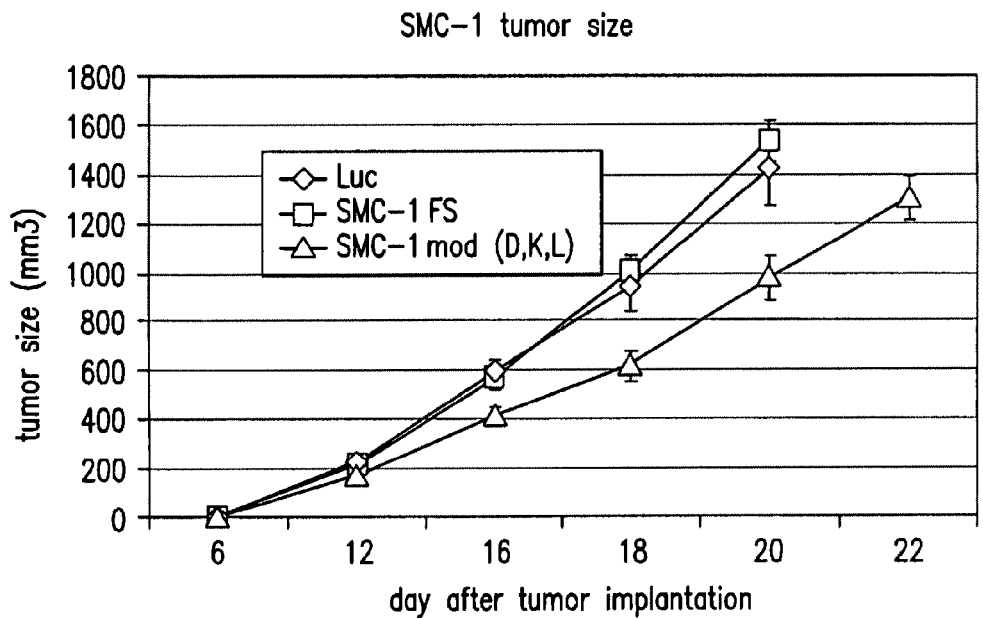
Figure 12B:
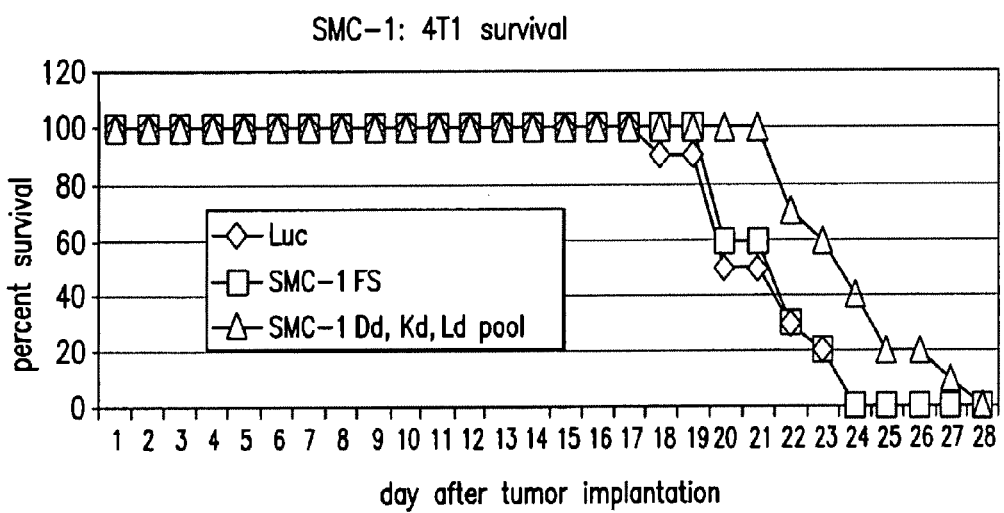

FIGS. 12a and 12b show tumor progression and survival over following tumor challenge in mice receiving therapeutic vaccination with a novopeptide associated with a frame shift mutation or variation in SMC-1.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Methods of Screening for Novopeptides and Novopeptide Associated Mutations and Variations The methods and compositions disclosed herein pertain in part to and comprise a class of TSA's, referred to herein as novopeptides, which are useful as candidates for cancer vaccines. Herein, "novopeptide" refers to any TSA comprising a polypeptide having at least 8 and no more than 40 amino acids, whose amino acid sequence is encoded by all or part of a novopeptide nucleic acid sequence. Thus, for example, a "novopeptide can comprise a TSA having 8, 9, 10, 11, 12, 13, 14, 15, 16, 17, 18, 19, 20, 25, 30, 35, or 40 amino acids or any number of amino acid residues in between. A "novopeptide nucleic acid sequence" means any nucleic acid sequence that can be generated from any non-cancerous reference sequence by a novopeptide associated mutation or variation. "Novopeptide" includes any such polypeptide regardless of how produced or obtained, whether naturally occurring, engineered, produced by in vitro translation, synthesized, or produced in any of the many other ways of generating polypeptides known to one having ordinary skill in the art. A "novopeptide associated mutation or variation" means one or a combination of any one or more point mutations, frame shift mutations, in-frame insertions or deletions, translocations, improper splicing, post-transcriptional events, variations, or other alterations in a nucleic acid sequence from a non-cancerous reference sequence, regardless of whether heritable or not, the effect of which is to cause the amino acid sequence or composition of a polypeptide encoded thereby to differ from that of the non-cancerous reference sequence; "novopeptide associated mutation or variation" expressly includes, without limitation, deviations from non-cancerous reference sequences occurring as a result of mis-translation, mis-splicing, or other events occurring at the RNA level. A "non-cancerous reference sequence" means and includes any nucleic acid sequence occurring in any non-cancerous cell of the organism of interest, whether or not expressed therein. The terms "cancerous cell" and "cancer cell" mean and include any cell exhibiting cancerous, precancerous, dysplagic or other changes characteristic of the transformation of a normal cell into a tumor cell, whether or not malignant and whether or not immediately tumorigenic. It will be recognized that the ontogeny of cancer typically entails a succession of cellular events, and that treatment, whether prophylactic or therapeutic, is optimally applied at the earliest possible stage of that succession. The methods and compositions disclosed herein are intended to apply not only to conditions that have progressed to the point where they are diagnosable as cancer but also to any and all conditions associated with the expression of novopeptides by cells in a manner immunologically distinguishable from normal cells. "Tumor cell" means a cell obtained from or associated with a tumor. "Noncancerous cell" means and includes any cell that is not a cancerous cell or tumor cell. Typically, a novopeptide is a linear polypeptide sequence comprising naturally occurring amino acids; however, "novopeptide" also includes any other polypeptide that can be expressed by a cancerous cell as a result of a novopeptide associated mutation or variation of a noncancerous reference sequence, whether occurring in DNA or RNA, whether or not comprising one or more amino acids that differ from the naturally occurring amino acids, whether or not post-translationally modified, and whether or not bonded to or associated with any one or more other moieties. A "FS-novopeptide" is a novopeptide whose sequence differs from that of a noncancerous reference sequence in a manner attributable to one or more novopeptide associated mutations or variations wherein the mutation or variation is a frame shift mutation or variation. A non-MS novopeptide is a novopeptide encoded by a novopeptide nucleic acid sequence that can be generated by a novopeptide associated mutation or variation from a non-cancerous reference sequence that is not a microsatellite sequence.

One interesting technology that has been developed to identify frameshifts without having to sequence genes is the high-throughput solid-phase protein truncation test (HTS-PTT) (Gite et al., 2003). However, the problem with this approach is that the user must have one or a few candidate proteins in mind at the outset, which reintroduces the problem of requiring knowledge about gene function or mechanism. Instead, in the present method, high-throughput sequencing capabilities and bioinformatics were used to identify FS cancer vaccine candidates, in contrast to prior methodology, the methods disclosed herein 1) do not require knowledge about gene function or immunological mechanism, 2) are systematic and amenable to high-throughput, and 3) are generalizable to all types of cancer. No other approach has all three of these characteristics. Furthermore, testing in the melanoma mouse model confirms that these novopeptides are effective therapeutic vaccines and prophylactic vaccines.

The least explored and potentially most useful subclass of TSA is arguably that caused by frameshifts (FS). One of the consequences of transformation from a normal cell to a cancer cell is that DNA replication and RNA processing become more error prone, while DNA repair becomes less robust. This causes an increase in the frequency of FS mutations or variants where 1 or 2 (or other non-multiple of three) new bases are inserted into or deleted from a gene. When such mutations occur in the coding regions of proteins, the resulting shift in reading frames gives rise to the synthesis of truncated genes that have lost their function. On average at least 20% of the FS variants would encode a new peptide of 9 or more amino acids. Since ~9 amino acids are required to bind in the MHC I pocket for presentation to T cells (e.g., 8, 9, 10, or 11 residues), many of the FS variants could be presented. It will be seen that even short FS variants will present new 9-residue peptides by virtue of the fusion of wild-type and FS sequences. Furthermore, as these nonsense proteins tend to be very immunogenic and are expressed predominantly (if not exclusively) in tumor cells, FS-derived antigens are ideal vaccine candidates. In addition to frameshifts, an insertion or deletion of a nucleic acid sequence that is a multiple of three will produce an in-frame deletion or insertion. These will also lead to the production of novopeptides since the junction points will be new peptide sequence.

Relative to oncogenesis, there are two classes of mutated proteins to consider, whether produced by frameshifts or other mechanisms: the first class, "oncogenic-related variants," are those that result in or contribute to tumor formation or progression. The second class, "bystander variants," are those that are not involved in oncogenesis but that happen to be altered simply because the cellular machinery is operating inefficiently. From the point of view of developing a vaccine, both are viable as vaccine candidates. Previous studies have looked for FS in specific cases, and have ignored the "bystander variants". For example, FS have been sought and found in hereditary nonpolyposis colon cancer (HNPCC). These cancers are caused by inherited or acquired defects in the DNA mismatch-repair machinery. Consequently looking for FS in genes carrying nucleotide repeat sequences represents a potentially rich source of FS antigens (Linnebacher et al., 2001; Saeterdal et al., 2001). However, this is a very specific case that applies to a specific type of cancer and therefore is not a generalizable approach to cancer vaccine discovery. In another example, investigators serendipitously stumbled upon a tumor-specific nonamer peptide antigen that was derived from translation of an alternative reading frame of the normal gp75 protein (Wang et al., 1996). This nonamer was recognized by the tumor infiltrate lymphocyte cell line, TIL586, indicating that it was indeed antigenic. However, no subsequent studies followed to show whether or not the peptide was biologically useful as a vaccine. In any case, no serious effort to identify cancer vaccine candidates can rely on serendipity. More recently, two specific frameshift peptides were patented for use in T cell assays (U.S. Pat. No. 6,759,046) and several other potential micro satellite associated FS peptides were disclosed. However, in U.S. Pat. No. 6,759,046 the peptides were derived from oncogenic proteins based on the assumption of a causal relationship between a frameshift within a known oncogene and a tumor. Moreover, the identified frameshifts that occurred downstream of the microsatellite were found informatically, and were described as useful in therapeutic vaccines for people identified with the particular FS in their tumors, or prophylactically in patients with a heritable disease who are very likely to develop colon cancer and produce these FS. This art consists of using the published human genome sequence to predict frameshift variants downstream of specific microsatellite repeats in oncogenes and proposes, but does not teach the possibility of using these prophylactically in people with heritable cancer known to have DNA repair defects. There was no method disclosed to evaluate how these peptides might be determined to be valid vaccine components. One cannot go from a predicted peptide to a vaccine component without a specific set of measures of efficacy. The peptide antigens envisioned were only frameshifts and were limited to frameshifts occurring at microsatellites. In contrast disclosed herein are methods to find and validate novopeptides, which are not limited to frameshift peptides and not limited to microsatellites.

Disclosed herein are methods of screening for a tumor-specific antigen, comprising obtaining a tumor cell, extracting RNA from the cell, and assaying for frameshifts. It is understood and herein contemplated that the tumor-specific antigen can be a peptide or protein.

Disclosed are methods of identifying components for a prophylactic cancer vaccine, comprising: identifying novopeptides by informatics, genomics, proteomics or immunological screens; and detecting an immune response to the novopeptide that differentiates between tumor and normal cells. The novopeptide so identified can be used to induce a primary immune response.

Disclosed herein are methods of identifying a novopeptide that produces an anti-cancer immune response, comprising identifying a novopeptide by informatics, genomics, proteomics, or immunological screens; and determining that the novopeptide induces an immune response that differentiates between tumor cells and normal cells. It is understood that the novopeptide of the method can be identified by any of the methods disclosed herein. Thus, for example, disclosed herein are methods, wherein the novopeptide is identified using cancer genome and expression databases to detect novopeptides preferentially expressed in tumor cells versus normal cells. Alternatively, disclosed are methods, wherein the novopeptide is identified using nucleic acid sequencing methods to detect alterations in DNA and or RNA that lead to the novopeptide. Also disclosed are methods wherein the novopeptide is identified using mass spectrometry to detect novopeptides that are on the tumor cell surface.

It is understood and contemplated herein that any immunoassay that can measure a T cell response can be used in the disclosed methods. Thus, for example, disclosed herein are methods of identifying a novopeptide that produces an anti-cancer immune response comprising determining that the novopeptide induces an immune response, wherein the novopeptide is identified using immune assays of human cancer patient serum or animal tumor model serum to detect reactivity to the novopeptide. Also disclosed are methods, wherein the novopeptide is identified using immune assays of human cancer patient peripheral blood mononuclear cells (PBMCs) or animal tumor model (PBMCs) to detect reactivity to the novopeptide. As noted above, the immune assay can be any assay known in the art that measures T cell activity. Thus, for example, the immune assay can be a cytolytic assay such as a 51Cr release assay, or the assay can measure cytokine production in response to the peptide such as ELISPOT, ELISA, and Intracellular Cytokine Staining Thus, disclosed herein are methods wherein the immune assay is selected from the group consisting of ELISPOT, ELISA, and Intracellular Cytokine Staining Antibodies may also be used to identify T cell activity by binding to T cells specific for a novopeptide. For example, MHC class I and II tetramers, dimers, and trimers can be used to mark novopeptide specific T cells.

Also disclosed are methods of identifying a novopeptide that induces a protective immune response to cancer, comprising identifying a novopeptide by informatics (odds ratios of tumor to normals); sequencing candidate DNA or RNA; performing mass spectrometry on peptides eluted from MHCI of tumor cells and normal cells, and detecting the peptides that are expressed by tumor cells; and determining whether T-cells reactive to the novopeptide peptide react with MHCI matched tumor cells but not normal cells. It is understood that additional steps may be needed to identify novopeptides. Thus, disclosed herein are methods, further comprising comparing the peptides eluted from tumor MHCI to a database of all possible novopeptides from the human proteome. It is also understood that antibody responses to a novopeptide can also be desirable in therapeutic methods. Therefore, disclosed herein are methods of identifying a novopeptide that induces a protective immune response to cancer, further comprising determining if antibodies raised to the novopeptide react with tumor cells expressing the novopeptide and not with normal cells. Also disclosed are methods of identifying a novopeptide that induces a protective immune response to cancer, comprising identifying a novopeptide by informatics (odds ratios of tumor to normals); sequencing candidate DNA or RNA; performing mass spectrometry on peptides eluted from MHCI of tumor cells and normal cells, and detecting the peptides that are expressed by tumor cells; and determining if antibodies raised to the novopeptide react with tumor cells expressing the novopeptide and not with normal cells.

It is understood and herein contemplated that the disclosed methods of identifying novopeptides that produce an anti-cancer immune response will produce peptides useful in producing an immune response to cancer. Thus, the novopeptides identified by the methods disclosed herein and those specifically elucidated can be used as a therapeutic or prophylactic agent to treat or prevent a cancer either alone or in combination with other peptides or known anti-cancer agents. Thus, for example, the disclosed methods can identify novopeptides that can be used to develop an anti-cancer vaccine. Therefore, disclosed herein are cancer vaccines comprising a novopeptide or nucleic acid encoding a novopeptide that has been identified by any of the methods of identifying novopeptides disclosed herein. It is understood and herein contemplated that such a vaccine can be delivered by any method known in the art including but not limited to gene gun, as gene vaccine, viral vector or as peptide or peptide fusion to another carrier such as a protein, sugar, or oil:water emulsion.

The disclosed prophylactic and therapeutic vaccines are suitable for administration to human and non-human subjects. Thus, disclosed herein are prophylactic vaccines that are administered to a non-human animal selected from the group consisting of dog, cat, guinea pig, mouse, rat, rabbit, pig, horse, cow, monkey, chimpanzee, or other non-human primate to prevent cancer.

Thus, disclosed herein are methods of identifying a novopeptide that induces a protective immune response to cancer, comprising identifying a novopeptide by informatics (odds ratios of tumor to normals); sequencing candidate DNA or RNA; performing mass spectrometry on peptides eluted from MHCI of tumor cells and normal cells, and detecting the peptides that are expressed by tumor cells; and determining whether T-cells reactive to the novopeptide react with MHCI matched tumor cells but not normal cells. It is understood that additional steps may be needed to identify novopeptides. Thus, disclosed herein are methods, further comprising comparing the peptides eluted from tumor MHCI to a database of all possible novopeptides from the human proteome. It is also understood that antibody responses to a novopeptide can also be desirable in therapeutic methods. Therefore, disclosed herein are methods of identifying a novopeptide that induces a protective immune response to cancer, further comprising determining if antibodies raised to the novopeptide react with tumor cells expressing the novopeptide and not with normal cells. Also disclosed are methods of identifying a novopeptide that induces a protective immune response to cancer, comprising identifying a novopeptide by informatics (odds ratios of tumor to normals); sequencing candidate DNA or RNA; performing mass spectrometry on peptides eluted from MHCI of tumor cells and normal cells, and detecting the peptides that are expressed by tumor cells; and determining if antibodies raised to the novopeptide react with tumor cells expressing the novopeptide and not with normal cells.

The disclosed methods can also be used in conjunction with animal models. Thus, disclosed herein are methods of identifying a novopeptide that produces an anti-cancer immune response, comprising identifying a novopeptide by informatics, genomics, proteomics, or immunological screens; and determining that the novopeptide induces an immune response that differentiates between tumor cells and normal cells, wherein the anticancer immune response of the novopeptide is further determined by administering a non-human animal homolog of a human novopeptide to the non-human animal in a prophylactic or therapeutic cancer model; and measuring the anti-cancer effect of the novopeptide in the animal model of cancer.

It is understood and herein contemplated that any of the disclosed methods benefit by the distinction and identification of immune responses limited to tumor cells (i.e., not present or present at only low levels in normal cells). Thus, disclosed herein are methods, for further identifying the induction of an immune response that differentiates between tumor cells and normal cells, wherein human cells are exposed to the novopeptide, and the reactivity of the exposed cells to human cancer cells and normal cells is determined, wherein a stronger reactivity against human cancer cells compared to normal cells indicates a cancer-specific immune response.

Tumor specific antigens can come from many sources. One advantage of the present method over previous methods is the identification of tumor-specific antigens in genes previously not associated with oncogenesis (i.e., cancer). For example, one source of tumor-specific antigens is frameshifts of genes. The genes can be oncogenic or non-oncogenic. A frameshift originating from an oncogene is an "oncogenic-related frameshift;" whereas, a frameshift derived from a non-oncogenic tumor gene is a "bystander frameshift." Thus, for example, specifically contemplated herein are tumor-specific antigens wherein the antigen is the result of a bystander frameshift in the gene source.

The method for identifying novopeptide vaccine antigens comprises two major tasks. The first, hereinafter referred to as a "novopeptide identification screen," entails identifying novopeptides and/or novopeptide nucleic acid sequences that are likely to be expressed and/or are experimentally determined to be expressed in one or more cancerous cell types. The second task, hereinafter referred to as a "novopeptide immunological screen," entails immunological screening of the novopeptides so identified, or novopeptides encoded by the novopeptide nucleic acid sequences so identified, to evaluate each candidate novopeptide for suitability as a component of a vaccine.

An important and novel insight underlying the invention here disclosed, and verified by the experiments described below, is that the widely held assumption that antigens expressed in cancerous cells and minimally expressed or not expressed in noncancerous cells are derived from oncogenes, particularly or exclusively those containing microsatellite sequences, does not withstand scrutiny, in fact, cancer cells can express many genes that have undergone a novopeptide associated mutation or variation, resulting in the expression of one or more non-MS novopeptides or other non-oncogene associated novopeptides by the cell.

The novopeptide identification screen in one aspect relates to identification of novopeptides that are expressed, or are predicted to be expressed, in cancerous cells. This can be accomplished in a number of ways, for example, the methods described by the examples disclosed herein. The method extends to the approaches described herein, which are offered as examples only and not intended to limit the scope of the invention, as well as any of the other methods known to persons having ordinary skill in the art for identifying peptides, peptide sequences, and/or nucleic acid sequences encoding peptides, that are experimentally determined to be expressed or predicted to be expressed in a predetermined cell type and/or that exhibit predetermined characteristics.

One method for performing the novopeptide identification screen comprises generating a library of candidate novopeptide sequences, and/or novopeptide nucleic acid sequences, bioinformatically from a known genome sequence or subsequence, or from cDNA, mRNA, EST, protein or peptide sequence, nucleic acid or peptide microarray data, or any other data from which the sequence encoding any non-cancerous reference sequence can be determined or inferred. At least one non-cancerous reference sequence is extracted from such data. Without limiting the generality of the foregoing, and by way of example only, one way of extracting a non-cancerous reference sequence from such data is to extract the DNA or RNA sequence corresponding to a known gene or open reading frame from available sequence data. Because many novopeptide associated mutations or variations are the result of events occurring at the level of RNA processing and/or translation, RNA sequences are another important source of sequence data for identification of candidate novopeptides. Ideally, a non-cancerous reference sequence so extracted is a sequence that, when mutated and fragmented and/or recombined to form novopeptide nucleic acid sequences, is likely to be expressed in a cancerous cell; however, novopeptide identification is in part a trial and error process, so not all non-cancerous reference sequences so extracted will be ideal. Nevertheless, the selection of non-cancerous reference sequences can, in appropriate circumstances, be optimized by any of the methods known to a person having ordinary skill in the art for estimating the likelihood of expression of a sequence, such as, by way of example only, taking into account the locus of the sequence in question with respect to a known promoter and/or other regulatory elements, and/or taking into account the relationship of the sequence in question to a gene known to be expressed in cancerous cells of a type for which a vaccine is desired. From each non-cancerous reference sequence extracted from the sequence data, one or more novopeptide nucleic acid sequences is generated by applying a novopeptide associated mutation or variation and extracting one or more subsequences affected by the novopeptide associated mutation or variation and having lengths corresponding to novopeptides of the desired length. Many other methods for identifying candidate novopeptide sequences from genomic, proteomic, or other similar data will be apparent to a person having ordinary skill in the art. Once a library of candidate novopeptide sequences has been generated, physical novopeptides can readily be generated therefrom by any of the many methods known to a person having ordinary skill in the art for synthesizing or producing physical polypeptides from specified sequences, including without limitation and by way of example only, FMOC synthesis, in vitro translation, and genetically engineered bacterial, phage, or yeast expression systems.

There exist large public databases that contain the sequences of DNA or cDNA from various tumor samples and from normal tissues. The NCI EST database currently contains more than 41 million entries. The Cancer Genome Atlas Project is another source of tumor cell sequence data. Comparison of sequences in the tumor databases to non-cancerous reference sequence open reading frames reveals putative insertions, deletions, mis-splicings, and other variations that can lead to translation and expression of novopeptides.

The invention in one aspect relates to the task of identifying novopeptides likely to be expressed in cancer cells and not in non-cancerous cells, accomplished by comparing EST sequences from a tumor database with EST sequences from a non-tumor related EST database to identify sequences arising from frame shift mutations or variations. EST sequences are particularly useful because they represent sequences known to be expressed, and capture variation occurring at the RNA level that may not be apparent in the corresponding DNA sequence, in this embodiment, all possible frame shifted sequences are generated from the non-tumor EST database, and the tumor EST database is then searched for sequences matching the frame shifted sequences so generated. The matching sequences found in the tumor EST database are then ranked for selection taking into account the number of times each frame shifted sequence appears in the tumor EST database as compared to the number of times the unshifted noncancerous reference sequence appears in the non-tumor EST database. Both databases are highly redundant, being repositories for data from many experiments by many researchers, and represent a reasonable sample of expression in tumor and non-tumor cells, respectively. Another factor to be taken into account is the size of the insertion or deletion resulting in a frameshift found in the tumor EST database. Insertions or deletions of three or fewer nucleotides have a significant likelihood of being due to sequencing errors, while longer insertions or deletions, particularly those appearing in multiple EST's deposited from multiple sources, are highly likely to represent true novopeptides that are actually expressed in tumor cells. It will be noted that the bioinformatic approach just described also provides information useful for selecting novopeptides that are expressed in multiple tumor types.

Another method for identifying novopeptides expressed in tumor cells entails extracting RNA from tumor cells and sequencing the RNA so extracted, using any of the methods familiar to a person having ordinary skill in the art for extracting and purifying RNA from cells and determining the sequence of the RNA. An interesting finding upon sequencing genes in human tumor cell lines for frame shift variants that are predicted to occur based on the bioinformatic prediction method describe herein is that most frame shifted sequences terminate at a shorter length than statistically expected. Since there are three stop codons, one expects a stop codon to occur on average approximately once every 3/20 amino acids, but many immediate terminations were observed and frame shift variants longer than 20 amino acids were rarely encountered.

Also disclosed herein are methods of performing a novopeptide identification screen comprising extracting novopeptides in physical form from a sample containing known or suspected cancerous cells, and identifying the novopeptides so extracted. A variety of methods exist that are capable of extracting any novopeptides that can be present in or on one or more cells (typically but not necessarily together with other substances that can be present in the sample including other cellular proteins and peptides). Several such methods are known to those of skill in the art, and include without limitation and by way of example only, washing with selected solvents or buffers, acid elution, sonication, and elution from MHC by competition with other chemical entities having an affinity for MHC. The method chosen can extract antigens present on the surface of cells in the sample. Methods that preferentially extract antigens displayed in MHC are of particular utility since novopeptides expressed by cancerous cells are likely to be so displayed. Once an extraction containing novopeptides has been obtained, the novopeptides contained therein can be characterized and their sequence determined by any of the methods known to a person having ordinary skill in the art for extracting and sequencing peptides from an inhomogeneous sample. Commonly used methods include without limitation sample separation by chromatographic and/or electrophoretic means, followed by characterization of the fractions thus separated, which can be by sequencing methods such as Edman degradation, or by mass spectroscopy. Other methods exist for identification of specific sequences using antibody or other probes, including without limitation ELISA and microarray analysis. A particularly useful and heretofore unfeasible approach enabled by the current invention is separation and identification of novopeptides by liquid chromatography and mass spectroscopy (LC-MS/MS). For a novopeptide to be most effective as a target for a vaccine, it should be presented on the outside of the tumor cells. For T-cell killing of the tumor the peptides should be presented in the context of an MHC molecule. For anti-tumor antibody binding the novopeptides need to be accessible on the surface in some form. Mass spectrometry allows the direct detection of particular sequences of peptides. Identification of novopeptides by MS has heretofore not been possible, in part because mass spectrometers having resolution sufficient to resolve peaks corresponding to novopeptides have only recently become available, and, more importantly, because identification of novopeptides by MS requires a database of novopeptide sequences and corresponding masses, and no such database has existed until created at the inventors' direction for purposes of the invention. Such a database can be constructed by assembling a set of candidate novopeptide nucleic acid sequences by any of the methods for doing so disclosed herein or known to a person of ordinary skill in the art, and analyzing each sequence using software (such as, by way of example only, BIMAS and/or SYFPEITHI) for predicting the ability of a sequence to bind to or be displayed in the MHC types present in the tumor cells from which the novopeptides are being eluted and to identify preferred 9-mer sequences or subsequences that are capable of being displayed in those MHC types. Spectra corresponding to each preferred 9-mer sequence so determined are generated and compared with spectra measured via LC-MS/MS using software (such as, by way of example only, Spectrum Mill) suitable for generating spectra from peptide sequences, comparing the spectra so generated with measured spectra, and from such comparison assessing whether a peptide sequence corresponds to any of the measured spectra. Because novopeptides may be present at low levels and only one sequence presented, until recently the sensitivity of mass spectrometry was not high enough to detect them. It should be noted that the method just described can be used both for identification of candidate novopeptides and as a screen to support or verify the identification by one of the other methods described.

Particularly with regard to human cancers, it is useful to perform bioinformatic screening of candidate novopeptides for likely HLA compatibility, since humans are outbred, while laboratory mice are not. It is understood and herein contemplated that the effectiveness of a particular novopeptide as a vaccine for human use depends in part upon the ability of the novopeptide to be displayed by the HLA types present in the human patient to whom it is administered. Vaccine candidate novopeptides can be assessed for likely ability to be displayed by given HLA types using algorithms known to those having ordinary skill in the art, such as, for example, those described herein. For vaccination of a particular human patient, the vaccine should preferably include one or more novopeptides predicted to have a high probability of binding to at least one of the HLA types expressed in the cells of the patient. For a vaccine intended for non-personalized use in humans, the vaccine should include one or more novopeptides in each of a number and selection of HLA types sufficient that a high percentage of individuals in the target population will have at least one of the HLA types represented in the vaccine, keeping in mind that it is not uncommon for one peptide to be presented by two or more MHC molecules, thereby reducing the number of distinct novopeptides required for a desired level of population coverage. It is also useful to take into account the particular tumor types in which particular novopeptides are expressed or are predicted to be expressed, the frequency with which those tumor types appear in the target population, the urgency of finding effective treatment or prophylaxis for those tumor types (keeping in mind that effective treatments exist for some cancers and that cancer types differ in terms of life expectancy after diagnosis and severity of effects), and any other criteria deemed important in designing a vaccine. This enables preferential selection for further testing of novopeptides that are expressed in multiple tumors, that are more commonly occurring, that are more urgently in need of an effective vaccine, or that meet other criteria.

Also disclosed are methods of performing a novopeptide identification screen comprising comparing the RNA expression level of a particular novopeptide in tumor cells of the type being targeted to the RNA expression level of the same novopeptide in one or more non-cancerous cell types. This can be accomplished by any of the methods known to a person having ordinary skill in the art for assaying for RNA expression levels, such as, without limitation and by way of example only, microarray expression analysis, reverse transcriptase PCR, and SAGE analysis. For inclusion in vaccines, novopeptides that are highly expressed in tumor cells and minimally expressed or not expressed in non-cancerous cells are preferred. For an effective vaccine, the novopeptide must be expressed in the tumor being targeted, and ideally not in non-cancerous cells, and since some novopeptides are highly differentially expressed in tumor vs. non-cancerous cells and others are not, the RNA expression level screen is useful for optimizing the selection of novopeptides for inclusion in vaccine formulations.

Disclosed herein are methods for performing novopeptide immunological screens. For example, disclosed herein are methods for immunologically screening for the existence of a B cell response to a particular novopeptide comprising assaying for the presence of antibodies reactive to that novopeptide in serum samples from individuals having a type of cancerous cells predicted to express the novopeptide, and for the absence, or presence below a prespecified titer, of such reactive antibodies in serum obtained from one or more individuals not having such cancer. The presence in sera of antibodies reactive to a given novopeptide is be detected and quantified by an ELISA assay in which the novopeptide is adsorbed onto a solid surface, serum is applied, and antibodies remaining bound to the novopeptides after washing are detected. The initial immune response to variant antigens displayed on naturally occurring tumors is suppression and tolerization due to the absence of the co-regulatory signals required for mounting of an immune response; this has been demonstrated clearly in animal models and is probably the case in humans. However, in at least some individuals, a strong immune response develops late in the tumor progression process. Therefore, serum antibody reactivity to a candidate novopeptide, even if detected in the serum of only one or a few individuals having the cancer type in question, is strong evidence that the novopeptide is expressed in that cancer type.

Thus, in one aspect, disclosed herein are methods for immunologically screening for a T cell response to a particular novopeptide comprising first preparing cytotoxic T lymphocytes ("CTL's") having T cell receptors specific for the novopeptide as displayed in MHC or HLA. These CTL's are then tested for reactivity against each of (1) cancerous cells, and (2) non-cancerous cells, each having an MHC or HLA type matching that of the MHC or HLA for which the CTL's are specific.

Another method for screening of novopeptides entails testing in a suitable animal model by immunizing with the novopeptide to be evaluated and observing whether the immunization is effective in producing a prophylactically or therapeutically effective immune response upon challenge with tumor cells, or in an animal having or prone to having a tumor. The response can be assessed by, for example, measuring tumor volume over time, or assessing survival rates, in comparison to non-immunized controls. Example 1 is illustrative of these methods.

Any one or more of the screening methods described in the preceding discussion can be used to identify novopeptides that are prevalent in tumors relative to noncancerous cells. By screening a panel of tumor and non-cancerous cells it is possible to establish the frequency of a novopeptide in specific tumor types as well as all tumors. Further, by screening a novopeptide against the known frequencies of HLA types it is possible to establish the percentage of a population that respond to the antigen.

As already noted, a second task to which the invention is directed is that of performing a novopeptide immunological screen of the candidate novopeptides identified via the novopeptide identification screen or otherwise. The goal of the novopeptide immunological screen is to determine the suitability of a given candidate novopeptide for inclusion in a therapeutic or prophylactic vaccine. The novopeptide immunological screen can be carried out by employing the methods disclosed in the preceding paragraphs, or by any of the methods known to a person having ordinary skill in the art for determining or estimating the likely efficacy and safety of a biomolecule as a vaccine component, singly or in combination and in any appropriate order, in one embodiment, the novopeptide immunological screen entails determining whether T-cells made reactive to the novopeptide exclusively or disproportionately react with cancerous cells but not normal cells. With regard to B-cell response, a novopeptide immunological screen may entail determining whether antibodies against the novopeptide specifically react against tumor cells and not normal cells. Novopeptides are inherently relatively unlikely to be expressed in non-cancerous cells, since novopeptides are derived from altered nucleic acid sequences. It is obviously preferable that novopeptide vaccine antigens not be expressed in non-cancerous cells, since such expression would imply a likelihood of existing tolerance, and since it is preferable that a vaccine not produce an immune response against non-cancerous cells. However, the preference for non-expression in non-cancerous cells is not a rigid one, since even treatments that produce undesired side effects can be therapeutically useful.

Disclosed herein are methods and compositions useful in the formulation of prophylactic and/or therapeutic vaccines to be administered for the purpose of raising an immune response against tumor cells. The invention extends to the composition of novopeptide-based vaccines and to methods of administration thereof. A novopeptide-based vaccine can be prepared and administered in any of the ways familiar to persons having ordinary skill in the art, including the very simple approach of preparing a vaccine comprising a novopeptide dissolved or suspended in a suitable carrier, and administering it once or at predetermined intervals to the animal or human patient to be vaccinated. However, better success may be had by other methods, and a particular approach entails genetic immunization using gene gun technology, in which the vaccine is administered in the form of a linear expression element encoding the desired novopeptide, as illustrated in the examples below. The composition of a vaccine can include both novopeptide and other components. The inclusion of multiple distinct novopeptides can improve the level of imrnunoprotection conferred, and by conferring imrnunoprotection against additional tumor types; single novopeptides can be found that confer imrnunoprotection against more than one tumor type, but the repertoire of target tumor types can be expanded by inclusion of additional novopeptides. The inclusion of multiple novopeptides is of particular utility in vaccines intended for administration in humans, due to the need for including a number and selection of novopeptides sufficient to ensure that at least one novopeptide in the vaccine will be capable of being displayed by at least one HLA type present in each individual in a predetermined percentage of the target population. For example, two or more novopeptides can be fused into a single entity. Novopeptide-based vaccines can include other components familiar to a person having ordinary skill in the art for improving the imrnunoprotection conferred or otherwise improving the efficacy and/or safety of the vaccine formulation, including without limitation and by way of example only, adjuvants and hapten carriers.

Experiments have been performed to assess directly the feasibility of creating general prophylactic cancer vaccines and therapeutic cancer vaccines, in contrast to existing dogma, results from these experiments indicate that it is possible to immunize prophylactically with novopeptide vaccines that cross-protect across different tumor types and in different MHC backgrounds. These results show that cancer vaccines do not have to be personalized; can contain a defined set of tumor specific antigens (novopeptides) that cover the majority of human MHCs; and would avoid the necessity of delaying treatment until an individual develops a tumor (at which point the battle is nearly lost) so that a sufficient personalized sample can be obtained to allow formulation of a drug or vaccine.

The tumor-specific antigens (novopeptides) of the invention can come from any known tumor cell. Thus contemplated herein are methods of screening for tumor specific antigens, wherein the tumor cell is from a cancer cell selected from the group of cancers consisting of lymphomas (Hodgkins and non-Hodgkins), B cell lymphoma, T cell lymphoma, leukemias, myeloid leukemia, carcinomas, carcinomas of solid tissues, squamous cell carcinomas, squamous cell carcinomas of the mouth, throat, larynx, and lung, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, mycosis fungoides, bladder cancer, brain cancer, nervous system cancer, lung cancers such as small cell lung cancer and non-small cell lung cancer, ovarian cancer, pancreatic cancer, prostate cancer, hepatic cancer, colon cancer, cervical cancer, cervical carcinoma, breast cancer, and epithelial cancer, renal cancer, genitourinary cancer, esophageal carcinoma, head and neck carcinoma, large bowel cancer, hematopoietic cancers, and testicular cancer. The source of novopeptides can be from any tumor type and some novopeptides are applicable to a wide variety of tumors; when pooled, an appropriate selection of such novopeptides can give rise to a universal prophylactic vaccine.

An advantage of the disclosed approach is that it provides insights into cancer. For example, one of the 11-mer frameshift peptides that was isolated (F56-21mut) was found to have homology to a region of Huntingtin interacting protein (HIP1), the level of which is positively correlated with disease progression in patients with Huntington's disease (Kerr, 2002). Interestingly, there are a number of studies that have shown that this disorder is associated with a significantly lower incidence of cancer (Sorenson et al., 1999).

C. Compositions

Provided are novopeptides that are associated with cancer cells. The disclosed components can be used to prepare the disclosed compositions as well as in the compositions themselves to be used within the methods disclosed herein. These and other materials are disclosed herein, and it is understood that when combinations, subsets, interactions, groups, etc. of these materials are disclosed, while specific reference of each various individual and collective combinations and permutation of these compounds may not be explicitly disclosed, each is specifically contemplated and described herein. For example, if a particular novopeptide or novopeptide associated mutation or variation (e.g., FS1-78mut, FS6-21mut, and FS SMC1) SMC 1 is disclosed and discussed and a number of modifications that can be made to a number of molecules including the FS1-78mut, FS6-21mut, and FS SMC1 are discussed, specifically contemplated is each and every combination and permutation of FS1-78mut, FS6-21mut, and FS SMC 1 and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The disclosed screening methods can be used to identify novopeptide associated mutations or variations associated with cancers. The disclosed novopeptide associated mutations or variations are differentially expressed in cancerous cells as compared to noncancerous cells. Since novopeptide associated mutations or variations occur in all cancers tested, the novopeptides furnish a basis for therapeutic vaccines. Therefore, disclosed herein are vaccines for a cancer comprising one or more novopeptides, wherein the novopeptide is derived from a novopeptide associated mutation or variation, and wherein the novopeptide(s) is identified via the disclosed screening methods or by any other method. Specifically disclosed herein are novopeptides, wherein the novopeptide is associated with a frameshift of the SMC1 gene. Disclosed herein, are frameshift mutation peptides that have been identified that are present only in cancerous tissue. See, for example, the list of peptides in the Sequence Listing. Specifically disclosed herein are tumor-specific antigens, wherein the antigen is a peptide as set forth in SEQ ID NOs: 2, 4, 6, and 8. It is understood that there are numerous nucleotide sequences that can encode for the peptides disclosed herein. For example, one example of a nucleotide that encodes the peptide set forth in SEQ ID NOs: 2, 4, and 6 are the nucleotide sequences of SEQ ID NOs: 1, 3, and 5, respectively. It is understood and herein contemplated are each and every nucleotide sequence that encodes the disclosed peptides.

Because the novopeptides in the Sequence Listing have been shown by the present screening method to be present only in non-normal (e.g., cancerous) tissue, each disclosed novopeptide can be used as a reagent for detecting the presence of anti-novopeptide antibodies in a subject. Thus, the novopeptides have utility in a method of detecting the presence of non-normal (e.g., cancerous) tissue in a subject as further described below.

Because the novopeptide associated mutation or variation is present and/or expressed at higher levels in cancerous tissue as compared to normal or noncancerous tissue, the novopeptide associated mutations or variations itself can be used as the basis for a target for drug or antibody treatment as well as methods of identifying subjects at risk for a cancer by virtue of the presence of the novopeptide associated mutation or variation. Therefore, the disclosure hereof extends to antibodies to novopeptides or FS-novopeptides or non-MS novopeptides. It is understood that the antibody can be specific to any novopeptide disclosed herein. For example, the antibody can be directed to a frameshift mutant of the SMC1 gene. The disclosure hereof extends, by way of example only, to antibodies directed toward a novopeptide comprising the sequence set forth in SEQ ID NOs: 2, 4, 6, or 8. It is understood that the antibody can be administered by itself or as a component of another composition. Thus, herein disclosed are compositions comprising antibodies specific for the tumor specific antigens disclosed herein. The vaccines of the invention can be used to treat or prevent cancer due to the presence of the novopeptides or novopeptide associated mutations or variations in tumor cells. Alternatively, since the mutation does not occur in normal cells it can also be used as a prophylactic vaccine. Thus disclosed herein are compositions comprising a prophylactic vaccine made of the above components such that they would be predicted to provide protection to 10% or more of the population against a particular tumor or group of tumors by multiplying the frequency of the peptides in the tumors by the frequency of the MHCIs in the population.

Thus, disclosed herein are methods of treating cancer comprising administering to a subject in need thereof the vaccines disclosed herein. Also disclosed herein are methods of preventing a cancer comprising administering to a subject at risk thereof the vaccines disclosed herein. The disclosed vaccines can be used to treat cancer due to the presence of disclosed tumor-specific antigens in all cancers. It is understood that herein contemplated are vaccinations for treating or preventing cancer wherein the cancer is selected from the group of cancers consisting of lymphomas (Hodgkins and non-Hodgkins), B cell lymphoma, T cell lymphoma, leukemias, myeloid leukemia, carcinomas, carcinomas of solid tissues, squamous cell carcinomas, squamous cell carcinomas of the mouth, throat, larynx, and lung, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, mycosis fungoides, bladder cancer, brain cancer, nervous system cancer, lung cancers such as small cell lung cancer and non-small cell lung cancer, ovarian cancer, pancreatic cancer, prostate cancer, hepatic cancer, colon cancer, cervical cancer, cervical carcinoma, breast cancer, and epithelial cancer, renal cancer, genitourinary cancer, esophageal carcinoma, head and neck carcinoma, large bowel cancer, hematopoietic cancers, and testicular cancer.

It is understood that the antibodies disclosed herein can be combined with other agents, molecules, or compounds to increase binding, elicit additional immune responses, or deliver toxic effects to the proximity of the target antigen, e.g., to cells that express the frameshift mutation. Such combinations can occur through the formation of fusion constructs, immunoconjugates, or other combination platform known in the art. Thus, it is understood that the antibodies disclosed herein can be combined with a toxin such as diphtheria toxin, ricin toxin, tetanus toxoid, botulinum toxin, or any other toxin as a fusion construct to form an antibody-toxin fusion. For example, the antibody-toxin fusion construct can comprise the disclosed antibody fused to a diphtheria toxin. It is understood herein that the disclosed toxins such as tetanus and diphtheria can comprise truncation mutants to avoid the antibody response from previous exposure to the toxin. For example, a diphtheria toxin can comprise a truncation mutant diphtheria toxin wherein the toxin comprises a 145-152 amino acid truncation of the c-terminal end of the diphtheria toxin 1. Sequence Similarities It is understood that as discussed herein the terms homology, similarity, and identity are interchangeable. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

Homology can be determined for nucleic acids by any of the methods known to a person having ordinary skill in the art, including without limitation, for example, the algorithms disclosed in Zuker, M. Science 244:48-52, 1989, Jaeger et al. Proc. Natl. Acad. Sci. USA 86:7706-7710, 1989, Jaeger et al Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Nucleic Acids

There are a variety of molecules disclosed herein that are nucleic acid based, including for example the nucleic acids that encode, for example FS1-78mut, FS6-21mut, FS SMC1, or fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. The disclosure hereof extends to the nucleic acid sequences described herein and to any and all other nucleic acids that are similar or homologous thereto, regardless of whether comprised in whole or in part of nucleotides, nucleotide analogs, or nucleotide substitutes, or any combination thereof and regardless of whether or not linked to conjugates or other molecules or moieties. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups ($NH_2$ or O) at the C6 position of purine nucleotides.

b) Sequences

There are a variety of sequences related to the protein and/or peptide molecules disclosed herein, including without limitation and by way of example only, FS1-78mut, FS6-21mut, and FS SMCI, or any of the nucleic acids disclosed herein, including without limitation and by way of example only, those encoding all or part of FS1-78mut, FS6-21mut, and FS SMCI. The disclosure hereof extends to analogs of these genes, as well as other alleles of these genes, and splice variants and other types of variants, in humans and in any other species exhibiting specific immunity including without limitation mammals, fish, and birds. The sequences of various of the foregoing to the extent currently known are available in a variety of protein and gene databases, including Genbank. Such sequences available at the time of filing this application at Genbank are herein incorporated by reference in their entireties as well as for individual subsequences contained therein. Genbank can be accessed at www.ncbi.nih.gov/entrez/query.fcgi. Those of skill in the art understand how to resolve sequence discrepancies and differences and to adjust the compositions and methods relating to a particular sequence to other related sequences. Primers and/or probes can be designed for any given sequence given the information disclosed herein and known in the art.

3. Peptides a) Protein Variants

As discussed herein there are numerous variants of the FS1-78mut, FS6-21mut and FS SMC1 protein that are known and herein contemplated. In addition to the known functional FS1-78mut, FS6-21mut, and FS SMC1 variants there are derivatives of the FS1-78mut, FS6-2 limit, and FS SMC1 proteins which also function in the disclosed methods and compositions. Protein and peptide variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to ten residues. Deletions are characterized by the removal of one or more amino acid residues from the protein sequence. These variants may be prepared by site specific mutagenesis of nucleotides in the DNA encoding the protein, thereby producing DNA encoding the variant, and thereafter expressing the DNA in recombinant cell culture, or by any of the other methods known to a person having ordinary skill in the art for making or obtaining proteins or peptides having a specified sequence. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Substitutions, deletions, insertions or any combination thereof may be combined to arrive at a final construct. Mutations to DNA encoding the variant must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 6 and 7 and are referred to as conservative substitutions.

TABLE 6

Amino Acid Abbreviations

| Amino Acid | Abbreviations | |
|---|---|---|
| alanine | Ala | A |
| allosoleucine | Alle | |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isoleucine | Ile | I |
| leucine | Leu | L |
| lysine | Lys | K |
| phenylalanine | Phe | F |
| proline | Pro | P |
| pyroglutamic acid | | |
| serine | Ser | S |
| threonine | Thr | T |
| tyrosine | Tyr | Y |
| tryptophan | Trp | W |
| valine | Val | V |

TABLE 7

Amino Acid Substitutions

| Original Residue | Exemplary Conservative Substitutions, others are known in the art |
|---|---|
| Ala | Ser |
| Arg | Lys, Gln |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. For example, the FS novopeptide can be fused to a carrier such as a protein or sugar. Methods for improving the immunogenic properties of a peptide by fusing, conjugating or otherwise associating it with a hapten or other carrier are well known to persons having ordinary skill in the art of immunology.

The replacement of one amino acid residue with another that is biologically and/or chemically similar is known to those skilled in the art as a conservative substitution. Without limiting the generality of the foregoing, and by way of example only, the substitutions shown in Table 7 are conservative substitutions. Conservative substitutions include any substitution that would be regarded by one having ordinary skill in the art as conservative, and include, without limitation, substitutions having a log odds score of zero or above in the BLOSUM 62 matrix, or having a relatively high log odds score in any other substitution matrix in common usage. For example, a conservative substitution may entail replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the polypeptides disclosed herein.

Substantial changes in function or immunological identity are made by selecting substitutions that are less conservative than those in Table 7, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, He, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 1 sets forth a particular sequence of FS1-78mut and SEQ ID NO:2 sets forth a particular sequence of a FS1-78mut peptide. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sd. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:2 is set forth in SEQ ID NO:1. In addition, disclosed conservative derivatives of SEQ ID NO:1 are also disclosed. It is also understood that while no amino acid sequence indicates what particular DNA sequence encodes that protein within an organism, where particular variants of a disclosed protein are disclosed herein, the known nucleic acid sequence that encodes that protein is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 6 and Table 7. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 11:A2>-12>(1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Biotechnology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include CH2NH—, —CH2S—, —CH2-CH2-, —CH═CH- (cis and trans), —COCH2-, —CH(OH)CH2-, and —CHH2SO—. (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH2NH—, CH2CH2-); Spatola et al. Life Sci 38:1243-1249 (1986) (—CH H2-S); Hann J. Chem. Soc Perkin Trans. 1307-314 (1982) (—CH—CH—, cis and trans); Almquist et al. J. Med. Chem. 23:1392-1398 (1980) (—COCH2-); Jennings-White et al. Tetrahedron Lett 23:2533 (1982) (—COCH2-); Szelke et al. European Appln, EP 45665 CA (1982): 97:39405 (1982) (—CH(OH)CH2-); Holladay et al. Tetrahedron. Lett 24:4401-4404 (1983) (—C(OH)CH2-); and Hruby V., Sci 31:189-199 (1982) (—CH2-S—); each of which is incorporated herein by reference. A particularly preferred non-peptide linkage is —CH2NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D-amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

D. Methods of Using the Compositions

1. Method of Preventing or Treating Cancer

The disclosed compositions can be used for the treatment or prophylaxis against any disease where uncontrolled cellular proliferation occurs such as cancers. It is understood and herein contemplated that the novopeptide associated mutation or variation can be any novopeptide associated mutation or variation disclosed herein. Therefore, disclosed herein are methods of treating a cancer comprising administering a composition to a subject in need thereof, wherein the composition comprises a novopeptide, a FS-novopeptide, a non-MS novopeptide, a non-MS novopeptide that is also a FS-novopeptide, and/or any combination of the foregoing. Thus, for example, the novopeptide associated mutation or variation can be a frameshift of the SMC1 gene. It is also understood that the frameshift can be a peptide. Thus, by way of example only and without limiting the generality of the foregoing, disclosed herein are methods of treating cancer comprising administering to a subject in need thereof a composition comprising a novopeptide, wherein the novopeptide comprises the sequence set forth in SEQ ID NOs: 2, 4, 6, or 8.

The invention in one aspect relates to the identification of novopeptides, including, for example, novopeptides referred to herein as novopeptide vaccine antigens, suitable for inclusion in a prophylactic or therapeutic cancer vaccine. A "novopeptide vaccine antigen" is a novopeptide that is capable, when administered in an appropriately constituted prophylactic or therapeutic vaccines, of fostering an appreciable immune response, which may be humoral, cellular, or both, against at least one cancerous cell type in at least one individual.

Experiments have been performed to assess directly the feasibility of creating general prophylactic cancer vaccines and therapeutic cancer vaccines. In contrast to existing dogma, results from these experiments indicate that it is possible to immunize prophylactically with novopeptide vaccines that cross-protect across different tumor types and in different MHC backgrounds. These results show that cancer vaccines do not have to be personalized; can contain a defined set of tumor specific antigens (novopeptides) that cover the majority of human MHCs; and would avoid the necessity of delaying treatment until an individual develops a tumor (at which point the battle is nearly lost) so that a sufficient personalized sample can be obtained to allow formulation of a drug or vaccine.

The utility of the invention has been convincingly demonstrated in an animal model, disclosed herein, and selected aspects of the invention capable of being demonstrated without a need for human clinical testing have been experimentally confirmed in other experiments disclosed herein. The invention is applicable to human and murine cancers, and similarly to cancers of all other organisms having mechanisms for specific immunity, specifically including all mammals, as well as birds and fish. The invention is of high potential significance not only in providing prophylactic and therapeutic interventions for human cancer, but also for its veterinary applications, particularly in companion animals such as dogs and cats, for which cancer is a leading cause of death. This invention disclosed herein can readily be applied to dog cancer since the dog genome sequence determination has been completed.

While significant progress has been made over the past decade in understanding the basic immunology underlying cancer, thus far no one has produced a cancer vaccine that can, reliably and consistently, induce tumor destruction or improve patient survival (Lewis, 2004; Leaf, 2004). The scientific literature discloses a variety of cancer vaccination strategies that have been investigated by others, each proving less than ideal. The majority of personalized cancer vaccine studies to date have focused on the use of undefined whole tumor-cell extracts prepared from a patient's own tumor. Experiments using autologous vaccines in melanoma have shown that, in principle, immunologic intervention can enhance specific anti-tumor immune responses, and even mediate regression in some cases, but this approach presents difficult challenges, including (1) the potential for causing autoimmunity; (2) dilution of TAAs since the majority of antigens will be "normal"; (3) undermining of specificity (one of the most attractive unique features of immunotherapy); (4) dependence on the patient having a large enough tumor to make the vaccine, precluding early treatment; and (5) the need for custom preparation of a personalized vaccine for each patient.

Another approach to cancer vaccination is to use vaccine formulations composed of known and defined TAAs, since this maximizes specificity and obviates the problem of antigen dilution. To date, several hundred human TAAs have been identified using a variety of strategies, and criteria exist for selecting TAAs suitable for immunotherapy. Functionally, TAAs may be classified as self and non-self. Self-TAAs are derived from non-mutated genes whose expression is limited to certain tissues or to over-expressed proteins. Most TAAs identified and tested to date are self antigens. Potential problems associated with such antigens include autoimmunity and tolerance. For practical purposes, this limits the use of self TAAs to non-vital organs (such as reproductive organs). Pre-existing immune tolerance to self antigens is also problematic, for not only does it suppress a desired anti-tumor immune response, but more recently it has emerged as a possible mechanism of immune escape.

All or most TSAs are non-self antigens and can originate either exogenously (such as those derived from viral proteins in virally-associated tumors, e.g. human papilloma virus) or endogenously. The latter subclass includes un-mutated proteins that might never have been presented to the immune system before (some embryonic or immune privileged antigens), as well as mutated proteins that arise as a consequence of mutations in tumors. Mutation-derived TSAs can arise from events such as point mutations, frame shift mutations, translocations, improper splicing, and post transcriptional events. TSAs have a great advantage over self TAAs as cancer vaccines since they avoid the problems of autoimmunity and systemic tolerance. In mouse models TSAs have been shown to generate high-avidity T cell responses more readily than self TAAs.

In principle, vaccination can be used either prophylactically or therapeutically. As a practical matter, therapeutic vaccination strategies face several difficult challenges, and, in general, have failed to fulfill their early promise. Many or most antigens presented by cells in an established tumor are recognized as self by the immune system. To the extent that tumor cells do display mutated antigens that the immune system is capable of recognizing as non-self, by the time tumor development has advanced sufficiently to allow diagnosis, immune tolerance to the mutated antigens will have developed owing to their gradual exposure to the immune system in the absence of the co-regulatory danger signals that would be required for an immune response. Recent studies have shown that in the absence of co-stimulatory signals, tolerance can be induced even to foreign antigens expressed by a tumor. MHC expression is often down-regulated or impaired in established tumor cells, reducing the display of any non-self antigen, and the reduced MHC expression is of course selected for to the extent that any therapeutic immunization strategy is effective in killing cells that do display recognizable non-self antigen in MHC. (The term "MHC" is used herein in a generic sense and is intended to include MHC, HLA, and any other entities at least one of whose functions is to display endogenous or exogenous antigens or fragments thereof on the surface of a cell. Where reference is made to a particular MHC class, the reference includes any corresponding class of HLA or other such entity.) Finally, it has been shown by multiple groups that immunization with irradiated tumor cells, tumor cell lysate, or tumor-derived heat shock proteins (HSPs) protects only against challenge with the same tumor; it does not protect against challenge with a different tumor; vaccines derived from one tumor did not protect against another. These findings have led to an assumption nearly universally held in the field of cancer immunology, but disproved by the experimental evidence disclosed herein, that cancer vaccines must be personalized. Companies exist based on a technology in which they receive a tumor from a patient, isolate HSPs or extracts from that tumor, and return the tumor derived HSPs or extracts as a patient-specific vaccine. Early clinical trials implementing this approach showed promise, but it is expensive and not every cancer patient has enough tumor from which to make a vaccine. A recent Phase III trial by Antigenics, Inc. using this strategy was stopped for lack of efficacy.

A fundamental problem for prophylactic vaccination as a cancer preventative treatment has been the supposition that each tumor in each organism presents a unique immunological profile, and the consequent assumption that no prophylactic vaccine could offer a practicable breadth of protection against multiple tumor types or even against multiple variants of a single tumor type. The problem is exacerbated by the assumed need for any vaccine to be personalized to the organism receiving it. In contrast, a basic contention hereof is that there are novopeptides that are produced in common between two or more types of cancers and that these can be used to formulate a prophylactic vaccine. The challenge was is to develop a systematic method to find such novopeptides; such a method is disclosed herein.

The peptides disclosed herein can be administered to a subject as a peptide or encoded by a nucleic acid. Thus, for example, disclosed herein are methods of treating a cancer comprising administering a composition to a subject in need thereof, wherein the composition comprises a tumor-specific antigen, and wherein the tumor-specific antigen is a novopeptide, a FS-novopeptide, a non-MS novopeptide, a non-MS novopeptide that is also a FS-novopeptide, and/or any combination of the foregoing, and wherein the tumor-specific antigen is a peptide encoded a nucleic acid set forth in SEQ ID NOs: 1, 3, or 5. The nucleic acids encoding the novopeptides disclosed herein can be provided by any gene delivery system disclosed herein such as gene gun, viral vector, or plasmid.

"Treatment" means a method of reducing the effects of a disease or condition. Treatment can also refer to a method of reducing the disease or condition itself rather than just the symptoms. The treatment can be any reduction from native levels and can be but is not limited to the complete ablation of the disease, condition, or the symptoms of the disease or condition. For example, a disclosed method for reducing the effects of a cancer is considered to be a treatment if there is a 10% reduction in one or more symptoms of the disease (e.g., tumor size) in a subject with the disease when compared to native levels in the same subject or control subjects. Thus, the reduction can be a 10, 20, 30, 40, 50, 60, 70, 80, 90, 100%, or any amount of reduction in between as compared to native or control levels. It is also understood and contemplated herein that treatment can refer to any reduction in the progression of a disease or cancer. Thus, for example, methods of reducing the effects of a cancer is considered to be a treatment if there is a 10% reduction in the tumor growth rate relative to a control subject or tumor growth rates in the same subject prior to the treatment. It is understood that the reduction can be a 10, 20, 30, 40, 50, 60, 70, 80, 90, 100%, or any amount of reduction in between as compared to native or control levels.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The disclosed methods can be used for the treatment or inhibition of any cancer. Thus disclosed herein are methods of treating, preventing, or inhibiting cancer, wherein the cancer is selected from the group of cancers consisting of lymphomas (Hodgkins and non-Hodgkins), B cell lymphoma, T cell lymphoma, leukemias, myeloid leukemia, carcinomas, carcinomas of solid tissues, squamous cell carcinomas, squamous cell carcinomas of the mouth, throat, larynx, and lung, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, mycosis fungoides, bladder cancer, brain cancer, nervous system cancer, lung cancers such as small cell lung cancer and non-small cell lung cancer, ovarian cancer, pancreatic cancer, prostate cancer, hepatic cancer, colon cancer, cervical cancer, cervical carcinoma, breast cancer, and epithelial cancer, renal cancer, genitourinary cancer, esophageal carcinoma, head and neck carcinoma, large bowel cancer, hematopoietic cancers, and testicular cancer.

It is understood that, in addition to the present methods of identifying a subject at risk of developing cancer, the identification of subjects at risk of developing a cancer can be accomplished by any means known in the art. Thus, for example, a subject at risk can be identified by exposure to a known carcinogen, behavioral activities associated with cancer (e.g., smoking with respect to lung cancer), or genetic predisposition to a given cancer. Specifically disclosed herein are methods of preventing a cancer in a subject at risk thereof wherein the subject is identified by genetic screening. Because the frameshift peptides disclosed herein are associated with cancer, the presence of the frameshift can be used to identify subjects at risk of developing a cancer. Therefore, disclosed herein are methods of identifying a subject at risk for developing a cancer comprising obtaining a tissue sample from the subject and contacting the antibody with the tissue sample, wherein antibody binding indicates the subject is at risk for the cancer.

Compounds disclosed herein may also be used for the treatment of precancer conditions such as cervical and anal dysplasias, other dysplasias, severe dysplasias, hyperplasias, atypical hyperplasias, and neoplasias.

The disclosed methods can be used to treat or protect any subject in need thereof or at risk of acquiring any disease disclosed herein. Disclosed herein, "subject" can refer to any animal capable of displaying specific immunity such as bird, fish, and mammal. Thus, for example, a subject for use with any of the disclosed methods can be human, chimpanzee (or other non-human primate), monkey, cow, horse, pig, dog, cat, rat, guinea pig, and mouse.

A significant advantage of the invention is that vaccination with a single novopeptide has been shown capable of conferring immunoprotection against more than one tumor type and in unrelated individuals, as demonstrated by the examples disclosed herein. This is a highly novel result, particularly in the light of the widely held dogma based on the whole-cell vaccine studies previously noted that immunization with one tumor cell line does not cross-protect against another. The results shown here may be reconciled with the whole-cell vaccine studies by observing that tumors do have antigens in common, but immunization with cell lysates or irradiated tumors do not show cross-protection because the concentration of cross protective peptides in MHC is not high enough in whole-cell vaccines to activate T cells; in other words, whole-cell vaccine strategies fail because of antigen dilution. Pre-vaccination with one or a few novopeptides concentrates the immune system on these antigens and confers protection. This experimental finding leads to the very important result that novopeptides expressed in common by multiple tumor types can support prophylactic vaccination conferring immunoprotection against those tumor types. This is an important conceptual, experimental, and practical breakthrough. It will be noted that the invention provides an effective and systematic method for finding and evaluating novopeptides that are commonly expressed among multiple tumor types.

In some cases a novopeptide produced in human tumors will be the same or very similar to that produced in an animal tumor model such as mouse or dog. For example, the 1-78 and 6-21 novopeptides described below were found in mouse tumors as there described, but have also been identified in certain human tumors. The SMC1 novopeptide, described below, was found originally by searching human databases, but also is expressed in mouse tumors. If a novopeptide is found in both human and mouse tumors, significant evidence of the potential effectiveness of the novopeptide as a tumor vaccine antigen in humans can be obtained by immunizing mice and challenging with the appropriate tumor line. Alternatively, cancer prone mice can be vaccinated with the novopeptide to determine whether tumorigenesis and/or tumor progression is reduced or eliminated.

Disclosed herein are therapeutic antibodies to tumor-specific antigen, wherein the antigen is a novopeptide identified by the steps comprising identifying a novopeptide by informatics, genomics, proteomics, or immunological screens; and determining that the novopeptide induces an immune response that differentiates between tumor cells and normal cells. It is understood and herein contemplated that the novopeptide can be a tumor-specific antigen. Thus, for example, the novopeptide can comprise the sequence set forth in SEQ ID NO: 2, 3, 6. Similarly, the novopeptide can comprise a frameshift of the SMC1 gene. Thus for example, the novopeptide can comprise the sequence set forth in SEQ ID NO: 8. It is also understood that the disclosed therapeutic antibodies can be used alone or in combination with another agent as a therapeutic treatment. It is also contemplated herein that the therapeutic treatments disclosed herein can be used to treat cancer. In other words, disclosed herein are methods of treating a cancer comprising administering to a subject the therapeutic antibodies disclosed herein or identified by the methods disclosed herein. Thus, for example, disclosed herein are methods of therapeutic treatment, wherein the cancer is selected from the group of cancers consisting of lymphomas (Hodgkins and non-Hodgkins), B cell lymphoma, T cell lymphoma, leukemias, myeloid leukemia, carcinomas, carcinomas of solid tissues, squamous cell carcinomas, squamous cell carcinomas of the mouth, throat, larynx, and lung, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, mycosis fungoides, bladder cancer, brain cancer, nervous system cancer, lung cancers such as small cell lung cancer and non-small cell lung cancer, ovarian cancer, pancreatic cancer, prostate cancer, hepatic cancer, colon cancer, cervical cancer, cervical carcinoma, breast cancer, and epithelial cancer, renal cancer, genitourinary cancer, esophageal carcinoma, head and neck carcinoma, large bowel cancer, hematopoietic cancers, and testicular cancer.

2. Methods of Using the Compositions as Research Tools

The compositions can be used for example as targets in combinatorial chemistry protocols or other screening protocols to isolate molecules that possess desired functional properties related to inhibiting tumor growth and treating cancer. Thus, disclosed herein are methods of screening for a cancer therapeutic or prophylactic comprising contacting the candidate therapeutic or prophylactic with a novopeptide, wherein a candidate therapeutic or prophylactic that binds the novopeptide is selected for further evaluation as a therapeutic or prophylactic.

The disclosed compositions can also be used as diagnostic tools related to diseases such as cancer. For example, the disclosed methods can be used to determine if a cell growth is cancerous. Thus, disclosed herein are methods of diagnosing a tumor or other growth as cancerous or precancerous comprising screening for a novopeptide comprising obtaining a tumor cell, extracting RNA from the cell, and assaying for novopeptide associated mutations or variations, wherein the presence of a novopeptide associated mutation or variation indicates the tumor is cancerous or potentially cancerous. Also disclosed are methods of diagnosing an individual with cancer comprising obtaining a tissue sample, and screening for the presence of a novopeptide associated mutation or variation. It is understood that the tissue can be any tissue present in the subject. For example, the tissue can be blood, saliva, skin, or cells from a tissue biopsy. It is also understood that the disclosed tissues can be obtained by any method known in the art such as, for example, lung lavage, venous bleeding, tissue biopsy, or mucosal tissue swab. Thus, for example, disclosed herein are methods of diagnosing wherein the sample is blood. The method can involve determining the presence of a novopeptide associated mutation or variation identified to be associated with cancer. Alternatively, the method can involve screening for the presence of an immune response to a novopeptide. It is understood that the immune response can be an antibody or cell-mediated response. Thus, for example, the immune response can be a T cell response such as a CD8 T cell response (e.g., cytolytic killing or cytokine secretion) or CD4 T cell response (cytokine secretion). It is specifically contemplated herein that any known immunological measure may be used to determine the presence of the immune response. For example, antibody responses can be measured by ELISA, ELISPOT, or agglutination assays. T cell responses can be detected by, for example, ELISA, ELISPOT, tetramer staining, intracellular cytokine staining, or chromium release assays.

It is understood that the novopeptide associated mutations or variations identified by the methods disclosed herein may result in an otherwise non-oncogenic gene becoming oncogenic. For example, the SMC1 gene is not oncogenic; however, a frameshift of the SMC1 gene as disclosed herein is oncogenic. The methods of detecting novopeptide associated mutations or variations in tumor cells disclosed herein showed a frameshift in the SMC1 gene which as a frameshift mutant is oncogenic. Thus, it is understood that disclosed herein are methods of identifying oncogenes, comprising detecting a novopeptide associated mutation or variation in a gene not previously associated with cancer.

E. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods EnzymoL, 65:610-620 (1980), (phosphotriester method). Protein nucleic acid molecules can be made using known methods such as those described by Nielsen et al., Bioconjug. Chem. 5:3-7 (1994).

2. Peptide Synthesis

One method of producing the disclosed proteins, such as SEQ ID NO:23, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (Xert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

F. Antibodies

1. Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with FS1-78mut, FS6-21mut, and FS SMC1 such that tumor growth is inhibited. The antibodies can be tested for their desired activity using the in vitro assays described herein, or by analogous methods, after which their in vivo therapeutic and/or prophylactic activities are tested according to known clinical testing methods.

As used herein, the term “antibody” encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (1), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-I, IgG-2, IgG-3, and IgG-4; IgA-I and IgA-2. One skilled in the art would recognize the comparable classes for mouse. The heavy chain constant domains that correspond to the different classes of immunoglobulins are called alpha, delta, epsilon, gamma, and mu, respectively.

The term “variable” is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., “Sequences of Proteins of Immunological Interest,” National Institutes of Health, Bethesda, Md.). The constant domains are not involved directly in binding an antibody to an antigen, but exhibit various effector functions, such as participation of the antibody in antibody-dependent cellular toxicity.

As used herein, the term “antibody or fragments thereof encompasses chimeric antibodies and hybrid antibodies, with dual or multiple antigen or epitope specificities, and fragments, such as F(ab')2, Fab', Fab, sFv, scFv, and the like, including hybrid fragments. Thus, fragments of the antibodies that retain the ability to bind their specific antigens are provided. For example, fragments of antibodies which maintain FS1-78mut, FS6-21mut, FS SMC1 binding activity are included within the meaning of the term “antibody or fragment thereof.” Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of “antibody or fragments thereof are conjugates of antibody fragments and antigen binding proteins (single chain antibodies) as described, for example, in U.S. Pat. No. 4,704,692, the contents of which are hereby incorporated by reference.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M J. Curr. Opin. Biotechnol. 3:348-354, 1992).

The term “monoclonal antibody” as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include “chimeric” antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sd. USA, 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

2. Human Antibodies

The disclosed human antibodies can be prepared using any technique. Examples of techniques for human monoclonal antibody production include those described by Cole et al. (Monoclonal Antibodies and Cancer Therapy, Alan R. Liss, p. 77, 1985) and by Boemer et al. (J. Immunol., 147(1):86-95, 1991). Human antibodies (and fragments thereof) can also be produced using phage display libraries (Hoogenboom et al., J. Mol. Biol, 227:381, 1991; Marks et al., J Mol. Biol, 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl Acad. ScL USA, 90:2551-255 (1993); Jakobovits et al., Nature, 362:255-258 (1993); Bruggermann et al., Year in Immunol., 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

3. Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen), in some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human, in practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol, 2:593-596 (1992)).

Methods for humanizing non-human antibodies are well known in the art. For example, humanized antibodies can be generated according to the methods of Winter and co-workers (Jones et al., Nature, 321:522-525 (1986), Riechmann et al., Nature, 332:323-327 (1988), Verhoeyen et al., Science, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

4. Administration of Antibodies

Administration of the antibodies can be done as disclosed herein. Nucleic acid approaches for antibody delivery also exist. The broadly neutralizing antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

G. Compositions Identified by Screening with Disclosed Compositions/Combinatorial Chemistry The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions disclosed in SEQ ID NOS: 2, 4, 6, and 8 or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions are also disclosed.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, TIBS 19:89, 1992). One synthesizes a large pool of molecules bearing random and defined sequences and subjects that complex mixture, for example, approximately 1015 individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in 1010 RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A method for isolating proteins that have a given function is described by Roberts and Szostak (Roberts R. W. and Szostak J.W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3' end of the RNA molecule. An in vitro translation of this modified RNA molecule causes the correct protein, encoded by the RNA to be translated, in addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3' end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302 (1997)).

Another method for combinatorial methods designed to isolate peptides is described in Cohen et al. (Cohen B. A., et al., Proc. Natl. Acad. Sci. USA 95(24): 14272-7 (1998)). This method utilizes and modifies two-hybrid technology. Yeast two-hybrid systems are useful for the detection and analysis of protein-protein interactions. The two-hybrid system, initially described in the yeast *Saccharomyces cerevisiae*, is a powerful molecular genetic technique for identifying new regulatory molecules, specific to the protein of interest (Fields and Song, Nature 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example, is FS1-78mut attached to a DNA binding domain of a transcriptional activation protein, such as Gal 4. By performing the Two-hybrid technique on this type of system, molecules that bind FS 1-78mut, can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic tetrahydroquinolines (U.S. Pat. No. 5,925,527), benzofurans (U.S. Pat. No. 5,919,955), isoquinolines (U.S. Pat. No. 5,916, 899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

H. Delivery of the Compositions to Cells

An accomplishment of the invention is to furnish methods and compositions useful in the formulation of prophylactic and/or therapeutic vaccines to be administered for the purpose of raising an immune response against tumor cells. The invention extends to the composition of novopeptide-based vaccines and to methods of administration thereof. A novopeptide-based vaccine may be prepared and administered in any of the ways familiar to persons having ordinary skill in the art, including the very simple approach of preparing a vaccine comprising a novopeptide dissolved or suspended in a suitable carrier, and administering it once or at predetermined intervals to the animal or human patient to be vaccinated. However, success may be had by other methods, and a particular approach entails genetic immunization using a gene gun technology, in which the vaccine is administered in the form of a linear expression element encoding the desired novopeptide, as illustrated in Experiments 2 and 3 below. The composition of a vaccine may include both novopeptide and other components. The inclusion of multiple distinct novopeptides may prove useful, where possible, in improving the level of immunoprotection conferred as illustrated by Experiment 4 below, and by conferring immunoprotection against additional tumor types; as Experiment 3 demonstrates, single novopeptides may be found that confer immunoprotection against more than one tumor type, but the repertoire of target tumor types may be expanded by inclusion of additional novopeptides. The inclusion of multiple novopeptides is of particular utility in vaccines intended for administration in humans, due to the need for including a number and selection of novopeptides sufficient to ensure that at least one novopeptide in the vaccine will be capable of being displayed by at least one HLA type present in each individual in a predetermined percentage of the target population. Two or more novopeptides may be fused into a single entity; this is a standard practice in the field of vaccine design. Novopeptide-based vaccines may include other components familiar to a person having ordinary skill in the art for improving the immunoprotection conferred or otherwise improving the efficacy and/or safety of the vaccine formulation, including without limitation and by way of example only, adjuvants and hapten carriers.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

1. Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as FS1-78mut into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in nonproliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase II transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

a) Retroviral Vectors

A retrovirus is an animal virus belonging to the virus family of Retroviridae, including any types, subfamilies, genus, or tropisms. Retroviral vectors, in general, are described by Verma, L M., Retroviral vectors for gene transfer, in Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

b) Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 51:261-21 A (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. CHn. Invest. 92:381-387 (1993); Roessler, J Clin. Invest. 92:1085-1092 (1993); Moullier, Nature Genetics 4:154-159 (1993); La Salle, Science 259:988-990 (1993); Gomez-Foix, J Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

c) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

d) Large Payload Viral Vectors

Molecular genetic experiments with large human herpesviruses have provided a means whereby large heterologous DNA fragments can be cloned, propagated and established in cells permissive for infection with herpesviruses (Sun et al., Nature Genetics 8: 33-41, 1994; Cotter and Robertson. Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable the maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

2. Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed FS1-78mut, FS6-21mut, FS SMC1, as vectors, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Feigner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Lie. (San Diego, Calif.) as well as by means of a SONOPORATION machine (hnaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of delivery, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

3. In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

I. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

1. Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a Hmd1H E restriction fragment (Greenway, P J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. ScL 78:993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed, in certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs, in certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

2. Markers

The viral vectors can include nucleic acid sequence encoding a marker product. This marker product is used to determine if the gene has been delivered to the cell and once delivered is being expressed. Preferred marker genes are the E. Coli lacZ gene, which encodes P-galactosidase, and green fluorescent protein.

In some embodiments the marker may be a selectable marker. Examples of suitable selectable markers for mammalian cells are dihydro folate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

J. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

1. Pharmaceutically Acceptable Carriers

The compositions, including antibodies, can be used therapeutically in combination with a pharmaceutically acceptable carrier.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders maybe desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

2. Therapeutic and Prophylactic Uses

Effective dosages and schedules for administering the compositions may be determined empirically, and making such determinations is within the skill in the art. The dosage ranges for the administration of the compositions are those large enough to produce the desired effect in which the symptoms/disorder are/is affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 mg/kg to up to 100 mg/kg of body weight or more per day, depending on the factors mentioned above.

Following administration of a disclosed composition, such as a vaccine or an antibody, for treating, inhibiting, or preventing a cancer, the efficacy of the y or prophylaxis can be assessed in various ways well known to the skilled practitioner. For instance, one of ordinary skill in the art will understand that a composition, such as a vaccine or an antibody, disclosed herein is efficacious in treating, inhibiting, or preventing a cancer in a subject by observing that the composition reduces tumor growth or prevents a further increase in tumor size.

K. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for assessing a subject's risk for acquiring prostate cancer, comprising the peptides set forth in SEQ ID Nos: 2, 4, and 8.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

L. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in 0 C or is at ambient temperature, and pressure is at or near atmospheric.

1. Example 1

Identification of Novopeptides a) Frequency of Frameshift

To determine the amount of coding sequence that must be sequenced to identify a sufficient number of novopeptides that are expressed in tumor cells and not in non-cancerous cells to constitute a cancer vaccine, it is first necessary to determine the frequency of novopeptide associated mutation or variation in a tumor is first determined. To assess this frequency, the C-terminal 600 bp of 550 genes that are expressed in the mouse melanoma cell line, B16-F10 were sequenced. To confirm that the in vztro-derived FS were expressed in vivo, RNA was extracted from B16 lung metastases after injection of cells systemically, cDNA was generated, and the FS confirmed by RT-PCR sequencing (FIG. 1).

Figure 2:
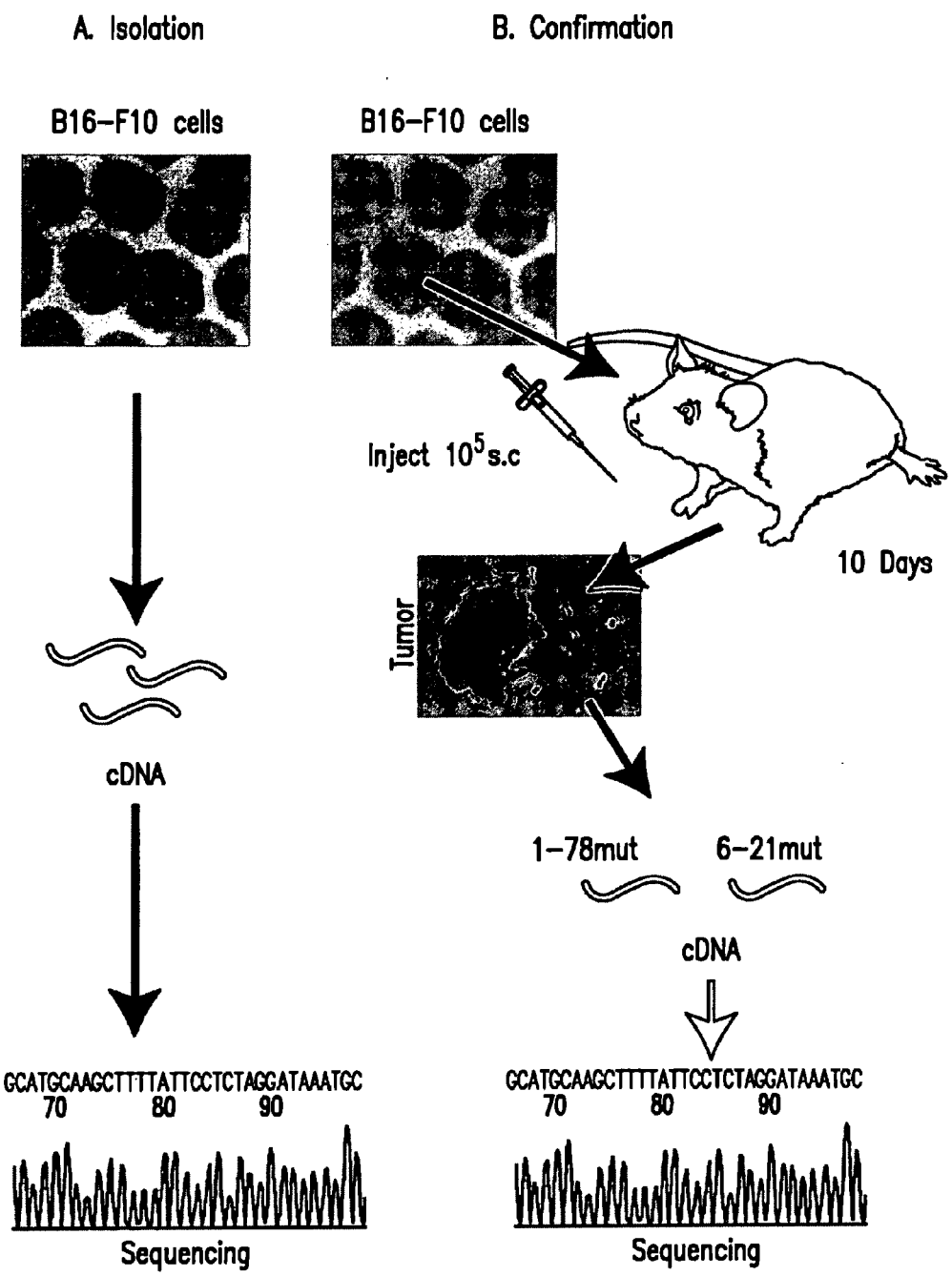

Three FS were isolated, indicating that FS occur at a frequency of roughly one per 183 segments of 600 bp of genes (FIG. 2). FS 1-78 was identified as a frameshift relative to the normal reference sequence. One other frameshift peptide, 6-21 was also identified, as was a 3 amino acid insertion. The parent protein of FS 1-78 is a zinc finger protein, but a deletion of 396 bp results in expression of an 11 amino acid novopeptide in an alternate frame before termination. Table 1 shows the sequences identified. Underlined amino acids comprise the peptide predicted to be presented by H-2 Db (C57BL6 mice) and H-2 Kd (Balb/c mice). Upper case amino acids indicate primary frame and lower case amino acids indicate the frame shift residues. Fusions of primary and alternate frames often form antigenic peptides (e.g. bcr-abl fusion). FIG. 2a shows PCR amplification of FS1-78. Arrow indicates FS 1-78 band; other bands are wild type alleles. Lane 1: B16/F10 tumor cells; Lane 2: B16/F10 tumor cells; Lane 3: normal heart; Lane 4: normal intestine; Lane 5: normal kidney; Lane 6: normal liver; Lane 7: normal lung; Lane 8: normal skeletal muscle; Lane 9: normal skin; Lane 10: normal spleen; Lane M: Molecular weight marker. FIG. 2b shows the analysis of the occurrence of the 6-21 frameshift in the mouse tumor versus RNA from normal tissue. Arrow indicates 6-21 FS band. Lanes are as in FIG. 2a. It is noted that FS 1-78 expression is detected in the tumor cells and not in any of the noncancerous cells tested. TABLE 1 Underlined amino acids comprise the peptide predicted to be presented by H-2 Db (C57BL6 mice) and H-2 Kd (Balb/c mice). Amino acids shown in capital letters indicate primary frame and amino acids shown in lower case letters indicate FS.

b) Immunoprotection Against Tumor Progression

The FS 1-78 novopeptide identified above was chemically synthesized as a genetic linear expression element (LEE) as diagrammed in FIG. 3 according to the methods described in (Sykes, K. F., and S. A. Johnston (1999) Nat Biotechnol 17:355). Each LEE is comprised of a fragment that contains a mammalian promoter, the ubiquitin gene (Ub) for strong intracellular processing, and a fragment that contains transcriptional and translational terminators. The two fragments are linked via the frameshift sequence, here FS 1-78. C57BL6 mice were then genetically immunized with the FS 1-78 LEE construct and a plasmid expressing GM-CSF using gene gun technology (1 µg of pGM-CSF). Mice were boosted 2 weeks later with the same FS 1-78 LEE and pGM-CSF and then challenged one week after boost with 1×105 B16 F10 melanoma tumor cells. As shown in FIG. 4, tumor growth was markedly delayed compared to mice administered control empty LEE and compared to those receiving no immunization, and at the highest dose (3.2 ng), tumor volume decreased after the already delayed rise.

c) Cross-Protection with a Single FS-Novopeptide

Immunization with a single FS-novopeptide identified based on one tumor type is immunoprotective against a different tumor type in a different mouse strain, and discloses a procedure for such immunization. Disclosed herein, immunization with novopeptides common to multiple types of tumors can result in cross-protection, obviating the requirement that a patient must develop a tumor before a personalized vaccine can be formulated, prepared and administered. Balb/c mice were immunized in the same manner as the C57BL6 mice above, with 3.2 ng of FS 1-78 LEE+1 µg of pGM-CSF, and boosted with the same gene vaccine after 2 weeks. One week after the boost, mice were challenged with 1×1044T1 breast tumor cells. Seventeen days after 4T1 challenge, tumors started to grow. As shown in FIG. 5, prophylactic immunization of Balb/c mice with FS 1-78 novopeptide significantly delayed and reduced 4T1 tumor growth in comparison to both controls immunized with pGM-CSF plasmid alone and controls immunized with another novopeptide (6-21 Mut) that is not found in 4T1 tumors.

d) Combining Multiple Novopeptides can Confer Immunoprotection Against Cancer

Vaccines combining more than one novopeptide can be highly effective in conferring immunoprotection against cancer. Herein, mice were vaccinated using a vaccine comprising a combination of 1-78 and 6-21 novopeptides. On challenge with B16 tumor cells, most vaccinated mice were completely protected from tumor growth. FIG. 6 compares the relative protection of the 1-78 and 6-21 peptides by themselves and when pooled as a single vaccine. The 80 percent of mice in the group receiving the combined vaccine that were alive on day 15 remained alive and were apparently healthy thereafter and until the experiment was terminated. This experiment demonstrates that pooling of novopeptides can give increased protection over single peptide immunization.

e) Bioinformatic Analysis and Identification of Novopeptides

Candidate novopeptide nucleic acid sequences, expressed by cancerous cells and not by non-cancerous cells, can be identified and predicted by bioinformatics analysis comparing tumor database data with genomic data, and discloses the methods by which this was done. FS-novopeptide candidates were identified by bioinformatic analysis of frame shifts by comparing sequences obtained from tumor and normal EST library databases. Exact FS peptide sequences were then confirmed by DNA sequencing across the frame shift region and comparison to the non-cancerous reference sequence. It is noteworthy that several of the tumor-specific variants are not encoded at the DNA level but involve RNA splicing variants that are predominant in the tumors. Table 2a shows frame shift sequences predicted by the bioinformatic comparison and verified by DNA sequence analysis, and shows that these sequences are present in the indicated number of tumor EST's and not in non-cancerous EST's. Bioinformatic identification of possible novopeptides was performed as follows: the NCBI EST database was screened using information obtained from the NCI EST database to classify each NCBI EST's into one of three sets: tumor EST's, normal EST's and EST's for which there was insufficient information to classify as tumor or normal. The latter were discarded. Each human reference sequence in the NCBI database was then aligned with both the normal EST set and the tumor EST set using BLAST, and the number of frameshifted and unframeshifted hits of at least 100 base pairs and 85% sequence identity were counted. To identify candidates for further screening, an odds ratio was computed for each FS variant sequence arising from an indel of at least 10 base pairs. The odds ratio provides an indication of the relative expression of the FS variant in tumor and normal cells, as compared to the expression of the non-variant wild type sequence in tumor and normal cells. The ratio of FS variants to wild type in tumor cells (the "tumor cell variant ratio") was computed as the ratio of the number of sequence matches obtained upon search of the tumor EST databases for the FS variant sequence to the number of sequence matches obtained upon search of the tumor EST databases for the wild type sequence. The ratio of FS variants to wild type in normal cells (the "normal cell variant ratio") was computed as the ratio of the number of sequence matches obtained upon search of the normal EST databases for the FS variant sequence to the number of sequence matches obtained upon search of the normal EST databases for the wild type sequence. In computing this ratio, the former number was arbitrarily set to 1 if the number of matches were zero so as to avoid division by zero in computing the odds ratio; this approximation was deemed reasonable since the difference between zero and 1 is likely within the range of uncertainty associated with sequence alignment and the setting of alignment parameters. An odds ratio was computed as the ratio of the tumor cell variant ratio to the normal cell variant ratio, with FS variant sequences having a ratio above 2.0 being selected for further study. Table 2b shows six FS variant sequences for which RNA expression ratios of the FS variant in tumor vs. normal cells were determined, confirming the differential expression. Table 2c shows FS variants having high odds ratios, computed as described above; for CIAPIN1 and STYXL1, RNA expression ratios were measured to be 2.6× and 2.0×, respectively; RNA expression in tumor cells exceeding that in normal cells was confirmed by PCR and inspection of electrophoresis gel band intensities in BCL2L12 and DNPEP; and expression in tumor cells was verified by RNA extraction and sequencing for BCL2L12, DNPEP, and STYXL1. Table 2d shows FS variant sequences for which sequence matches were found in the tumor EST databases but for which, in the normal EST databases, no sequence matches were found for either the FS variant or the parent wild type sequence; this prevented computation of an odds ratio, but obviously non-expression in normal cells is a desirable characteristic. Note that very short FS variant sequences are nevertheless significant since, when expressed, they result in peptides representing fusions of the FS variant with the adjacent unshifted sequence. Table 2e shows FS variant sequences for which the number of sequence matches for the FS variant sequence against the normal EST databases was zero; this number was arbitrarily set at 1 for purposes of computing the odds ratio. RNA expression ratios measured for sequences C7orf24 and ZWILCH were 3.6× and 10.4×, respectively; RNA expression in tumor cells exceeding that in normal cells was confirmed by PCR and inspection of electrophoresis gel band intensities in DYRK4, HNRPUL1, MAP3K10, PPP4C, and RIPK2; and expression of the FS variant in tumor cells was confirmed by RNA extraction and sequencing for DYRK4, HNRPUL1, RIPK2, and ZWILCH. Table 2f shows FS variant sequences for which computed odds ratios were less than 2.0, but which are likely to be involved in tumorigenesis; RNA expression of BCL2L13 and DTYMK in tumor cells exceeding that in normal cells was confirmed by PCR and inspection of electrophoresis gel band intensities, and expression of DTYMK in tumor cells was confirmed by RNA extraction and sequencing. Table 2g shows genes for which FS variants were predicted and odds ratios computed as shown, but whose variants arise from indels of less than 10 bp, increasing the likelihood that the difference are due to a sequencing error.

TABLE 2a

| Gene | FS | EST analysis | Novopeptide Sequence | |
|---|---|---|---|---|
| RIPK2 | 154 bp deletion | Tumor: 6 of 16 Normal: 0 of 8 | ...HIHTPLLDrklnilmllgh* | SEQ ID NO: 9 |
| DTYMK | 91 bp deletion | Tumor: 3 of 86 Normal: 0 of 30 | ...SANRWEQVifp* | SEQ ID NO: 10 |
| 6-21 | 95 bp deletion | Tumor: NA Normal: NA | ...LLMCQCQLY Qpwmckeyyrll* | SEQ ID NO: 11 |
| DYRK4 | 61 bp deletion | Tumor: 4 of 10 Normal: 0 of 11 | ...EQLACIMEipkvflki* | SEQ ID NO: 12 |
| MTCH2 | 68 bp deletion | Tumor: 5 of 88 Normal: 0 of 63 | ...SYSQAVTGscwwmpsllpniyv ldrllvhatkrgeyeprk* | SEQ ID NO: 13 |
| FTH1 | 62 bp insertion | Tumor: 17 of 2157 Normal: 0 of 243 | ...ASYVYLSMivtatclwgslv* | SEQ ID NO: 14 |

TABLE 2b

| Accession | Gene Name | FS Peptides | RNA ratio |
|---|---|---|---|
| NM 006306 | SMC1L1 | GCCGIYCHEEPQREDSSI (SEQ ID NO: 15) | 98× |
| NM 015336 | HIP 14 | PWMCKKYYRLL (SEQ ID NO: 16) | 4× |
| XM 044434 | KIAA1458 | NPCQLLKPMVA (SEQ ID NO: 17) | 6.3× |
| NM_014342 | MTCH2 | SCWWMPSLLPNIYVLDRLL VHA TKRGEYEPRK (SEQ ID NO: 18) | 2.2× |
| NM 006833 | COPS6 | RGPL (SEQ ID NO: 19) | 9.75× |
| NM 000314 | PTEN | | 41× |

TABLE 2c

| Accession ID | Gene name | FS peptide | Odds Ratio |
|---|---|---|---|
| NM_001745 | CAMLG | VHICSISYFTTCVHGIIQIFSQE (SEQ ID NO: 20) | 2.50 |
| NM_001014438 | CARS | GSVHTSRWEKGDWLLWANRL (SEQ ID NO: 21) | 2.86 |

TABLE 2c-continued

| Accession ID | Gene name | FS peptide | Odds Ratio |
|---|---|---|---|
| NM_020313 | CIAPIN1 | SAHKESSFDIICQV (SEQ ID NO: 22) | 2.22 |
| NM_006716 | DBF4 | SS | 4.09 |
| NM_017996 | DET1 | TRHLLKSMSTRARQQRTYCRDTKEKSCPMAMTSGQ (SEQ ID NO: 23) | 2.67 |
| NM_012100 | DNPEP | GWLQ (SEQ ID NO: 24) | 2.36 |
| NM_006705 | GADD45G | LRGQGG (SEQ ID NO: 25) | 2.38 |
| NM_000849 | GSTM3 | LLTMIEANGWM (SEQ ID NO: 26) | 3.82 |
| NM_201612 | IKIP | CGRNLKLSWNN (SEQ ID NO: 27) | 15.43 |
| NM_001012634 | IL32 | HQAIERFYDKMLQNQDVDR (SEQ ID NO: 28) | 4.63 |
| NM_015416 | LETMD1 | ESLEPGHASHILPASSLVETSFEDSYNCDSPTGQGFGKAGDWPADCSGSKIGLLSPWPEFYAYW (SEQ ID NO: 29) | 3.08 |
| NM_002405 | MFNG | GPTLWSPTAPRNTATQLCPARWLLSSTPSWPVGLGGSAMWTMTTM (SEQ ID NO: 30) | 2.47 |
| NM_198883 | MTX1 | KYNADYDLSARQGADTLAFMSLLEEKLLPVL (SEQ ID NO: 31) | 3.08 |
| NM_152298, NM_002482 | NASP | SNH | 3.65 |
| NM_006985 | NPIP | SRSQLGMAVIFLFTPR (SEQ ID NO: 32) | 2.11 |
| NM_153681 | PIGP | KNLKGSRVC (SEQ ID NO: 33) | 3.69 |
| NM_018845 | RAG1AP1 | KLR | 2.29 |
| NM_015014 | RBM34 | GKRSSEC (SEQ ID NO: 34) | 11.08 |
| NM_183400 | RNF14 | AICSMQALRQPMGRTPWQRGPVCLDAIS (SEQ ID NO: 35) | 11.73 |
| NM_016211 | SEC31A | PSEWLE (SEQ ID NO: 36) | 2.33 |
| NM_001009939 | SEPT5 | VENQAHCDFVKLRNMLIRTHMHDLKDVTCDVHYENYRAHCIQQMTSKLTQDSRMESPIPILPLPTPDAET (SEQ ID NO: 37) | 2.63 |
| NM_005827 | SLC35B1 | WWIVPGAGSMLPVLSPIWVPWSPAIQHYSLSTTQLRSLVNPASQSQSCSLG (SEQ ID NO: 38) | 9.45 |
| NM_003473 | STAM | GVILKYVKN (SEQ ID NO: 39) | 2.14 |
| NM_003763 | STX16 | A | 2.70 |
| NM_016086 | STYXL1 | GTGCISAIPH (SEQ ID NO: 40) | 7.27 |
| NM_032026 | TATDN1 | VYDYRWKSTRQ (SEQ ID NO: 41) | 3.63 |
| NM_001001563 | TIMM50 | DHRAHQPLPSPRPSAGTVLPATLHARFGAHRRPLAS (SEQ ID NO: 42) | 2.92 |

TABLE 2c-continued

| Accession ID | Gene name | FS peptide | Odds Ratio |
|---|---|---|---|
| NM_100486 | WAC | MEDKHSSDASSLLPQNILSQTSRHNDRDYRLPRAETHSS STPVQHPIKPVVHPTATPSTVPSSPFTLQSDHQPKKSFD ANGASTLSKLPTPTSSVPAQKTERK (SEQ ID NO: 43) | 2.70 |
| NM_024061 | ZNF655 | GHTSPPSHHPDS (SEQ ID NO: 44) | 2.09 |

TABLE 2d

| Accession ID | Gene Name | FS Peptides |
|---|---|---|
| NM_212533 NM_001606 | ABCA2 | E |
| NM_172027 | ABTB1 | VLCLLVWARGAGTLPSGQWSPLRGQHLRW (SEQ ID NO: 45) |
| NM_001033055 | AIPL1 | VIFHFRTMKCDEERTVIDDSRQVGQPMHIIIGNMFKLEVWEILL TSM RVH EVAEFWCDTI (SEQ ID NO: 46) |
| NM_001707 | BCL7B | GQSLAMLSRLVVNSWPQAVPRP (SEQ ID NO: 47) |
| NM_004328 | BCS1L | LES |
| XM_043653 | BEXL1 | PLTEASYVNLPTIALCNTDSPLRYVDIAIPCNNKGAHS (SEQ ID NO: 48) |
| NM_139343 | BIN1 | LRKGPPVPPPPKHTPSKEVKQEQILSLFEDTFVPEISVTTPSQPAEAS EVAGGTQPAAGAQEPGETAASEAAS (SEQ ID NO: 49) |
| NM_015412 | C3orf17 | G |
| NM_001009186 | CCT6A | QIQHPTASLIAKVATAQDDITGDGTTSNVLIIGELLKQADLYISE (SEQ ID NO: 50) |
| NM_134445 | CD99L2 | QPWDHTNNHHNK (SEQ ID NO: 51) |
| NM_033488 | CDC2L1 | SVCTSPNDERGLQRQSESQPLESQPASAAGAVRVGRRPEASKRRE NGRKGPAVRLTGHQRQREEDQLGRVLVSRIRLRF (SEQ ID NO: 52) |
| NM_001005271 NM_001005273 | CHD3 | EMGEEGGGRTGNH (SEQ ID NO: 53) |
| NM_017828 | COMMD4 | VRPSTVSMANPCPVNCSSWGCPKSTRPACAAVMRRSKAPCRSTC GSAAYA (SEQ ID NO: 54) |
| NM_032179 | CPSF3L | SCLD (SEQ ID NO: 55) |
| NM_004715 | CTDP1 | KWTTSLEKATTAT ARRGGLRSRRRSPSPGSQGPAGSGRSGHLRPARGARQGAGGPEAT RGS (SEQ ID NO: 56) |
| NM_001930 | DHPS | AERGRLRCLHQHSPGV (SEQ ID NO: 57) |
| NM_182908 | DHRS2 | FHGNESLWKN FKEHHQLQRIGESEDCAGIVSFLCSPDASYVNGENIAVAGYSTRL (SEQ ID NO: 58) |
| NM_021931 | DHX35 | HDLSSQRLQGE (SEQ ID NO: 59) |
| NM_001009894 | DKFZp434 N2030 | ISHTFGLD (SEQ ID NO: 60) |

TABLE 2d-continued

| Accession ID | Gene Name | FS Peptides |
|---|---|---|
| NM_032378 | EEF1D | AQAPGPPAAPAETTVSSSSGLPVWKWRTRVCVAWYRSCSRPSPS WRPG (SEQ ID NO: 61) |
| NM_024311 | ET | RRVTEEQCLLP (SEQ ID NO: 62) |
| NM_023109 | FGFR1 | CIHRDLAARNVLVTEDNVMKIADFGLARDIHHIDYY (SEQ ID NO: 63) |
| NM_001001662 | FLJ16636 | KDVGEPSLFPLA (SEQ ID NO: 64) |
| NM_024578 | FLJ22709 | VSLTGRGSPGRASRQKI (SEQ ID NO: 65) |
| NM_005087 NM_001013439 | FXR1 | GKRCD (SEQ ID NO: 66) |
| NM_002106 | H2AFZ | VGI |
| NM_014056 | HIGD1A | VFGDSPALSPRLECSGRISAHCSLCLLGSSDSPTSAS (SEQ ID NO: 67) |
| NM_003529 | HIST1 H3A | R |
| NM_153490 | KRT13 | GPGPSR (SEQ ID NO: 68) |
| NM_019016 | KRT24 | ATPTWK (SEQ ID NO: 69) |
| NM_015848 | KRT2B | TLLQEQGTKTVRQNLEPLFEQYINNLRRQLDNIVGERGRLDS (SEQ ID NO: 70) |
| NM_002272 | KRT4 | ESWYQTKYEELQITAGRHGDDLRNTKQEIAEINRMIQRLRSEIDHV KKQCANLQAAIADAEQRGEMALKDAKNKLE (SEQ ID NO: 71) |
| NM_153486 | LDHD | GRRLR (SEQ ID NO: 72) |
| XM_060417 | LOCI 27295 | LARMCVPTLLLTNLRARLVRKREELSNVLAAMKKATAKKD (SEQ ID NO: 73) |
| XM_497978 | LOC132391 | RVRHGVRGPGHRDSRGSGRNGRHPEREGDHAKPERPPGLLPGQQ (SEQ ID NO: 74) |
| XM_211339 | LOC284120 | LLSFCCPGWSSVA (SEQ ID NO: 75) |
| XM_208312 | LOC284120 | LDDSIWKLVSPGSALPRIFGLSPESLSADH (SEQ ID NO: 76) |
| XM_293903 | LOC284120 | IVEERKMHWSPRTWSLGNQFMERRESRFRKEMTKLSTE (SEQ ID NO: 77) |
| XM_370672 | LOC284120 | TVKHPVCV (SEQ ID NO: 78) |
| XM_495875 | LOC282120 | FHVNHVKRSRVPLSVGDHTNSS (SEQ ID NO: 79) |
| XM_372840 | LOC391209 | LARMCVPTLLLTNLRARLVRKREELSNVLAAMKKATAKKD (SEQ ID NO: 80) |
| XM_497922 | LOC391538 | RCVLKIGEHTPSALAIMENAKCSGPLCQYLPAEWHCAHRGA (SEQ ID NO: 81) |
| XM_496658 | LOC440976 | GGGGRAERPAGLAGVQGQTGWVSVLKPPALLPQLRSKVKRLIRF (SEQ ID NO: 82) |
| XM_497335 | LOC441632 | AKQVLLGRKWRCEGINISGNFYTKQVEVPRFPPQADEHQLLPRLL PLGPQPHLLADRARYAAPQDQARPGRSGPPQGV (SEQ ID NO: 83) |

TABLE 2d-continued

| Accession ID | Gene Name | FS Peptides |
|---|---|---|
| XM_497347 | LOC441641 | GNFYRNKLKYLAFLRKRMNTNPSRGPYHFRAPSRIFWRTVRGML PHKTKRGQAALDRLKVFDGIPPPTT (SEQ ID NO: 84) |
| XM_497605 | LOC441836 | VGDEAQSKRGILTLKYPIEHGIVTTPSTTSCAWPRRSTRCC (SEQ ID NO: 85) |
| XM_029323 | LOC90133 | QAPRL (SEQ ID NO: 86) |
| NM_138779 | LOC93081 | GTCWRKWHRKCKLPIKSTGLRRQIIPWQ (SEQ ID NO: 87) |
| NM_002383 | MAZ | GFTTAAYLRIHAVKDHGLQAPRADRILCKLCSVHCKTPAQLAGH MQTHLGGAAPPVPGDAPQPQPTC (SEQ ID NO: 88) |
| NM_174923 | MGC31967 | REEMSTQWLPTYPIPPSCHKFPKNSQNHCSPHL (SEQ ID NO: 89) |
| NM_182523 | MGC61571 | YFLSSIRFISTF (SEQ ID NO: 90) |
| NM_025259 | MSH5 | RNPQQMPL (SEQ ID NO: 91) |
| NM_002485 | NBN | V |
| NM_001001716 | NFKBIB | RHCTWL (SEQ ID NO: 92) |
| NM_020729 | ODF2L | WRIFLH (SEQ ID NO: 93) |
| NM_001007157 | PHF14 | GLADS (SEQ ID NO: 94) |
| NM_015937 | PIGT | EFSSQLWTLKEGAEVAPGQ (SEQ ID NO: 95) |
| NM_007221 | PMF1 | SPLLHWDGSAWSPPALWWTVCETGLQLGGVQVTTGEEGGNL (SEQ ID NO: 96) |
| NM_001017431 | RBM3 | VVVVKDRETQRSRGFGFITFTNPDLWMVVRSVWIMQASLLGEPEEV ALGPMGVVAATL (SEQ ID NO: 97) |
| NM_015725 | RDH8 | LFLWLSSQALTLRPCTTSGTSISQPPGSCFAPWDRTHRTWFRPLST SSARLDHPCADRPTSATRR (SEQ ID NO: 98) |
| NM_194452 | RNF121 | IW |
| NM_001005 | RPS3 | KLVGNSQKECGVS (SEQ ID NO: 99) |
| NM_058192 | RPUSD1 | GVSGVGGVLVVTEGKLRHRATKLMLGHPEHQGRAGNKHSCVLNS TPCSLSASHLTQGPCWLLTDSLGVWLAAILQDRAPPWPCPHQW (SEQ ID NO: 100) |
| NM_207521 | RTN4 | MDLKEQPGNTISAGQEDFPSVLLETAASL (SEQ ID NO: 101) |
| NM_173073 | SLC35C2 | RAALVLVVLLIAGGLFMFTYK (SEQ ID NO: 102) |
| NM_130849 | SLC39A4 | VRMARGGAALGRELSRGAEQGR (SEQ ID NO: 103) |
| NM_003096 | SNRPG | KKLNGGRHVQGILRGFDPFMNLVIDECVEMATSGQQNNIGMVVIR GNSIIMLEALERV (SEQ ID NO: 104) |
| NM_014748 | SNX17 | VGLAPLP (SEQ ID NO: 105) |

TABLE 2d-continued

| Accession ID | Gene Name | FS Peptides |
|---|---|---|
| NM_013403 | STRN4 | MLLRRGTPSSPCARTTTAFVPWPSTTASRLCSPPPRTARSSSGTC RRRSRPRRMRR (SEQ ID NO: 106) |
| NM_006521 | TFE3 | RGLQDPCHVVIFFIEGLAANAGPGAGAGEA (SEQ ID NO: 107) |
| NM_003299 | TRA1 | AWTRFAMRA (SEQ ID NO: 108) |
| NM_176880 | TRA 16 | VHRALRLSTRL (SEQ ID NO: 109) |
| NM_173500 | TTBK2 | GTKTCEAEPGAVVRAVHQQPQEAAGQHRGGTGSSGLGAEKHAGP GGGPQEQTMRMKSTSAQQQRMNL (SEQ ID NO: 110) |
| NM_018299 | UBE2W | SCLLVKIFLFILMFIAMVISVYPF (SEQ ID NO: 111) |
| NM_018206 | VPS 3 5 | SLIIIKRYGHF (SEQ ID NO: 112) |
| NM_001006612 NM_001006614 | WBP5 | A |
| NM_017528 | WBSCR22 | K |
| NM_001033518 NM_001033519 | WIPI-2 | TRYGRCVHCREIVLQQPSGHRQP (SEQ ID NO: 113) |
| XM_374912 | XRRA 1 | EDRKRGCCPTSSSLPISLRVRLS (SEQ ID NO: 114) |

TABLE 2e

| Accession ID | Gene name | FS peptides | Odds Ratio |
|---|---|---|---|
| NM_001033054 | AIPL1 | HTGVYPILSRSLRQMAQGKDPTEWHVHTCGLANMFAY HTLGYEDLDELQKEPQPLVFVIELLQ (SEQ ID NO: 115) | 3.00 |
| NM_005787 | ALG3 | TQRLTGRPTWPR (SEQ ID NO: 116) | 2.79 |
| NM_001002857 | ANXA2 | VWMRSPLSTF (SEQ ID NO: 117) | 4.12 |
| NM_175073 | APTX | SLRKRQRTLAWKHTGRERDQATVIL (SEQ ID NO: 118) | 4.92 |
| NM_005174 | ATP5C1 | CHQETKVHQKHPENYQVYENGSGSKICPS (SEQ ID NO: 119) | 2.62 |
| NM_001003785 | ATP5H | IFFFFGIHLGSIFILWHGNLQRIK (SEQ ID NO: 120) | 2.57 |
| NM_004047 | ATP6V0B | GS | 2.13 |
| NM_080598 | BAT1 | GCCFFWWSVYQEG (SEQ ID NO: 121) | 2.12 |
| NM_013980 | BNIP1 | SNQASWRKANLTCKIAIDNLEKAELLQGGDLLRQRPPK RAWPRHPVPSLRASWGSAG (SEQ ID NO: 122) | 5.33 |
| NM_018045 | BSDC1 | G | 2.38 |
| NM_001032363 | C1orf151 | ESW | 4.47 |
| NM_014145 | C20orf30 | APSCCQATSAKGGQTGPFQC (SEQ ID NO: 123) | 6.25 |

TABLE 2e-continued

| Accession ID | Gene name | FS peptides | Odds Ratio |
|---|---|---|---|
| NM_004649 | C21orf33 | DPGAPEPWRG (SEQ ID NO: 124) | 2.31 |
| NM_005768 | C3F | AERE (SEQ ID NO: 125) | 3.00 |
| NM_024051 | C7orf24 | ARRG (SEQ ID NO: 126) | 5.00 |
| NM_018491 | CBWD1 | VIQRLLC (SEQ ID NO: 127) | 3.04 |
| NM_018246 | CCDC25 | GKNCDSGEESK (SEQ ID NO: 128) | 3.00 |
| NM_001782 | CD72 | RPRG (SEQ ID NO: 129) | 5.83 |
| NM_006319 | CDIPT | AACWTLSMDTLLALLIKEPGLGPCWTC (SEQ ID NO: 130) | 2.11 |
| NM_024300 | CHCHD7 | CRSCSTF (SEQ ID NO: 131) | 6.55 |
| NM_001009566 | CLSTN1 | GERRE (SEQ ID NO: 132) | 3.79 |
| NM_199442 | COPE | RDSIVAELDREMSRSVDVTNTTFLLMAASIYLHDQNPDAALRALHQGDSLE (SEQ ID NO: 133) | 3.30 |
| NM_032589 | DSCR8 | LQTLEIKKVLE (SEQ ID NO: 134) | 7.00 |
| NM_020185 | DUSP22 | DKTFQRKY (SEQ ID NO: 135) | 5.00 |
| NM_003845 | DYRK4 | IPKVFLKI (SEQ ID NO: 136) | 7.33 |
| NM_001967 | EIF4A2 | DPKGNSGTWRLYGSHLSCLHWWNKCSK (SEQ ID NO: 137) | 5.62 |
| NM_019002 | ETAA16 | KFKFECNFRSYEYRNYYL (SEQ ID NO: 138) | 3.00 |
| NM_032231 | FAM96A | VGNLHF (SEQ ID NO: 139) | 4.26 |
| NM_005687 | FARSLB | NI | 5.28 |
| NM_001031704 | FLJ20211 | GCQPDHGAGAWAACVP (SEQ ID NO: 140) | 2.00 |
| NM_013393 | FTSJ2 | IPALLLASCLG (SEQ ID NO: 141) | 2.22 |
| NM_203504 | G3BP2 | EL | 2.82 |
| NM_004127 | GPS1 | SCRTHPTPSLRAWSPQPWTRPGWRPRGRRRC (SEQ ID NO: 142) | 6.31 |
| NM_012203 | GRHPR | AVRWSSGTRMSPSLPRS (SEQ ID NO: 143) | 17.27 |
| NM_147149 | GSTM4 | LPYLIDGAHKITQSNAILCYIARKHNLCGETEEEKIRVDILENQAMDVSNQLARVCYSPDFEKL (SEQ ID NO: 144) | 2.41 |
| NM_000853 | GSTT1 | VWPSCST (SEQ ID NO: 145) | 6.32 |
| NM_145871 | GSTZ1 | LAIIEYLEEMRPTPRLLPQDPKKRASVRMISDLIAGGIQPLQ (SEQ ID NO: 146) | 7.31 |

TABLE 2e-continued

| Accession ID | Gene name | FS peptides | Odds Ratio |
|---|---|---|---|
| NM_000858 | GUK1 | GR | 2.68 |
| NM_000187 | HGD | GTA | 3.33 |
| NM_003537 | HIST1H3B | RW | 2.15 |
| NM_001002032 | HN1 | GEGDIHENVDTDLPGSLGQSEEKPVPAAPVPSPVAPAPV PSRRNPPGGKSSLVLG (SEQ ID NO: 147) | 45.29 |
| NM_144733 | HNRPUL1 | MPWTILPGRTNSTIPKSSNKKTSQATRGDHWKWSSSRPI VQK (SEQ ID NO: 148) | 2.40 |
| NM_016371 | HSD17B7 | MIKKWLYVICVEDHVSEIRLYISKCWDHA (SEQ ID NO: 149) | 2.77 |
| NM_144981 | IMMP1L | CQWVMFG (SEQ ID NO: 150) | 2.00 |
| NM_024710 | ISOC2 | EHDPGPPRPGAAGPCGGGRLLLTQPGGPAGGSGPHETE WCLPLHQRRAHSAACGRCRPPPVQGDPETHQGARPRQ RTAGPLPRPELPPPL (SEQ ID NO: 151) | 8.85 |
| NM_005886 | KATNB1 | A | 3.50 |
| XM_371877 | K1AA0960 | RKAQRYTGQ (SEQ ID NO: 152) | 5.00 |
| NM_138787 | LOC119710 | DLLLLPGEVEQDVSTSIPSCIPFVAQPPTCEVKPKPS VKR MDKQTEEILGDEVQLFSLDEEFDYDNVMLTSKFSPAEIE NIKELCKQQRKDTSPDLEKSCD (SEQ ID NO: 153) | 5.25 |
| XM_059341 | LOC129293 | GSSLL (SEQ ID NO: 154) | 2.50 |
| NM_001031744 | LOC158160 | MIKKWLYVICVEDHVSEIRPYISKCWDHA (SEQ ID NO: 155) | 3.64 |
| NM_174928 | LOC221143 | VPSWKNRQQNSLE (SEQ ID NO: 156) | 4.44 |
| XM_290671 | LOC339047 | CKTWHSAWV (SEQ ID NO: 157) | 4.36 |
| NM_001005920 | LOC339123 | VSACPSVPGHSRPCWARPLSPLPAPAEVPGPVLPRQVAG FVWGQSGPAEHRQHLLLPQSGLALPGVCGAAAPPGPHL PGQ (SEQ ID NO: 158) | 6.67 |
| XM_292085 | LOC341457 | MPSTASPW AASPLSCLQTSFQRQQETFML (SEQ ID NO: 159) | 7.66 |
| XM_495885 | LOC440055 | YVYQSQYCGFLQPEQNCHPREEGMEFMVLAQKF (SEQ ID NO: 160) | 6.32 |
| XM_352159 | LOC440341 | CKTWHSAWV (SEQ ID NO: 161) | 2.55 |
| NM_002446 | MAP3K10 | RMLGPRPPRARFR (SEQ ID NO: 162) | 4.80 |
| NM_181514 | MRPL21 | G | 2.86 |
| NM_145330 | MRPL33 | KNILVRMVSEAGTGFCFNTKRNRLREKLTLLHYDPVVK QRVLFVEKKKIRSL (SEQ ID NO: 163) | 17.50 |
| NM_012333 | MYCBP | SVGSLI (SEQ ID NO: 164) | 3.78 |
| NM_012225 | NUBP2 | R | 7.14 |
| NM_000430 | PAFAH1B1 | MKN | 2.17 |

TABLE 2e-continued

| Accession ID | Gene name | FS peptides | Odds Ratio |
|---|---|---|---|
| NM_001003891 | PCQAP | RGCHEESWCGTQ (SEQ ID NO: 165) | 5.60 |
| NM_020992 | PDL1M1 | I | 2.77 |
| NM_002677 | PMP2 | EVGVGLPPGKWLAWPNLT (SEQ ID NO: 166) | 4.50 |
| NM_174930 | PMS2L5 | LFQL (SEQ ID NO: 167) | 2.12 |
| NM_006243 | PPP2R5A | KLYCSF (SEQ ID NO: 168) | 2.00 |
| NM_180977 | PPP2R5D | LFLIH (SEQ ID NO: 169) | 3.11 |
| NM_002720 | PPP4C | RCAATSMDNSMTSKSCSE (SEQ ID NO: 170) | 3.81 |
| NM_032864 | PRPF38A | RNAMY (SEQ ID NO: 171) | 4.44 |
| NM_002767 | PRPSAP2 | ENKSTNSRVCEGKRCFHHPNCFEGREHHHHGAPDHGVCM (SEQ ID NO: 172) | 7.38 |
| NM_021222 | PRUNE | K | 2.77 |
| NM_003579 | RAD54L | DA | 2.43 |
| NM_005493 | RANBP9 | AKFVSYCGASNTRRSGRCQFWATSFRV (SEQ ID NO: 173) | 3.00 |
| NM_006743 | RBM3 | VSGWSSDPCGSCRQVCSGNQRRWLWGPWAWSQLL (SEQ ID NO: 174) | 3.81 |
| NM_181471 | RFC2 | GH | 3.28 |
| NM_003821 | RIPK2 | RKLNILMLLGH (SEQ ID NO: 175) | 4.80 |
| NM_001016 | RPS12 | YVYQSQYCGFLQPEQNCHPREEGMEFMVLAQKF (SEQ ID NO: 176) | 6.21 |
| NM_007008 | RTN4 | GFVFAPR (SEQ ID NO: 177) | 6.68 |
| NM_005888 | SLC25A3 | YSCEFGSAKYYALCGFGGVLSCGLTHTAVVPLDLV (SEQ ID NO: 178) | 2.38 |
| NM_003136 | SRP54 | VCY | 3.38 |
| NM_139276 | STAT3 | FIDAVWK (SEQ ID NO: 179) | 2.31 |
| NM_003195 | TCEA2 | RLSPSVSHSICRRQQFGV (SEQ ID NO: 180) | 4.00 |
| NM_144582 | TEX261 | D | 2.14 |
| NM_005727 | TSPAN1 | VCETQLHRLMTKSPLAFDTRPWDSQTLLWTPLGSGFCLTFPGGGLGQGGHEGLSLPKTQTPVPHSVLLHPPPHLHC (SEQ ID NO: 181) | 4.91 |
| NM_018943 | TUBA8 | MRECISVHVGQAGV (SEQ ID NO: 182) | 2.85 |
| NM_145345 | UBXD5 | EDEVDMLSDGCGSEERRSQSLPAMAA (SEQ ID NO: 183) | 3.67 |
| NM_005153 | USP10 | DKNIRELSLVSMKSLNPVTLCREPPATVFQAH (SEQ ID NO: 184) | 2.07 |

TABLE 2e-continued

| Accession ID | Gene name | FS peptides | Odds Ratio |
|---|---|---|---|
| NM_022170 | WBSCR1 | GFRDDFLGGRGGSRPGDRRTGPPMGSRFRDGPPLRGSN MDFREPTEEERAQRPRLQLKPRTVATPLNQVANPNSAIF GGARPREEVVQKEQE (SEQ ID NO: 185) | 2.55 |
| NM_024699 | ZFAND1 | IFFHLCVMIVQEYF (SEQ ID NO: 186) | 2.81 |
| NM_017975 | ZWILCH | CPAEIK (SEQ ID NO: 187) | 4.42 |

TABLE 2f

| Accession ID | Gene Name | Function | FS Peptides |
|---|---|---|---|
| NM_015367 | BCL2L13 | Apoptosis | QFWCLWFCYDKCFWN (SEQ ID NO: 188) |
| NM_012145 | DTYMK | Kinase | IFP |
| NM_152255 | PSMA7 | ETC | RYTQSNGRRPFGISALIVGFDFDGTPRLYQTDPSGTYHAW KANAIGRGAKSVREFLEKNYTDEAIETDDLTIKLVIKALLE VVQSGGKNIELAVMRRDQSLKILNPEEIEKYVAEIEKEKEE NEKKKQKKAS (SEQ ID NO: 189) |
| NM_024572 | GALNT14 | ETC | KYGPSHTPSRSSRRSCACQSSPCSLAPQWFLSFARMEMTD SNGPKLVPTSST (SEQ ID NO: 190) |
| NM_003089 | SNRP70 | ETC | RPGPGP (SEQ ID NO: 191) |

TABLE 2g

| Accession | Definition | Odds Ratio | FS peptides |
|---|---|---|---|
| XP_060328.1-11 | PREDICTED: similar to 60S acidic | 53.19148936 | VSELACIYSASFCTTMR (SEQ ID NO: 192) |
| NP_001772.1-67 | CD69 antigen (p60, early T-cell) | 48 | VQANTHSQCHQTAMFL HALRTGLATRGNATLF LL (SEQ ID NO: 193) |
| NP_001022.1-13 | ribosomal protein S28 [Homo sapiens] | 41.66666667 | SPRSWAGPVLRDSARC AWNSWTRADPSSAM (SEQ ID NO: 194) |
| XP_060328.1-51 | PREDICTED: similar to 60S acidic ribosomal protein P2 | 33.65384615 | ATSTLGASSAM (SEQ ID NO: 195) |
| NP_000995.1-62 | [Homo sapiens] | 22.47191011 | VLASLPVYLLVGL (SEQ ID NO: 196) |
| NP_001025172.1-16 | ribosomal protein S29 isoform 2 | 20.69536424 | VLALVVSVQTGTV (SEQ ID NO: 197) |
| XP_497649.1-13 | PREDICTED: similar to Cofilin, | 18.675 | VSDGVIKGVQRHEGA (SEQ ID NO: 198) |
| NP_000080.2-10 80 | alpha 2 type I collagen (Homo | 16 | VHQGPCWPPWSPWPS WTSRCKRWWL (SEQ ID NO: 199) |

TABLE 2g-continued

| Accession | Definition | Odds Ratio | FS peptides |
|---|---|---|---|
| XP_170597.1~16 | PREDICTED: similar to A TP synthase, H+ | 14.36538462 | WAASPLSCLQTRSQRQ QKIFVL (SEQ ID NO: 200) |
| NP_005167.1-74 | transporting, murine mamary | 14.14285714 | LGASSLVMPGTLL (SEQ ID NO: 201) |
| NP_001559.1-45 | tumor integration | 13.52173913 | WTLVIPTW (SEQ ID NO: 202) |
| NP_001002032.1-20 | hematological and neurological | 12.8 | CGLQVVDPIFH (SEQ ID NO: 203) |
| NP_722550.1-28 6 | reticulon 4 isoform B [Homo | 12.5 | LQVDVGIYLCWCLV (SEQ ID NO: 204) |
| NP_001017430.1-47 | RNA binding motifprotein 3 calnexin precursor | 12.48920863 | VLVSSPSPTQSMLQLP (SEQ ID NO: 205) |
| NP_001737.1-18 | [Homo sapiens] | 11.66666667 | MLRLMMDMMMM (SEQ ID NO: 206) |
| NP_008939.1-11 2 | reticulon 4 isoform C [Homo | 10.71428571 | LQVDVGIYLCWCLV (SEQ ID NO: 207) |
| NP_001017430.1-48 | RNA binding motif protein 3 | 10.70503597 | LVSSPSPTQSMLQLP (SEQ ID NO: 208) |
| NP_954654.1-14 4 | Nucleophosmin 1 isoform 2 [Homo | 10.28337875 | LEVVARFHRKK (SEQ ID NO: 209) |
| NP_997001.1-48 | general transcription factor IIH, | 10.2 | WLMSSRSEWVN (SEQ ID NO: 210) |
| NP_002801.1-36 | proteasome 26S non-ATPase subunit 4 | 10.11570248 | VIQRPAATLRTTW ALSHWLMTVKC (SEQ ID NO: 211) |
| NP_004252.2-93 | 15 kDa selenoprotein isoform 1 | 10.0952381 | VDENWEGSLKSKLC (SEQ ID NO: 212) |
| XP_371019.1-12 | PREDICTED: similar to ribosomal | 10 | CEYSTPTSMGGGK (SEQ ID NO: 213) | f) RNA Expression

FIG. 7 illustrates an example of a method for assessing the likely utility of a predicted candidate novopeptide as a cancer vaccine component by comparing the RNA expression level of the novopeptide in tumor cells with that in non-cancerous cells. FIG. 7a demonstrates amplification of a FS variant in BCL2L13 cDNA from three different human tumor cell lines, but not cDNA obtained from normal tissue. PCR primers were designed such that they flanked the BCL2L13 FS region and amplify a FS of 253 bp indicated by the arrow. The left half of the figure is amplification of three different human tumor cDNA preparations. Lane labels in FIG. 7 are as follows. Lane M, 100 bp molecular weight marker; Lane 1, MCF-7 human breast cancer cell line; SW480 human colon cancer cell line; DU-145, human prostate cancer cell line; Lane TA beta actin from SW480 cell line. Right side of gel: Lane NA, beta actin from normal colon; Lane NL, normal lung; NB, normal breast; NC normal colon.

FIGS. 7b and 7c show two additional examples of amplification of cDNA from frameshifted genes called STYXL1 and HNRPUL1. The agarose gel shows a frameshift encoding a novopeptide present in tumor cells, but not present in cDNA from normal lung, breast and colon. PCR was performed as in 7a, but with primers that flank the predicted frameshifts. Arrows mark the FS bands in each figure. Lanes are the same as FIG. 7a.

Quantitative PCR measurement showed over-expression of another frameshift variant, SMC-I. cDNA from four fresh human pancreas tumor samples were tested for relative expression of SMC-I FS using PCR primers specific for the FS in the SMC-I gene. Levels of SMC-I FS cDNA were compared to SMC-I cDNA amplified from normal pancreas from the same patient. Table 3 shows that three of four pancreas tumors overexpress FS SMC-I, compared to the normal wild type sequence.

TABLE 3

| | Relative Expression | |
|---|---|---|
| Sample | FS | WT |
| Panc-C | 2.69 | 0.094 |
| Panc-E | 30.7 | 0.852 |
| Panc-F | 1.15 | 0.26 |
| Panc-G | 0.512 | 0.696 | g) Identification of Novopeptides by Mass Spectrometry and Identification of Subsequences Likely to be Displayed in MHC Herein it is shown that novopeptides actually expressed by tumor cells can be identified via mass spectrometry and discloses a method for doing so, and also illustrates and discloses a method for identifying subsequences likely to be displayed in MHC. Peptides were eluted from the surface of tumor cells by exposure to 100 mM citric acid for 30 seconds, or phosphate buffered saline for 4 hours, or peptides were competed from cell surface HLA molecules with a biotinylated peptide having high affinity for the HLA molecule of interest. A database of frame shifted peptide sequences was constructed from the sequences predicted bioinformatically as described above, to enable the use of LC-MS/MS to identify novopeptides actually present in the eluted sample by analysis using. The peptide sequence database was used to search spectra obtained from LC-MS/MS, using Spectrum Mill, for peptides eluted from MCF-7 breast tumor cells HLA-A*0201, -B* 18/44 and -Cw*05. The HLA types were determined for the tumor cells of interest as described above. Unexpectedly, peptides longer than 8-10 amino acids were identified from LC-MS/MS analysis of the elutions that matched some sequences in the FS database. These longer peptides have been analyzed using MHC class I binding algorithms, BIMAS and SYPPEITHI, to identify preferred 9-mer sequences that are capable of binding multiple HLA class I molecules as shown below in Table 4a-4e. The algorithms use different methods of scoring peptides for binding. Sometimes the algorithms are complementary, but often they are not. BEvIAS values over 150 and SYFPEITHI values over 20 have the best chance for peptides binding to MHC intracellularly and being transported to the cell surface.

TABLE 4a

Parent sequence #1 eluted from MCF-7 tumor cells: VIKSLQSWYLRLVI (SEQ ID NO: 225)

| HLA | SEQ | BIMASS | SYFPEITHI |
|---|---|---|---|
| A*0201 | SLQSWYLRL (SEQ ID NO: 214) | 32 | 23 |
| A*1101 | KSLQSWYLR (SEQ ID NO: 215) | .036 | 21 |

TABLE 4b

Parent sequence #2 eluted from MCF-7 tumor cells: FLSPMSGLLSTTQQSACTGIHRTS (SEQ ID NO: 226); Table 4b discloses the "A*6801" sequence as SEQ ID NO: 217.

| HLA | SEQ | BIMASS | SYFPEITHI |
|---|---|---|---|
| A*0201 | FLSPMSGLL (SEQ ID NO: 216) | 12.7 | 23 |
| A*1101 | QSACTGIHR (SEQ ID NO: 217) | 0.008 | 23 |
| A*6801 | QSACTGIHR | 45 | 20 |

TABLE 4c

Parent sequence #3 eluted from MCF-7 tumor cells: PSPQETEFPGPGWRPILDVGKIS (SEQ ID NO: 227); Table 4c discloses the "B*5102" sequence as SEQ ID NO: 222.

| HLA | SEQ | BIMASS | SYFPEITHI |
|---|---|---|---|
| A*0201 | GVVRPILDV (SEQ ID NO: 218) | 13 | 21 |

TABLE 4c-continued

Parent sequence #3 eluted from MCF-7 tumor cells: PSPQETEFPGPGWRPILDVGKIS (SEQ ID NO: 227); Table 4c discloses the "B*5102" sequence as SEQ ID NO: 222.

| HLA | SEQ | BIMASS | SYFPEITHI |
|---|---|---|---|
| A*1301 | VVRPILDVG (SEQ ID NO: 219) | 0.405 | 20 |
| B*0702 | GPGVVRPIL (SEQ ID NO: 220) | 120 | 23 |
| B*2705 | VRPILDVGK (SEQ ID NO: 221) | 2000 | 23 |
| B*5101 | RPILDVGKI (SEQ ID NO: 222) | 200 | 24 |
| B*5102 | RPILDVGKI | 2640 | NA |

TABLE 4d

Parent sequence #4 eluted from MCF-7 tumor cells: GQDCYRVPVTED (SEQ ID NO: 228)

NO HLA matches

TABLE 4e

Parent sequence #5 eluted from MCF-7 tumor cells: AGLGTKLAAEGLAPN (SEQ ID NO: 229)

| HLA | SEQ | BIMASS | SYFPEITHI |
|---|---|---|---|
| A*0301 | KLAAEGLAP (SEQ ID NO: 223) | 0.120 | 23 |
| A*0801 | GTKLAAEGL (SEQ ID NO: 224) | 4.0 | 22 |

In related LC-MS/MS experiments, a 9-mer peptide bioinformatically predicted to be a FS of the BCL2L13 gene was identified in LC-MS/MS spectra from MCF-7 breast tumor cell elution experiments using the methods described above. The sequence of this peptide is CLWFCYDKC (SEQ ID NO: 230) and fits the HLA-A*0201 binding motif.

h) Antibody Reactivity to Novopeptides

Novopeptides in the FS database in association with particular tumor cell types can be identified. It was observed that peptides longer than 8-10 amino acids (the expected size for MHC elutions) were obtained that matched FS sequences in the FS database. Typically peptides longer than 8-10 amino acids form epitopes for antibodies. Pursuant to the current teaching that protective or therapeutic antibodies may be generated to FS after vaccination, serum taken from patients with different tumor types was assayed for reactivity with predicted novopeptides by standard ELISA techniques. FIG. 8 shows one cancer patient in 23 with antibody reactivity in sera to FS peptide sequences. This finding reveals novopeptides that elicit an anti-tumor antibody response upon vaccination with said novopeptides. Reactive sera is shown by the arrow.

i) Immunological Screening Via CTL

FIG. 9 shows that the probable immunoprotectiveness of a predicted novopeptide can be assayed by immunological screening via a CTL assay, and discloses one method for doing so. CTLs activated against novopeptide 6-21, described above were able to kill MHC-matched tumor cells pulsed with 6-21 peptide, but not impulsed SW480 tumor cells as shown by the square symbol. Since SW480 tumor cells do not express 6-21 novopeptide endogenously, the cells required peptide pulsing. This is a standard Cr release assay that anyone skilled in the art would be able to do.

j) Antibody Responses

A predicted novopeptide elicits a strong antibody response by genetic vaccination. A method for assay of this response is shown. Mice were immunized as described above with a gene vaccine encoding 6-21 novopeptide. Serum was obtained from the mice and incubated with B16 tumor cells. Antibodies specific to novopeptide 6-21 were shown to specifically bind B16 murine tumor cells, while pre-immune sera did not bind.

k) Therapeutic Protection

Novopeptides can also confer therapeutic as well as prophylactic protection. Mice were injected with the B16 tumor cells and then one day later immunized with the 1-78+6-21 novopeptides as gene vaccines. As shown in FIG. 11, the animals receiving both peptides were protected relative to the control animals, but this protection is not as strong as a prophylactic vaccination, as indicated by the lower survival rate (one-third of the mice survived, triangle symbol, compared to 80 percent survival FIG. 6 showing prophylactic immunization).

1) HLA-Typing of Tumor Cells

Candidate novopeptides that are capable of being displayed only in one or a few HLA types that are poorly represented in the target population are less desirable than those capable of being displayed in multiple HLA types that are shared by larger segments of the target population. Here, tumor targets of interest were HLA typed, with the results as shown in Table 5, so that bioinformatically identified candidate novopeptides can then be screened using MHC class I binding algorithms, BIMAS and SYFPEITHI, to determine the novopeptide sequences most likely to be capable of being displayed on the MHC types present in the tumors of interest. This information was used to determine the HLA types for purposes of LC-MS/MS identification and sequencing as described above.

TABLE 5

MHC class I identity of human tumor cell lines

| Tumor cell line | Histological type | HLA type |
| --- | --- | --- |
| MCF-7 | Breast (epithelial adenocarinoma) | A*02/02, B* 18/44, Cw*05/05 |
| SW480 | Colon (adenocarcinoma) | A*02/24, B*07/15, Cw*07/07 |
| A549 | Lung (carcinoma) | A*25/30, B* 18/44, Cw* 12/16 |
| Panc-1 | Pancreas (epithelioid carcinoma) | A*02/11, B*38/38, Cw*12/12 |
| DU-145 | Prostate (carcinoma) | A*03/33, B*50/57, Cw*06/06 |

2. Example 2

A novopeptide associated mutation was identified that occurs in all tumors of humans and mouse identified in the public databases. This comprised a frameshift and the frameshifted gene encodes the SMC1 gene and has the sequence NGSGCSGVYCHEEPQGEDSSV (SEQ ID NO: 8) as compared to the normal wildtype sequence of: NGSGKSNVMDALSFVMGEKIAN (SEQ ID NO: 7). The frameshift was found through informatic analysis of human cancer cDNA sequences compared to normal tissue. Public databases were used. The presence of the same FS was determined in mouse breast and melanoma tumor lines by sequencing cDNA from these tumor lines in the homolog of the SMC1 gene. Thirty-one (31) human tumor libraries were examined for the presence of the FS. In all 30 that were sequenced, the FS in SMC1 was identified as appearing in all lung, breast and melanoma samples but not normal samples. This correlation indicates that this mutation is oncogenic. This frameshift mutation can be used alone or in combination as a component or entirety of a vaccine, either therapeutic or prophylactic, against cancer. It can also be used diagnostically to detect early cancers. This mutation creates an oncogene that is a new anti-cancer drug target. The FS was tested for therapeutic value as a vaccine in the mouse tumor model. The B16 melanoma line was inoculated into mice. One day later the mice were vaccinated with a gene vaccine encoding the FS. No therapeutic effect was noted. However, the 17aa FS is predicted to bind the mouse B16 MHC class I molecules (MHCI) poorly. Therefore epitope-enhanced variants were made based on public programs for improving MHCI binding. When these mice were therapeutically vaccinated there was a positive effect. Therefore the FS is present specifically in human and mouse tumors and is therapeutic when epitope enhanced for mouse. Epitope enhancement is not necessary for human tumors.

An example of a method for producing vaccine components as disclosed herein is as follows:

(a) The NCI database and/or data from the Cancer Genome Atlas is searched and analyzed to find either a variant in the cDNA (RNA) of tumors or in the genomic DNA of tumors that is rare or absent in normal sequences of cDNA (RNA) or DNA.

(b) The presence of the variant in cDNA or mutation in DNA is confirmed by sequencing the cDNA or DNA of tumor cells and normal cells and comparing the two. A panel of tumor and normal cell cDNA and DNA are used to obtain an initial estimate of the frequency of the mutation or variation in tumors versus normal cells.

(c) RNA is extracted from tumor and normal cells and the relative expression of normal messenger RNA versus the RNA encoding the novopeptide is estimated by PCR. In the case of a mutation noted in the DNA, if the mRNA of that mutation is not present in the tumors, the corresponding novopeptide is not pursued. In the case of a variant in RNA, if the variant RNA is present at nearly the same level in tumors as normal cells, the corresponding novopeptide is not pursued.

(d) Candidates remaining at this point are screened by mass spectrometry for being present as novopeptides on the surface of tumor cells but not normal cells. The preference is to elute peptides by acid elution or incubation in buffer to collect the medium. While peptides binding the MHCI can be eluted by more specific protocols, these would miss non MHCI peptides that may be targets of anti-tumor antibodies generated by the vaccine. Chromatographs from the mass spectrometry are compared to the unique database of possible frameshift novopeptides described herein. Candidate novopeptides are confirmed by mass spectrometry sequencing. If a novopeptide is discovered which is longer than 9 amino acids, the MHCI eluted peptides are specifically analyzed for the presence of a nested peptide sequence that would be predicted to bind the HLA of the particular tumor cell.

(e) The candidate novopeptide sequences or nested subsequences thereof are screened for predicted binding to human MHCI molecules. Those that are predicted to bind tightly to common MHCIs receive relatively higher scores than those predicted to bind weakly, or to bind strongly to rare MHCIs.

(f) For those peptides that receive relatively high scores, mouse tumor cells are assayed by PCR or sequencing for the presence of the RNA encoding the novopeptide. If present in mouse tumors, mice are vaccinated with the novopeptide and then challenged with tumor cells to determine if the peptide is protective.

(g) In parallel the high scoring candidates are screened for their presence in human tumors. A number of tumors of the same type as well as a number of different tumors are screened by PCR or sequencing of RNA to determine the overall frequency in patients. In parallel a large number of cell types and cell types from a large number of normal subjects are screened in the same fashion for the presence of the novopeptide encoding RNA. Novopeptide variants that are very infrequent or at very low levels in normal RNA and are present at higher levels in at least 10% of tumors of one type or in 10% in all tumor types proceed to the final screen.

(h) The final defining screen is to determine if the candidate is useful in a prophylactic vaccine. This step would almost assuredly be required before testing of a vaccine in human subjects would be permitted or appropriate. The first screen is for T-cell reactivity. T-cells from humans with the relevant MHCIs will be activated with the test novopeptide. Once a population of such T-cells are created they will be reacted with human tumor cells with the corresponding MHCI type. If these tumor cells are killed or inhibited in growth, such would confirm that these tumor cells are presenting the novopeptide and are susceptible to the vaccine. This same T-cell preparation will also be reacted against a panel of normal cells of the same MHCI. If these cells are not killed or growth inhibited by the novopeptide activated T-cells, such would confirm that this novopeptide is a validated candidate for a cancer vaccine.

(i) For antibody screening the process is simpler. Antibody will be generated to the test novopeptide. This antibody will be reacted against tumor cells to determine if it binds to the surface. If it does this indicates that the tumor is susceptible to the antibody. As above, the same antibody will be reacted to a panel of human normal cells. Novopeptides that induce antibody specific binding are validated as components of a prophylactic cancer vaccine.

M. References

Berzofsky, J., Terabe, M., Oh, S., Belyakov, L, Ahlers, J., Janik, J. & Morris, J. (2004) Progress on new vaccine strategies for the immunotherapy and prevention of cancer. J. Clin. Invest. 2004 June; 113(11): 1515-1525.

Gite, S., Lim, M., Carlson, R., Olejnik, J., Zehnbauer, B. & Rothschild, K. (2003) A high-throughput nonisotopic protein truncation test. Nature Biotechnology: 21(2): 194-197.

Kerr, C. (2002) Huntington's disease provides cancer clues. The Lancet. Oncology: 3(9): 518.

Leaf, C. (2004) Why we're losing the war on cancer. Fortune: 149(6): 76-82:

Lewis, J. (2004) Therapeutic cancer vaccines: using unique antigens. PNAS: 101 Suppl 2:14653-6.

Linnebacher, M., Gebert, J., Rudy, W., Woerner, S., Yuan, Y., Bork, P. & von Knebel Doeberitz, M. (2001) Frameshift peptide-derived T-cell epitopes: a source of novel tumor-specific antigens. Int. J. Cancer. 93(1): 6-11.

Saeterdal, I., Bjorheim, J., Lislerud, K., Gjertsen, M., Bukholm, L, Olsen, O., Nesland, J., Eriksen, J., Moller, M., Lindblom, A., & Gaudernack, G. (2001) Frameshift-mutation-derived peptides as tumor-specific antigens in inherited and spontaneous colorectal cancer. PNAS: 98(23): 13255-60.

Sorensen, S. A., Fenger, K. & Olsen, J. (1999) Significantly lower incidence of cancer among patients with Huntington disease. Cancer: 86(7):1342-6.

Sykes, K. F., and S. A. Johnston. (1999) Linear expression elements: a rapid, in vivo, method to screen for gene functions. Nat Biotechnol 17(4):355-9.

Wang, R., Parkhurst, M., Kawakami, Y., Robbins, P. & Rosenberg, S. A. (1996) Utilization of an alternative open reading frame of a normal gene in generating a novel human cancer antigen. The Journal of Experimental Medicine: 183, 1131-1140.

---

What is claimed is:

1. A synthetic or recombinant peptide, comprising:
a continuous amino acid chain according to the formula D1-D2 and from 8 to 40 amino acids in length, wherein D2 has at least 90% sequence identity to the amino acid sequence CCGIYCHEEPQREDSSI (residues 2 through 18 of SEQ ID NO:15) or CSGVYCHEEPQGEDSSV (residues 5 through 21 of SEQ ID NO:8) and D1 has at least 90% sequence identity to a wild-type SMC 1A sequence or a continuous portion thereof.

2. A vaccine composition comprising: a continuous amino acid chain according to the formula D1-D2 and from 8 to 40 amino acids in length, wherein D2 has at least 90% sequence identity to the amino acid sequence CCGIYCHEEPQREDSSI (residues 2 through 18 of SEQ ID NO:15) or CSGVYCHEEPQGEDSSV (residues 5 through 21 of SEQ ID NO:8) and D1 has at least 90% sequence identity to a wild-type SMC1A sequence or a continuous portion thereof; and a pharmaceutically acceptable carrier.

* * * * *

SEQUENCE LISTING

```
<160> NUMBER OF SEQ ID NOS: 224

<210> SEQ ID NO 1
<211> LENGTH: 66
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
atacctcgaa tgcagcctca ggcttcagcc aatcattgcc agctcctaaa agttatggta      60
gcatga                                                                66

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Ile Pro Arg Met Gln Pro Gln Ala Ser Ala Asn His Cys Gln Leu Leu
 1               5                  10                  15
```

Lys Val Met Val Ala
            20

<210> SEQ ID NO 3
<211> LENGTH: 66
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 3
gccgtgctgc tcatgtgtca gctgtaccag ccatggatgt gtaaggaata ttatagactt    60
ctttga                                                              66

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 4

Ala Val Leu Leu Met Cys Gln Leu Tyr Gln Pro Trp Met Cys Lys Glu
 1               5                  10                  15

Tyr Tyr Arg Leu Leu
            20

<210> SEQ ID NO 5
<211> LENGTH: 66
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 5
gctggaattg ctacacctgg gactgaagac tcaagagact cggatgacgc cctactgaag    60
atgacc                                                              66

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 6

Ala Gly Ile Ala Thr Pro Gly Thr Glu Asp Ser Arg Asp Ser Asp Asp
 1               5                  10                  15

Ala Leu Leu Lys Met Thr
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 7

Asn Gly Ser Gly Lys Ser Asn Val Met Asp Ala Leu Ser Phe Val Met

```
                 1               5                  10                 15
Gly Glu Lys Ile Ala Asn
                 20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 8

Asn Gly Ser Gly Cys Ser Gly Val Tyr Cys His Glu Glu Pro Gln Gly
  1               5                  10                 15

Glu Asp Ser Ser Val
                 20

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 9

His Ile His Thr Pro Leu Leu Asp Arg Lys Leu Asn Ile Leu Met Leu
  1               5                  10                 15

Leu Gly His

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 10

Ser Ala Asn Arg Trp Glu Gln Val Ile Phe Pro
  1               5                  10

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 11

Leu Leu Met Cys Gln Cys Gln Leu Tyr Gln Pro Trp Met Cys Lys Glu
  1               5                  10                 15

Tyr Tyr Arg Leu Leu
                 20

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 12
```

Glu Gln Leu Ala Cys Ile Met Glu Ile Pro Lys Val Phe Leu Lys Ile
1               5                   10                  15

<210> SEQ ID NO 13
<211> LENGTH: 40
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 13

Ser Tyr Ser Gln Ala Val Thr Gly Ser Cys Trp Trp Met Pro Ser Leu
1               5                   10                  15

Leu Pro Asn Ile Tyr Val Leu Asp Arg Leu Leu Val His Ala Thr Lys
                20                  25                  30

Arg Gly Glu Tyr Glu Pro Arg Lys
        35                  40

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 14

Ala Ser Tyr Val Tyr Leu Ser Met Ile Val Thr Ala Thr Cys Leu Trp
1               5                   10                  15

Gly Ser Leu Val
            20

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 15

Gly Cys Cys Gly Ile Tyr Cys His Glu Glu Pro Gln Arg Glu Asp Ser
1               5                   10                  15

Ser Ile

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 16

Pro Trp Met Cys Lys Lys Tyr Tyr Arg Leu Leu
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 17

Asn Pro Cys Gln Leu Leu Lys Pro Met Val Ala
1               5                   10

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 18

Ser Cys Trp Trp Met Pro Ser Leu Leu Pro Asn Ile Tyr Val Leu Asp
1               5                   10                  15

Arg Leu Leu Val His Ala Thr Lys Arg Gly Glu Tyr Glu Pro Arg Lys
            20                  25                  30

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 19

Arg Gly Pro Leu
1

<210> SEQ ID NO 20
<211> LENGTH: 23
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 20

Val His Ile Cys Ser Ile Ser Tyr Phe Thr Thr Cys Val His Gly Ile
1               5                   10                  15

Ile Gln Ile Phe Ser Gln Glu
            20

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 21

Gly Ser Val His Thr Ser Arg Trp Glu Lys Gly Asp Val Val Leu Leu
1               5                   10                  15

Trp Ala Asn Arg Leu
            20

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct -continued

<400> SEQUENCE: 22

Ser Ala His Lys Glu Ser Ser Phe Asp Ile Ile Cys Gln Val
1               5                   10

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 23

Thr Arg His Leu Leu Lys Ser Met Ser Thr Arg Ala Ala Arg Gln Gln
1               5                   10                  15

Arg Thr Tyr Cys Arg Asp Thr Lys Glu Lys Ser Cys Pro Met Ala Met
            20                  25                  30

Thr Ser Gly Gln
        35

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 24

Gly Trp Leu Gln
1

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 25

Leu Arg Gly Gln Gly Gly
1               5

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 26

Leu Leu Thr Met Ile Glu Ala Asn Gly Trp Met
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 27

```
Cys Gly Arg Asn Leu Lys Leu Ser Trp Asn Asn
1               5                   10
```

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 28

```
His Gln Ala Ile Glu Arg Phe Tyr Asp Lys Met Leu Gln Asn Gln Asp
1               5                   10                  15

Val Asp Arg
```

<210> SEQ ID NO 29
<211> LENGTH: 64
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 29

```
Glu Ser Leu Glu Pro Gly His Ala Ser His Ile Leu Pro Ala Ser Ser
1               5                   10                  15

Leu Val Glu Thr Ser Phe Glu Asp Ser Tyr Asn Cys Asp Ser Pro Thr
                20                  25                  30

Gly Gln Gly Phe Gly Lys Ala Gly Asp Trp Pro Ala Ser Cys Ser Gly
            35                  40                  45

Ser Lys Ile Gly Leu Leu Ser Pro Trp Pro Glu Phe Tyr Ala Tyr Trp
        50                  55                  60
```

<210> SEQ ID NO 30
<211> LENGTH: 45
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 30

```
Gly Pro Thr Leu Trp Ser Pro Thr Ala Pro Arg Asn Thr Ala Thr Gln
1               5                   10                  15

Leu Cys Pro Ala Arg Trp Leu Leu Ser Ser Thr Pro Ser Trp Pro Val
                20                  25                  30

Gly Leu Gly Gly Ser Ala Met Trp Thr Met Thr Thr Met
            35                  40                  45
```

<210> SEQ ID NO 31
<211> LENGTH: 31
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 31

```
Lys Tyr Asn Ala Asp Tyr Asp Leu Ser Ala Arg Gln Gly Ala Asp Thr
1               5                   10                  15

Leu Ala Phe Met Ser Leu Leu Glu Glu Lys Leu Leu Pro Val Leu
                20                  25                  30
```

```
<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 32

Ser Arg Ser Gln Leu Gly Met Ala Val Ile Phe Leu Phe Thr Pro Arg
1               5                   10                  15

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 33

Lys Asn Leu Lys Gly Ser Arg Val Cys
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 34

Gly Lys Arg Ser Ser Glu Cys
1               5

<210> SEQ ID NO 35
<211> LENGTH: 28
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 35

Ala Ile Cys Ser Met Gln Ala Leu Arg Gln Pro Met Gly Arg Thr Pro
1               5                   10                  15

Trp Gln Arg Gly Pro Val Cys Leu Asp Ala Ile Ser
            20                  25

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 36

Pro Ser Glu Trp Leu Glu
1               5

<210> SEQ ID NO 37
<211> LENGTH: 70
<212> TYPE: PRT
<213> ORGANISM: Artificial Sequence
<220> FEATURE:
```

<223> OTHER INFORMATION: Description of Artificial Sequence; note =
      synthetic construct

<400> SEQUENCE: 37

Val Glu Asn Gln Ala His Cys Asp Phe Val Lys Leu Arg Asn Met Leu
1               5                   10                  15

Ile Arg Thr His Met His Asp Leu Lys Asp Val Thr Cys Asp Val His
            20                  25                  30

Tyr Glu Asn Tyr Arg Ala His Cys Ile Gln Gln Met Thr Ser Lys Leu
        35                  40                  45

Thr Gln Asp Ser Arg Met Glu Ser Pro Ile Pro Ile Leu Pro Leu Pro
    50                  55                  60

Thr Pro Asp Ala Glu Thr
65                  70

<210> SEQ ID NO 38
<211> LENGTH: 51
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 38

Trp Trp Ile Val Pro Gly Ala Gly Ser Met Leu Pro Val Leu Ser Pro
1               5                   10                  15

Ile Trp Val Pro Trp Ser Pro Ala Ile Gln His Tyr Ser Leu Ser Thr
            20                  25                  30

Thr Gln Leu Arg Ser Leu Val Asn Pro Ala Ser Gln Ser Gln Ser Cys
        35                  40                  45

Ser Leu Gly
    50

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 39

Gly Val Ile Leu Lys Tyr Val Lys Asn
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 40

Gly Thr Gly Cys Ile Ser Ala Ile Pro His
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

```
<400> SEQUENCE: 41

Val Tyr Asp Tyr Arg Trp Lys Ser Thr Arg Gln
1               5                   10

<210> SEQ ID NO 42
<211> LENGTH: 36
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 42

Asp His Arg Ala His Gln Pro Leu Pro Ser Pro Arg Pro Ser Ala Gly
1               5                   10                  15

Thr Val Leu Pro Ala Thr Leu His Ala Arg Phe Gly Ala His Arg Arg
            20                  25                  30

Pro Leu Ala Ser
        35

<210> SEQ ID NO 43
<211> LENGTH: 103
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 43

Met Glu Asp Lys His Ser Ser Asp Ala Ser Ser Leu Leu Pro Gln Asn
1               5                   10                  15

Ile Leu Ser Gln Thr Ser Arg His Asn Asp Arg Asp Tyr Arg Leu Pro
            20                  25                  30

Arg Ala Glu Thr His Ser Ser Ser Thr Pro Val Gln His Pro Ile Lys
        35                  40                  45

Pro Val Val His Pro Thr Ala Thr Pro Ser Thr Val Pro Ser Ser Pro
    50                  55                  60

Phe Thr Leu Gln Ser Asp His Gln Pro Lys Lys Ser Phe Asp Ala Asn
65                  70                  75                  80

Gly Ala Ser Thr Leu Ser Lys Leu Pro Thr Pro Thr Ser Ser Val Pro
                85                  90                  95

Ala Gln Lys Thr Glu Arg Lys
            100

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 44

Gly His Thr Ser Pro Pro Ser His His Pro Asp Ser
1               5                   10

<210> SEQ ID NO 45
<211> LENGTH: 29
<212> TYPE: PRT
<213> ORGANISM: Artificial Sequence
<220> FEATURE:
<223> OTHER INFORMATION: Description of Artificial Sequence; note =
``` synthetic construct

<400> SEQUENCE: 45

Val Leu Cys Leu Leu Val Trp Ala Arg Gly Ala Gly Thr Leu Pro Ser
1               5                   10                  15

Gly Gln Trp Ser Pro Leu Arg Gly Gln His Leu Arg Trp
            20                  25

<210> SEQ ID NO 46
<211> LENGTH: 60
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 46

Val Ile Phe His Phe Arg Thr Met Lys Cys Asp Glu Glu Arg Thr Val
1               5                   10                  15

Ile Asp Asp Ser Arg Gln Val Gly Gln Pro Met His Ile Ile Ile Gly
            20                  25                  30

Asn Met Phe Lys Leu Glu Val Trp Glu Ile Leu Leu Thr Ser Met Arg
        35                  40                  45

Val His Glu Val Ala Glu Phe Trp Cys Asp Thr Ile
    50                  55                  60

<210> SEQ ID NO 47
<211> LENGTH: 22
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 47

Gly Gln Ser Leu Ala Met Leu Ser Arg Leu Val Val Asn Ser Trp Pro
1               5                   10                  15

Gln Ala Val Pro Arg Pro
            20

<210> SEQ ID NO 48
<211> LENGTH: 38
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 48

Pro Leu Thr Glu Ala Ser Tyr Val Asn Leu Pro Thr Ile Ala Leu Cys
1               5                   10                  15

Asn Thr Asp Ser Pro Leu Arg Tyr Val Asp Ile Ala Ile Pro Cys Asn
            20                  25                  30

Asn Lys Gly Ala His Ser
        35

<210> SEQ ID NO 49
<211> LENGTH: 73
<212> TYPE: PRT
<213> ORGANISM: Artificial Sequence
<220> FEATURE:
<223> OTHER INFORMATION: Description of Artificial Sequence; note =
      synthetic construct

```
<400> SEQUENCE: 49

Leu Arg Lys Gly Pro Pro Val Pro Pro Pro Lys His Thr Pro Ser
1               5                   10                  15

Lys Glu Val Lys Gln Glu Gln Ile Leu Ser Leu Phe Glu Asp Thr Phe
                20                  25                  30

Val Pro Glu Ile Ser Val Thr Thr Pro Ser Gln Pro Ala Glu Ala Ser
            35                  40                  45

Glu Val Ala Gly Gly Thr Gln Pro Ala Ala Gly Ala Gln Glu Pro Gly
50                  55                  60

Glu Thr Ala Ala Ser Glu Ala Ala Ser
65                  70

<210> SEQ ID NO 50
<211> LENGTH: 45
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 50

Gln Ile Gln His Pro Thr Ala Ser Leu Ile Ala Lys Val Ala Thr Ala
1               5                   10                  15

Gln Asp Asp Ile Thr Gly Asp Gly Thr Thr Ser Asn Val Leu Ile Ile
                20                  25                  30

Gly Glu Leu Leu Lys Gln Ala Asp Leu Tyr Ile Ser Glu
            35                  40                  45

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 51

Gln Pro Trp Asp His Thr Asn Asn His His Asn Lys
1               5                   10

<210> SEQ ID NO 52
<211> LENGTH: 80
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 52

Ser Val Cys Thr Ser Pro Asn Asp Glu Arg Gly Leu Gln Arg Gln Ser
1               5                   10                  15

Glu Ser Gln Pro Leu Glu Ser Gln Pro Ala Ser Ala Ala Ala Gly Ala
                20                  25                  30

Val Arg Val Gly Arg Arg Pro Glu Ala Ser Lys Arg Arg Glu Asn Gly
            35                  40                  45

Arg Lys Gly Pro Ala Val Arg Leu Thr Gly His Gln Arg Gln Arg Glu
50                  55                  60

Glu Asp Gln Leu Gly Arg Val Leu Val Ser Arg Ile Arg Leu Arg Phe
65                  70                  75                  80

<210> SEQ ID NO 53
```

```
<211> LENGTH: 13
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 53

Glu Met Gly Glu Glu Gly Gly Arg Thr Gly Asn His
1               5                   10

<210> SEQ ID NO 54
<211> LENGTH: 50
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 54

Val Arg Pro Ser Thr Val Ser Met Ala Asn Pro Cys Pro Val Asn Cys
1               5                   10                  15

Ser Ser Trp Gly Cys Pro Lys Ser Thr Arg Pro Ala Cys Ala Ala Val
            20                  25                  30

Met Arg Arg Ser Lys Ala Pro Cys Arg Ser Thr Cys Gly Ser Ala Ala
        35                  40                  45

Tyr Ala
    50

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 55

Ser Cys Leu Asp
1

<210> SEQ ID NO 56
<211> LENGTH: 62
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 56

Lys Trp Thr Thr Ser Leu Glu Lys Ala Ala Thr Thr Ala Thr Ala Arg
1               5                   10                  15

Arg Gly Gly Leu Arg Ser Arg Arg Ser Pro Ser Pro Gly Ser Gln
            20                  25                  30

Gly Pro Ala Gly Ser Gly Arg Ser Gly His Leu Arg Pro Ala Arg Gly
        35                  40                  45

Ala Arg Gln Gly Ala Gly Gly Pro Glu Ala Thr Arg Gly Ser
    50                  55                  60

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence; note =
``` synthetic construct

<400> SEQUENCE: 57

Ala Glu Arg Gly Arg Leu Arg Cys Leu His Gln His Ser Pro Gly Val
1               5                   10                  15

<210> SEQ ID NO 58
<211> LENGTH: 55
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 58

Phe His Gly Asn Glu Ser Leu Trp Lys Asn Phe Lys Glu His His Gln
1               5                   10                  15

Leu Gln Arg Ile Gly Glu Ser Glu Asp Cys Ala Gly Ile Val Ser Phe
            20                  25                  30

Leu Cys Ser Pro Asp Ala Ser Tyr Val Asn Gly Glu Asn Ile Ala Val
        35                  40                  45

Ala Gly Tyr Ser Thr Arg Leu
    50                  55

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 59

His Asp Leu Ser Ser Gln Arg Leu Gln Gly Glu
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 60

Ile Ser His Thr Phe Gly Leu Asp
1               5

<210> SEQ ID NO 61
<211> LENGTH: 48
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 61

Ala Gln Ala Pro Gly Pro Pro Ala Ala Pro Ala Glu Thr Thr Val Ser
1               5                   10                  15

Ser Ser Ser Gly Leu Pro Val Trp Lys Trp Arg Thr Arg Val Cys Val
            20                  25                  30

Ala Trp Tyr Arg Ser Cys Ser Arg Pro Ser Pro Ser Trp Arg Pro Gly
        35                  40                  45

```
<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 62

Arg Arg Val Thr Glu Glu Gln Cys Leu Leu Pro
1               5                   10

<210> SEQ ID NO 63
<211> LENGTH: 36
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 63

Cys Ile His Arg Asp Leu Ala Ala Arg Asn Val Leu Val Thr Glu Asp
1               5                   10                  15

Asn Val Met Lys Ile Ala Asp Phe Gly Leu Ala Arg Asp Ile His His
            20                  25                  30

Ile Asp Tyr Tyr
        35

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 64

Lys Asp Val Gly Glu Pro Ser Leu Phe Pro Leu Ala
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 65

Val Ser Leu Thr Gly Arg Gly Ser Pro Gly Arg Ala Ser Arg Gln Lys
1               5                   10                  15

Ile

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 66

Gly Lys Arg Cys Asp
1               5

<210> SEQ ID NO 67
```

```
<211> LENGTH: 37
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 67

Val Phe Gly Asp Ser Pro Ala Leu Ser Pro Arg Leu Glu Cys Ser Gly
1               5                   10                  15

Arg Ile Ser Ala His Cys Ser Leu Cys Leu Leu Gly Ser Ser Asp Ser
            20                  25                  30

Pro Thr Ser Ala Ser
        35

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 68

Gly Pro Gly Pro Ser Arg
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 69

Ala Thr Pro Thr Trp Lys
1               5

<210> SEQ ID NO 70
<211> LENGTH: 42
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 70

Thr Leu Leu Gln Glu Gln Gly Thr Lys Thr Val Arg Gln Asn Leu Glu
1               5                   10                  15

Pro Leu Phe Glu Gln Tyr Ile Asn Asn Leu Arg Arg Gln Leu Asp Asn
            20                  25                  30

Ile Val Gly Glu Arg Gly Arg Leu Asp Ser
        35                  40

<210> SEQ ID NO 71
<211> LENGTH: 76
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 71

Glu Ser Trp Tyr Gln Thr Lys Tyr Glu Glu Leu Gln Ile Thr Ala Gly
1               5                   10                  15
```

```
Arg His Gly Asp Asp Leu Arg Asn Thr Lys Gln Glu Ile Ala Glu Ile
            20                  25                  30

Asn Arg Met Ile Gln Arg Leu Arg Ser Glu Ile Asp His Val Lys Lys
        35                  40                  45

Gln Cys Ala Asn Leu Gln Ala Ala Ile Ala Asp Ala Glu Gln Arg Gly
 50                  55                  60

Glu Met Ala Leu Lys Asp Ala Lys Asn Lys Leu Glu
 65                  70                  75

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 72

Gly Arg Arg Leu Arg
 1               5

<210> SEQ ID NO 73
<211> LENGTH: 40
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 73

Leu Ala Arg Met Cys Val Pro Thr Leu Leu Thr Asn Leu Arg Ala
 1               5                  10                  15

Arg Leu Val Arg Lys Arg Glu Glu Leu Ser Asn Val Leu Ala Ala Met
            20                  25                  30

Lys Lys Ala Thr Ala Lys Lys Asp
        35                  40

<210> SEQ ID NO 74
<211> LENGTH: 44
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 74

Arg Val Arg His Gly Val Arg Gly Pro Gly His Arg Asp Ser Arg Gly
 1               5                  10                  15

Ser Gly Arg Asn Gly Arg His Pro Glu Arg Glu Gly Asp His Ala Lys
            20                  25                  30

Pro Glu Arg Pro Pro Gly Leu Leu Pro Gly Gln Gln
        35                  40

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 75

Leu Leu Ser Phe Cys Cys Pro Gly Trp Ser Ser Val Ala
```

<210> SEQ ID NO 76
<211> LENGTH: 31
<212> TYPE: PRT
<213> ORGANISM: Artificial Sequence
<220> FEATURE:
<223> OTHER INFORMATION: Description of Artificial Sequence; note = synthetic construct

<400> SEQUENCE: 76

Leu Asp Asp Ser Ile Val Val Lys Leu Val Ser Pro Gly Ser Ala Leu
1               5                   10                  15
Pro Arg Ile Phe Gly Leu Ser Pro Glu Ser Leu Ser Ala Asp His
            20                  25                  30

<210> SEQ ID NO 77
<211> LENGTH: 38
<212> TYPE: PRT
<213> ORGANISM: Artificial Sequence
<220> FEATURE:
<223> OTHER INFORMATION: Description of Artificial Sequence; note = synthetic construct

<400> SEQUENCE: 77

Ile Val Glu Glu Arg Lys Met His Trp Ser Pro Arg Thr Trp Ser Leu
1               5                   10                  15
Gly Asn Gln Phe Met Glu Arg Arg Glu Ser Arg Phe Arg Lys Glu Met
            20                  25                  30
Thr Lys Leu Ser Thr Glu
        35

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence; note = synthetic construct

<400> SEQUENCE: 78

Thr Val Lys His Pro Val Cys Val
1               5

<210> SEQ ID NO 79
<211> LENGTH: 22
<212> TYPE: PRT
<213> ORGANISM: Artificial Sequence
<220> FEATURE:
<223> OTHER INFORMATION: Description of Artificial Sequence; note = synthetic construct

<400> SEQUENCE: 79

Phe His Val Asn His Val Lys Arg Ser Arg Val Pro Leu Ser Val Gly
1               5                   10                  15
Asp His Thr Asn Ser Ser
            20

<210> SEQ ID NO 80
<211> LENGTH: 40
<212> TYPE: PRT
<213> ORGANISM: Artificial Sequence
<220> FEATURE:
<223> OTHER INFORMATION: Description of Artificial Sequence; note = synthetic construct

<400> SEQUENCE: 80

Leu Ala Arg Met Cys Val Pro Thr Leu Leu Thr Asn Leu Arg Ala
1               5                   10                  15

Arg Leu Val Arg Lys Arg Glu Glu Leu Ser Asn Val Leu Ala Ala Met
            20                  25                  30

Lys Lys Ala Thr Ala Lys Lys Asp
        35                  40

<210> SEQ ID NO 81
<211> LENGTH: 41
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 81

Arg Cys Val Leu Lys Ile Gly Glu His Thr Pro Ser Ala Leu Ala Ile
1               5                   10                  15

Met Glu Asn Ala Lys Cys Ser Gly Pro Leu Cys Gln Tyr Leu Pro Ala
            20                  25                  30

Glu Trp His Cys Ala His Arg Gly Ala
        35                  40

<210> SEQ ID NO 82
<211> LENGTH: 44
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 82

Gly Gly Gly Gly Arg Ala Glu Arg Pro Ala Gly Leu Ala Gly Val Gln
1               5                   10                  15

Gly Gln Thr Gly Trp Val Ser Val Leu Lys Pro Pro Ala Leu Leu Pro
            20                  25                  30

Gln Leu Arg Ser Lys Val Lys Arg Leu Ile Arg Phe
        35                  40

<210> SEQ ID NO 83
<211> LENGTH: 82
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 83

Ala Lys Gln Val Leu Leu Gly Arg Lys Val Val Val Arg Cys Glu
1               5                   10                  15

Gly Ile Asn Ile Ser Gly Asn Phe Tyr Thr Lys Gln Val Glu Val Pro
            20                  25                  30

Arg Phe Pro Pro Gln Ala Asp Glu His Gln Leu Leu Pro Arg Leu Leu
        35                  40                  45

Pro Leu Pro Gly Pro Gln Pro His Leu Leu Ala Asp Arg Ala Arg Tyr
    50                  55                  60

Ala Ala Pro Gln Asp Gln Ala Arg Pro Gly Arg Ser Gly Pro Pro Gln
65                  70                  75                  80

Gly Val

```
<210> SEQ ID NO 84
<211> LENGTH: 69
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 84

Gly Asn Phe Tyr Arg Asn Lys Leu Lys Tyr Leu Ala Phe Leu Arg Lys
1               5                   10                  15

Arg Met Asn Thr Asn Pro Ser Arg Gly Pro Tyr His Phe Arg Ala Pro
            20                  25                  30

Ser Arg Ile Phe Trp Arg Thr Val Arg Gly Met Leu Pro His Lys Thr
        35                  40                  45

Lys Arg Gly Gln Ala Ala Leu Asp Arg Leu Lys Val Phe Asp Gly Ile
    50                  55                  60

Pro Pro Pro Thr Thr
65

<210> SEQ ID NO 85
<211> LENGTH: 41
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 85

Val Gly Asp Glu Ala Gln Ser Lys Arg Gly Ile Leu Thr Leu Lys Tyr
1               5                   10                  15

Pro Ile Glu His Gly Ile Val Thr Thr Pro Ser Thr Thr Ser Cys Ala
            20                  25                  30

Trp Pro Arg Arg Ser Thr Arg Cys Cys
        35                  40

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 86

Gln Ala Pro Arg Leu
1               5

<210> SEQ ID NO 87
<211> LENGTH: 28
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 87

Gly Thr Cys Trp Arg Lys Trp His Arg Lys Cys Lys Leu Pro Ile Lys
1               5                   10                  15

Ser Thr Gly Leu Arg Arg Gln Ile Ile Pro Trp Gln
            20                  25

<210> SEQ ID NO 88
```

```
<211> LENGTH: 67
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 88

Gly Phe Thr Thr Ala Ala Tyr Leu Arg Ile His Ala Val Lys Asp His
1               5                   10                  15

Gly Leu Gln Ala Pro Arg Ala Asp Arg Ile Leu Cys Lys Leu Cys Ser
            20                  25                  30

Val His Cys Lys Thr Pro Ala Gln Leu Ala Gly His Met Gln Thr His
        35                  40                  45

Leu Gly Gly Ala Ala Pro Pro Val Pro Gly Asp Ala Pro Gln Pro Gln
    50                  55                  60

Pro Thr Cys
65

<210> SEQ ID NO 89
<211> LENGTH: 34
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 89

Arg Glu Glu Met Ser Thr Gln Trp Leu Pro Thr Tyr Val Pro Ile Pro
1               5                   10                  15

Pro Ser Cys His Lys Phe Pro Lys Asn Ser Gln Asn His Cys Ser Pro
            20                  25                  30

His Leu

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 90

Tyr Phe Leu Ser Ser Ile Arg Phe Ile Ser Thr Phe
1               5                   10

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 91

Arg Asn Pro Gln Gln Met Pro Leu
1               5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct
```

```
<400> SEQUENCE: 92

Arg His Cys Thr Trp Leu
1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 93

Trp Arg Ile Phe Leu His
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 94

Gly Leu Ala Asp Ser
1               5

<210> SEQ ID NO 95
<211> LENGTH: 19
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 95

Glu Phe Ser Ser Gln Leu Trp Thr Leu Lys Glu Gly Ala Glu Val Ala
1               5                   10                  15

Pro Gly Gln

<210> SEQ ID NO 96
<211> LENGTH: 41
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 96

Ser Pro Leu Leu His Trp Asp Gly Ser Ala Trp Ser Pro Pro Ala Leu
1               5                   10                  15

Trp Trp Thr Val Cys Glu Thr Gly Leu Gln Leu Gly Gly Val Gln Val
            20                  25                  30

Thr Thr Gly Glu Glu Gly Gly Asn Leu
        35                  40

<210> SEQ ID NO 97
<211> LENGTH: 58
<212> TYPE: PRT
<213> ORGANISM: Artificial Sequence
<220> FEATURE:
<223> OTHER INFORMATION: Description of Artificial Sequence; note =
      synthetic construct
```

<400> SEQUENCE: 97

Val Val Val Val Lys Asp Arg Glu Thr Gln Arg Ser Arg Gly Phe Gly
1               5                   10                  15

Phe Ile Thr Phe Thr Asn Pro Asp Leu Trp Met Val Arg Ser Val
            20                  25                  30

Trp Ile Met Gln Ala Ser Leu Leu Gly Glu Pro Glu Val Ala Leu
        35                  40                  45

Gly Pro Met Gly Val Val Ala Ala Thr Leu
    50                  55

<210> SEQ ID NO 98
<211> LENGTH: 65
<212> TYPE: PRT
<213> ORGANISM: Artificial Sequence
<220> FEATURE:
<223> OTHER INFORMATION: Description of Artificial Sequence; note = synthetic construct

<400> SEQUENCE: 98

Leu Phe Leu Trp Leu Ser Ser Gln Ala Leu Thr Leu Arg Pro Cys Thr
1               5                   10                  15

Thr Ser Gly Thr Ser Ile Ser Gln Pro Pro Gly Ser Cys Phe Ala Pro
            20                  25                  30

Trp Asp Arg Thr His Arg Thr Trp Phe Arg Pro Leu Ser Thr Ser Ser
        35                  40                  45

Ala Arg Leu Asp His Pro Cys Ala Asp Arg Pro Thr Ser Ala Thr Arg
    50                  55                  60

Arg
65

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence; note = synthetic construct

<400> SEQUENCE: 99

Lys Leu Val Gly Asn Ser Gln Lys Glu Cys Gly Val Ser
1               5                   10

<210> SEQ ID NO 100
<211> LENGTH: 87
<212> TYPE: PRT
<213> ORGANISM: Artificial Sequence
<220> FEATURE:
<223> OTHER INFORMATION: Description of Artificial Sequence; note = synthetic construct

<400> SEQUENCE: 100

Gly Val Ser Gly Val Gly Gly Val Leu Val Thr Glu Gly Lys Leu
1               5                   10                  15

Arg His Arg Ala Thr Lys Leu Met Leu Gly His Pro Glu His Gln Gly
            20                  25                  30

Arg Ala Gly Asn Lys His Ser Cys Val Leu Asn Ser Thr Pro Cys Ser
        35                  40                  45

Leu Ser Ala Ser His Leu Thr Gln Gly Pro Cys Trp Leu Leu Thr Asp
    50                  55                  60

Ser Leu Gly Val Trp Leu Ala Ala Ile Leu Gln Asp Arg Ala Pro Pro
65                  70                  75                  80

Trp Pro Cys Pro His Gln Trp
            85

<210> SEQ ID NO 101
<211> LENGTH: 29
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 101

Met Asp Leu Lys Glu Gln Pro Gly Asn Thr Ile Ser Ala Gly Gln Glu
1               5                   10                  15

Asp Phe Pro Ser Val Leu Leu Glu Thr Ala Ala Ser Leu
            20                  25

<210> SEQ ID NO 102
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 102

Arg Ala Ala Leu Val Leu Val Val Leu Leu Ile Ala Gly Gly Leu Phe
1               5                   10                  15

Met Phe Thr Tyr Lys
            20

<210> SEQ ID NO 103
<211> LENGTH: 22
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 103

Val Arg Met Ala Arg Gly Gly Ala Ala Leu Gly Arg Glu Leu Ser Arg
1               5                   10                  15

Gly Ala Glu Gln Gly Arg
            20

<210> SEQ ID NO 104
<211> LENGTH: 58
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 104

Lys Lys Leu Asn Gly Gly Arg His Val Gln Ile Leu Arg Gly Phe
1               5                   10                  15

Asp Pro Phe Met Asn Leu Val Ile Asp Glu Cys Val Glu Met Ala Thr
            20                  25                  30

Ser Gly Gln Gln Asn Asn Ile Gly Met Val Val Ile Arg Gly Asn Ser
        35                  40                  45

Ile Ile Met Leu Glu Ala Leu Glu Arg Val
    50                  55

```
<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 105

Val Gly Leu Ala Pro Leu Pro
 1               5

<210> SEQ ID NO 106
<211> LENGTH: 57
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 106

Met Leu Leu Arg Arg Arg Gly Thr Pro Ser Ser Pro Cys Ala Arg Thr
 1               5                  10                  15

Thr Thr Ala Phe Val Pro Trp Pro Ser Thr Thr Ala Ser Arg Leu Cys
            20                  25                  30

Ser Pro Pro Pro Arg Thr Ala Arg Ser Ser Ser Gly Thr Cys Arg Arg
        35                  40                  45

Arg Ser Arg Pro Arg Arg Met Arg Arg
    50                  55

<210> SEQ ID NO 107
<211> LENGTH: 33
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 107

Arg Gly Leu Gln Asp Pro Cys His Val Val Ile Phe Phe Ile Glu Gly
 1               5                  10                  15

Leu Ala Ala Ala Ala Asn Ala Gly Pro Gly Ala Gly Ala Gly Glu
            20                  25                  30

Ala

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 108

Ala Trp Thr Arg Phe Ala Met Arg Ala
 1               5

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 109
```

```
Val His Arg Ala Leu Arg Leu Ser Thr Arg Leu
1               5                   10

<210> SEQ ID NO 110
<211> LENGTH: 67
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 110

Gly Thr Lys Thr Cys Glu Ala Glu Pro Gly Ala Val Val Arg Ala Val
1               5                   10                  15

His Gln Gln Pro Gln Glu Ala Ala Gly Gln His Arg Gly Gly Thr Gly
            20                  25                  30

Ser Ser Gly Leu Gly Ala Glu Lys His Ala Gly Pro Gly Gly Gly Pro
        35                  40                  45

Gln Glu Gln Thr Met Arg Met Lys Ser Thr Ser Ala Gln Gln Gln Arg
    50                  55                  60

Met Asn Leu
65

<210> SEQ ID NO 111
<211> LENGTH: 24
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 111

Ser Cys Leu Leu Val Lys Ile Phe Leu Phe Ile Leu Met Phe Ile Ala
1               5                   10                  15

Met Val Ile Ser Val Tyr Pro Phe
            20

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 112

Ser Leu Ile Ile Ile Lys Arg Tyr Gly His Phe
1               5                   10

<210> SEQ ID NO 113
<211> LENGTH: 23
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 113

Thr Arg Tyr Gly Arg Cys Val His Cys Arg Glu Ile Val Leu Gln Gln
1               5                   10                  15

Pro Ser Gly His Arg Gln Pro
            20
```

```
<210> SEQ ID NO 114
<211> LENGTH: 23
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 114

Glu Asp Arg Lys Arg Gly Cys Cys Pro Thr Ser Ser Ser Leu Pro Ile
 1               5                  10                  15

Ser Leu Arg Val Arg Leu Ser
             20

<210> SEQ ID NO 115
<211> LENGTH: 63
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 115

His Thr Gly Val Tyr Pro Ile Leu Ser Arg Ser Leu Arg Gln Met Ala
 1               5                  10                  15

Gln Gly Lys Asp Pro Thr Glu Trp His Val His Thr Cys Gly Leu Ala
             20                  25                  30

Asn Met Phe Ala Tyr His Thr Leu Gly Tyr Glu Asp Leu Asp Glu Leu
         35                  40                  45

Gln Lys Glu Pro Gln Pro Leu Val Phe Val Ile Glu Leu Leu Gln
     50                  55                  60

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 116

Thr Gln Arg Leu Thr Gly Arg Pro Thr Trp Pro Arg
 1               5                  10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 117

Val Trp Met Arg Ser Pro Leu Ser Thr Phe
 1               5                  10

<210> SEQ ID NO 118
<211> LENGTH: 25
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 118

Ser Leu Arg Lys Arg Gln Arg Thr Leu Ala Trp Lys His Thr Gly Arg
```

```
                1               5                   10                  15
Glu Arg Asp Gln Ala Thr Val Ile Leu
            20                  25

<210> SEQ ID NO 119
<211> LENGTH: 29
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 119

Cys His Gln Glu Thr Lys Val His Gln Lys His Pro Glu Asn Tyr Gln
  1               5                   10                  15

Val Tyr Glu Asn Gly Ser Gly Ser Lys Ile Cys Pro Ser
            20                  25

<210> SEQ ID NO 120
<211> LENGTH: 24
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 120

Ile Phe Phe Phe Phe Gly Ile His Leu Gly Ser Ile Phe Ile Leu Trp
  1               5                   10                  15

His Gly Asn Leu Gln Arg Ile Lys
            20

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 121

Gly Cys Cys Phe Phe Trp Trp Ser Val Tyr Gln Glu Gly
  1               5                   10

<210> SEQ ID NO 122
<211> LENGTH: 57
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 122

Ser Asn Gln Ala Ser Trp Arg Lys Ala Asn Leu Thr Cys Lys Ile Ala
  1               5                   10                  15

Ile Asp Asn Leu Glu Lys Ala Glu Leu Leu Gln Gly Gly Asp Leu Leu
            20                  25                  30

Arg Gln Arg Pro Pro Lys Arg Ala Trp Pro Arg His Pro Val Pro Ser
        35                  40                  45

Leu Arg Ala Ser Trp Gly Ser Ala Gly
        50                  55

<210> SEQ ID NO 123
<211> LENGTH: 20
```

```
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 123

Ala Pro Ser Cys Cys Gln Ala Thr Ser Ala Lys Gly Gly Gln Thr Gly
 1               5                  10                  15

Pro Phe Gln Cys
            20

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 124

Asp Pro Gly Ala Pro Glu Pro Trp Arg Gly
 1               5                  10

<210> SEQ ID NO 125
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 125

Ala Glu Arg Glu
 1

<210> SEQ ID NO 126
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 126

Ala Arg Arg Gly
 1

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 127

Val Ile Gln Arg Leu Leu Cys
 1               5

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct
```

<400> SEQUENCE: 128

Gly Lys Asn Cys Asp Ser Gly Glu Glu Ser Lys
1               5                   10

<210> SEQ ID NO 129
<211> LENGTH: 3
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 129

Arg Pro Arg
1

<210> SEQ ID NO 130
<211> LENGTH: 27
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 130

Ala Ala Cys Trp Thr Leu Ser Met Asp Thr Leu Leu Ala Leu Leu Ile
1               5                   10                  15

Lys Glu Pro Gly Leu Gly Pro Cys Trp Thr Cys
            20                  25

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 131

Cys Arg Ser Cys Ser Thr Phe
1               5

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 132

Gly Glu Arg Arg Glu
1               5

<210> SEQ ID NO 133
<211> LENGTH: 51
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 133

Arg Asp Ser Ile Val Ala Glu Leu Asp Arg Glu Met Ser Arg Ser Val
1               5                   10                  15

Asp Val Thr Asn Thr Thr Phe Leu Leu Met Ala Ala Ser Ile Tyr Leu

```
                    20                  25                  30

His Asp Gln Asn Pro Asp Ala Ala Leu Arg Ala Leu His Gln Gly Asp
        35                  40                  45

Ser Leu Glu
    50

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 134

Leu Gln Thr Leu Glu Ile Lys Lys Val Leu Glu
1               5                   10

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 135

Asp Lys Thr Phe Gln Arg Lys Tyr
1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 136

Ile Pro Lys Val Phe Leu Lys Ile
1               5

<210> SEQ ID NO 137
<211> LENGTH: 27
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 137

Asp Pro Lys Gly Asn Ser Gly Thr Trp Arg Leu Tyr Gly Ser His Leu
1               5                   10                  15

Ser Cys Leu His Trp Trp Asn Lys Cys Ser Lys
            20                  25

<210> SEQ ID NO 138
<211> LENGTH: 18
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 138

Lys Phe Lys Phe Glu Cys Asn Phe Arg Ser Tyr Glu Tyr Arg Asn Tyr
```

Tyr Leu

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence; note = synthetic construct

<400> SEQUENCE: 139

Val Gly Asn Leu His Phe
1               5

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence; note = synthetic construct

<400> SEQUENCE: 140

Gly Cys Gln Pro Asp His Gly Ala Gly Ala Trp Ala Ala Cys Val Pro
1               5                   10                  15

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence; note = synthetic construct

<400> SEQUENCE: 141

Ile Pro Ala Leu Leu Leu Ala Ser Cys Leu Gly
1               5                   10

<210> SEQ ID NO 142
<211> LENGTH: 32
<212> TYPE: PRT
<213> ORGANISM: Artificial Sequence
<220> FEATURE:
<223> OTHER INFORMATION: Description of Artificial Sequence; note = synthetic construct

<400> SEQUENCE: 142

Ser Cys Arg Thr His Pro Thr Pro Ser Leu Arg Ala Ala Trp Ser Pro
1               5                   10                  15

Gln Pro Trp Thr Arg Pro Gly Trp Arg Pro Arg Gly Arg Arg Arg Cys
            20                  25                  30

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence; note = synthetic construct

<400> SEQUENCE: 143

Ala Val Arg Trp Ser Ser Gly Thr Arg Met Ser Pro Ser Leu Pro Arg
1               5                   10                  15

Ser

<210> SEQ ID NO 144
<211> LENGTH: 64
<212> TYPE: PRT
<213> ORGANISM: Artificial Sequence
<220> FEATURE:
<223> OTHER INFORMATION: Description of Artificial Sequence; note = synthetic construct

<400> SEQUENCE: 144

Leu Pro Tyr Leu Ile Asp Gly Ala His Lys Ile Thr Gln Ser Asn Ala
1               5                   10                  15

Ile Leu Cys Tyr Ile Ala Arg Lys His Asn Leu Cys Gly Glu Thr Glu
            20                  25                  30

Glu Glu Lys Ile Arg Val Asp Ile Leu Glu Asn Gln Ala Met Asp Val
        35                  40                  45

Ser Asn Gln Leu Ala Arg Val Cys Tyr Ser Pro Asp Phe Glu Lys Leu
    50                  55                  60

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence; note = synthetic construct

<400> SEQUENCE: 145

Val Trp Pro Ser Cys Ser Thr
1               5

<210> SEQ ID NO 146
<211> LENGTH: 42
<212> TYPE: PRT
<213> ORGANISM: Artificial Sequence
<220> FEATURE:
<223> OTHER INFORMATION: Description of Artificial Sequence; note = synthetic construct

<400> SEQUENCE: 146

Leu Ala Ile Ile Glu Tyr Leu Glu Met Arg Pro Thr Pro Arg Leu
1               5                   10                  15

Leu Pro Gln Asp Pro Lys Lys Arg Ala Ser Val Arg Met Ile Ser Asp
            20                  25                  30

Leu Ile Ala Gly Gly Ile Gln Pro Leu Gln
        35                  40

<210> SEQ ID NO 147
<211> LENGTH: 55
<212> TYPE: PRT
<213> ORGANISM: Artificial Sequence
<220> FEATURE:
<223> OTHER INFORMATION: Description of Artificial Sequence; note = synthetic construct

<400> SEQUENCE: 147

Gly Glu Gly Asp Ile His Glu Asn Val Asp Thr Asp Leu Pro Gly Ser
1               5                   10                  15

Leu Gly Gln Ser Glu Glu Lys Pro Val Pro Ala Pro Val Pro Ser
            20                  25                  30

Pro Val Ala Pro Ala Pro Val Pro Ser Arg Arg Asn Pro Pro Gly Gly
        35                  40                  45

Lys Ser Ser Leu Val Leu Gly
    50                  55

<210> SEQ ID NO 148
<211> LENGTH: 42
<212> TYPE: PRT
<213> ORGANISM: Artificial Sequence
<220> FEATURE:
<223> OTHER INFORMATION: Description of Artificial Sequence; note = synthetic construct

<400> SEQUENCE: 148

Met Pro Trp Thr Ile Leu Pro Gly Arg Thr Asn Ser Thr Ile Pro Lys
1               5                   10                  15

Ser Ser Asn Lys Lys Thr Ser Gln Ala Thr Arg Gly Asp His Trp Lys
            20                  25                  30

Trp Ser Ser Arg Pro Ile Val Gln Lys
        35                  40

<210> SEQ ID NO 149
<211> LENGTH: 29
<212> TYPE: PRT
<213> ORGANISM: Artificial Sequence
<220> FEATURE:
<223> OTHER INFORMATION: Description of Artificial Sequence; note = synthetic construct

<400> SEQUENCE: 149

Met Ile Lys Lys Trp Leu Tyr Val Ile Cys Val Glu Asp His Val Ser
1               5                   10                  15

Glu Ile Arg Leu Tyr Ile Ser Lys Cys Trp Asp His Ala
            20                  25

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence; note = synthetic construct

<400> SEQUENCE: 150

Cys Gln Trp Val Met Phe Gly
1               5

<210> SEQ ID NO 151
<211> LENGTH: 90
<212> TYPE: PRT
<213> ORGANISM: Artificial Sequence
<220> FEATURE:
<223> OTHER INFORMATION: Description of Artificial Sequence; note = synthetic construct

<400> SEQUENCE: 151

Glu His Asp Pro Gly Pro Pro Arg Pro Gly Ala Ala Gly Pro Cys Gly
1               5                   10                  15

Gly Gly Arg Leu Leu Leu Thr Gln Pro Gly Gly Pro Ala Gly Gly Ser
            20                  25                  30

Gly Pro His Glu Thr Glu Trp Cys Leu Pro Leu His Gln Arg Arg Ala
        35                  40                  45

His Ser Ala Ala Cys Gly Arg Cys Arg Pro Pro Val Gln Gly Asp
    50                  55                  60

Pro Glu Thr His Gln Gly Ala Arg Pro Arg Gln Arg Thr Ala Gly Pro
65                  70                  75                  80

Leu Pro Arg Pro Glu Leu Pro Pro Pro Leu

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence; note = synthetic construct

<400> SEQUENCE: 152

Arg Lys Ala Gln Arg Tyr Thr Gly Gln
1               5

<210> SEQ ID NO 153
<211> LENGTH: 102
<212> TYPE: PRT
<213> ORGANISM: Artificial Sequence
<220> FEATURE:
<223> OTHER INFORMATION: Description of Artificial Sequence; note = synthetic construct

<400> SEQUENCE: 153

Asp Leu Leu Leu Pro Gly Glu Val Glu Gln Asp Val Ser Thr Ser
1               5                   10                  15

Ile Pro Ser Cys Ile Pro Phe Val Ala Gln Pro Pro Thr Cys Glu Val
            20                  25                  30

Lys Pro Lys Pro Ser Val Lys Arg Met Asp Lys Gln Thr Glu Glu Ile
        35                  40                  45

Leu Gly Asp Glu Val Gln Leu Phe Ser Leu Asp Glu Glu Phe Asp Tyr
    50                  55                  60

Asp Asn Val Met Leu Thr Ser Lys Phe Ser Pro Ala Glu Ile Glu Asn
65                  70                  75                  80

Ile Lys Glu Leu Cys Lys Gln Gln Lys Arg Lys Asp Thr Ser Pro Asp
                85                  90                  95

Leu Glu Lys Ser Cys Asp
            100

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence; note = synthetic construct

<400> SEQUENCE: 154

Gly Ser Ser Leu Leu
1               5

<210> SEQ ID NO 155
<211> LENGTH: 29
<212> TYPE: PRT
<213> ORGANISM: Artificial Sequence
<220> FEATURE:
<223> OTHER INFORMATION: Description of Artificial Sequence; note = synthetic construct

<400> SEQUENCE: 155

Met Ile Lys Lys Trp Leu Tyr Val Ile Cys Val Glu Asp His Val Ser
1               5                   10                  15

Glu Ile Arg Pro Tyr Ile Ser Lys Cys Trp Asp His Ala
            20                  25

<210> SEQ ID NO 156
<211> LENGTH: 13
<212> TYPE: PRT
<213> ORGANISM: Artificial Sequence
<220> FEATURE:
<223> OTHER INFORMATION: Description of Artificial Sequence; note = synthetic construct

<400> SEQUENCE: 156

Val Pro Ser Trp Lys Asn Arg Gln Gln Asn Ser Leu Glu
1               5                   10

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence; note = synthetic construct

<400> SEQUENCE: 157

Cys Lys Thr Trp His Ser Ala Trp Val
1               5

<210> SEQ ID NO 158
<211> LENGTH: 81
<212> TYPE: PRT
<213> ORGANISM: Artificial Sequence
<220> FEATURE:
<223> OTHER INFORMATION: Description of Artificial Sequence; note = synthetic construct

<400> SEQUENCE: 158

Val Ser Ala Cys Pro Ser Val Pro Gly His Ser Arg Pro Cys Trp Ala
1               5                   10                  15

Arg Pro Leu Ser Pro Leu Pro Ala Pro Ala Glu Val Pro Gly Pro Val
            20                  25                  30

Leu Pro Arg Gln Val Ala Gly Phe Val Trp Gly Gln Ser Gly Pro Ala
        35                  40                  45

Glu His Arg Gln His Leu Leu Leu Pro Gln Ser Gly Leu Ala Leu Pro
    50                  55                  60

Gly Val Cys Gly Ala Ala Ala Pro Pro Gly Pro His Leu Pro Gly
65                  70                  75                  80

Gln

<210> SEQ ID NO 159
<211> LENGTH: 29
<212> TYPE: PRT
<213> ORGANISM: Artificial Sequence
<220> FEATURE:
<223> OTHER INFORMATION: Description of Artificial Sequence; note = synthetic construct

<400> SEQUENCE: 159

Met Pro Ser Thr Ala Ser Pro Trp Ala Ala Ser Pro Leu Ser Cys Leu
1               5                   10                  15

Gln Thr Ser Phe Gln Arg Gln Gln Glu Thr Phe Met Leu
            20                  25

<210> SEQ ID NO 160
<211> LENGTH: 33
<212> TYPE: PRT
<213> ORGANISM: Artificial Sequence
<220> FEATURE:

```
<223> OTHER INFORMATION: Description of Artificial Sequence; note =
      synthetic construct

<400> SEQUENCE: 160

Tyr Val Tyr Gln Ser Gln Tyr Cys Gly Phe Leu Gln Pro Glu Gln Asn
1               5                   10                  15

Cys His Pro Arg Glu Glu Gly Met Glu Phe Met Val Leu Ala Gln Lys
                20                  25                  30

Phe

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 161

Cys Lys Thr Trp His Ser Ala Trp Val
1               5

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 162

Arg Met Leu Gly Pro Arg Pro Pro Arg Ala Ala Arg Phe Arg
1               5                   10

<210> SEQ ID NO 163
<211> LENGTH: 52
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 163

Lys Asn Ile Leu Val Arg Met Val Ser Glu Ala Gly Thr Gly Phe Cys
1               5                   10                  15

Phe Asn Thr Lys Arg Asn Arg Leu Arg Glu Lys Leu Thr Leu Leu His
                20                  25                  30

Tyr Asp Pro Val Val Lys Gln Arg Val Leu Phe Val Glu Lys Lys Lys
            35                  40                  45

Ile Arg Ser Leu
    50

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 164

Ser Val Gly Ser Leu Ile
1               5
```

-continued

```
<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 165

Arg Gly Cys His Glu Glu Ser Trp Cys Gly Thr Gln
 1               5                  10

<210> SEQ ID NO 166
<211> LENGTH: 18
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 166

Glu Val Gly Val Gly Leu Pro Pro Gly Lys Trp Leu Ala Trp Pro Asn
 1               5                  10                  15

Leu Thr

<210> SEQ ID NO 167
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 167

Leu Phe Gln Leu
 1

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 168

Lys Leu Tyr Cys Ser Phe
 1               5

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 169

Leu Phe Leu Ile His
 1               5

<210> SEQ ID NO 170
<211> LENGTH: 18
<212> TYPE: PRT
<213> ORGANISM: Artificial Sequence
<220> FEATURE:
<223> OTHER INFORMATION: Description of Artificial Sequence; note =
      synthetic construct
```

<400> SEQUENCE: 170

Arg Cys Ala Ala Thr Ser Met Asp Asn Ser Met Thr Ser Lys Ser Cys
1               5                   10                  15

Ser Glu

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 171

Arg Asn Ala Met Tyr
1               5

<210> SEQ ID NO 172
<211> LENGTH: 39
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 172

Glu Asn Lys Ser Thr Asn Ser Arg Val Cys Glu Gly Lys Arg Cys Phe
1               5                   10                  15

His His Pro Asn Cys Phe Glu Gly Arg Glu His His His Gly Ala
            20                  25                  30

Pro Asp His Gly Val Cys Met
        35

<210> SEQ ID NO 173
<211> LENGTH: 27
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 173

Ala Lys Phe Val Ser Tyr Cys Gly Ala Ser Asn Thr Arg Arg Ser Gly
1               5                   10                  15

Arg Cys Gln Phe Trp Ala Thr Ser Phe Arg Val
            20                  25

<210> SEQ ID NO 174
<211> LENGTH: 34
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 174

Val Ser Gly Trp Ser Ser Asp Pro Cys Gly Ser Cys Arg Gln Val Cys
1               5                   10                  15

Ser Gly Asn Gln Arg Arg Trp Leu Trp Gly Pro Trp Ala Trp Ser Gln
            20                  25                  30

Leu Leu

```
<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 175

Arg Lys Leu Asn Ile Leu Met Leu Leu Gly His
1               5                   10

<210> SEQ ID NO 176
<211> LENGTH: 33
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 176

Tyr Val Tyr Gln Ser Gln Tyr Cys Gly Phe Leu Gln Pro Glu Gln Asn
1               5                   10                  15

Cys His Pro Arg Glu Glu Gly Met Glu Phe Met Val Leu Ala Gln Lys
            20                  25                  30

Phe

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 177

Gly Phe Val Phe Ala Pro Arg
1               5

<210> SEQ ID NO 178
<211> LENGTH: 35
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 178

Tyr Ser Cys Glu Phe Gly Ser Ala Lys Tyr Tyr Ala Leu Cys Gly Phe
1               5                   10                  15

Gly Gly Val Leu Ser Cys Gly Leu Thr His Thr Ala Val Val Pro Leu
            20                  25                  30

Asp Leu Val
        35

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 179

Phe Ile Asp Ala Val Trp Lys
1               5
```

```
<210> SEQ ID NO 180
<211> LENGTH: 18
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 180

Arg Leu Ser Pro Ser Val Ser His Ser Ile Cys Arg Arg Gln Gln Phe
 1               5                  10                  15

Gly Val

<210> SEQ ID NO 181
<211> LENGTH: 76
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 181

Val Cys Glu Thr Gln Leu His Arg Leu Met Thr Lys Ser Pro Leu Ala
 1               5                  10                  15

Phe Asp Thr Arg Pro Trp Asp Ser Gln Thr Leu Leu Trp Thr Pro Leu
             20                  25                  30

Gly Ser Gly Phe Cys Leu Thr Phe Pro Gly Gly Leu Gly Gln Gly
         35                  40                  45

Gly His Glu Gly Leu Ser Leu Pro Lys Thr Gln Thr Pro Val Pro His
     50                  55                  60

Ser Val Leu Leu His Pro Pro Pro His Leu His Cys
 65                  70                  75

<210> SEQ ID NO 182
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 182

Met Arg Glu Cys Ile Ser Val His Val Gly Gln Ala Gly Val
 1               5                  10

<210> SEQ ID NO 183
<211> LENGTH: 26
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 183

Glu Asp Glu Val Asp Met Leu Ser Asp Gly Cys Gly Ser Glu Glu Arg
 1               5                  10                  15

Arg Ser Gln Ser Leu Pro Ala Met Ala Ala
             20                  25

<210> SEQ ID NO 184
<211> LENGTH: 32
<212> TYPE: PRT
<213> ORGANISM: Artificial Sequence
```

<220> FEATURE:
<223> OTHER INFORMATION: Description of Artificial Sequence; note = synthetic construct

<400> SEQUENCE: 184

Asp Lys Asn Ile Arg Glu Leu Ser Leu Val Ser Met Lys Ser Leu Asn
1               5                   10                  15

Pro Val Thr Leu Cys Arg Glu Pro Pro Ala Thr Val Phe Gln Ala His
            20                  25                  30

<210> SEQ ID NO 185
<211> LENGTH: 92
<212> TYPE: PRT
<213> ORGANISM: Artificial Sequence
<220> FEATURE:
<223> OTHER INFORMATION: Description of Artificial Sequence; note = synthetic construct

<400> SEQUENCE: 185

Gly Phe Arg Asp Asp Phe Leu Gly Gly Arg Gly Gly Ser Arg Pro Gly
1               5                   10                  15

Asp Arg Arg Thr Gly Pro Pro Met Gly Ser Arg Phe Arg Asp Gly Pro
            20                  25                  30

Pro Leu Arg Gly Ser Asn Met Asp Phe Arg Glu Pro Thr Glu Glu Glu
        35                  40                  45

Arg Ala Gln Arg Pro Arg Leu Gln Leu Lys Pro Arg Thr Val Ala Thr
50                  55                  60

Pro Leu Asn Gln Val Ala Asn Pro Asn Ser Ala Ile Phe Gly Gly Ala
65                  70                  75                  80

Arg Pro Arg Glu Glu Val Val Gln Lys Glu Gln Glu
                85                  90

<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence; note = synthetic construct

<400> SEQUENCE: 186

Ile Phe Phe His Leu Cys Val Met Ile Val Gln Glu Tyr Phe
1               5                   10

<210> SEQ ID NO 187
<211> LENGTH: 6
<212> TYPE: PRT
<213> ORGANISM: Artificial Sequence
<220> FEATURE:
<223> OTHER INFORMATION: Description of Artificial Sequence; note = synthetic construct

<400> SEQUENCE: 187

Cys Pro Ala Glu Ile Lys
1               5

<210> SEQ ID NO 188
<211> LENGTH: 15
<212> TYPE: PRT
<213> ORGANISM: Artificial Sequence
<220> FEATURE:
<223> OTHER INFORMATION: Description of Artificial Sequence; note = synthetic construct

<400> SEQUENCE: 188

```
Gln Phe Trp Cys Leu Trp Phe Cys Tyr Asp Lys Cys Phe Trp Asn
1               5                   10                  15
```

```
<210> SEQ ID NO 189
<211> LENGTH: 132
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 189
```

```
Arg Tyr Thr Gln Ser Asn Gly Arg Arg Pro Phe Gly Ile Ser Ala Leu
1               5                   10                  15

Ile Val Gly Phe Asp Phe Asp Gly Thr Pro Arg Leu Tyr Gln Thr Asp
                20                  25                  30

Pro Ser Gly Thr Tyr His Ala Trp Lys Ala Asn Ala Ile Gly Arg Gly
            35                  40                  45

Ala Lys Ser Val Arg Glu Phe Leu Glu Lys Asn Tyr Thr Asp Glu Ala
        50                  55                  60

Ile Glu Thr Asp Asp Leu Thr Ile Lys Leu Val Ile Lys Ala Leu Leu
65                  70                  75                  80

Glu Val Val Gln Ser Gly Gly Lys Asn Ile Glu Leu Ala Val Met Arg
                85                  90                  95

Arg Asp Gln Ser Leu Lys Ile Leu Asn Pro Glu Glu Ile Glu Lys Tyr
            100                 105                 110

Val Ala Glu Ile Glu Lys Glu Lys Glu Asn Glu Lys Lys Lys Gln
        115                 120                 125

Lys Lys Ala Ser
    130
```

```
<210> SEQ ID NO 190
<211> LENGTH: 52
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 190
```

```
Lys Tyr Gly Pro Ser His Thr Pro Ser Arg Ser Ser Arg Arg Ser Cys
1               5                   10                  15

Ala Cys Gln Ser Ser Pro Cys Ser Leu Ala Pro Gln Trp Phe Leu Ser
                20                  25                  30

Phe Ala Arg Met Glu Met Thr Asp Ser Asn Gly Pro Lys Leu Val Pro
            35                  40                  45

Thr Ser Ser Thr
    50
```

```
<210> SEQ ID NO 191
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 191
```

```
Arg Pro Gly Pro Gly Pro
1               5
```

```
<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 192

Val Ser Glu Leu Ala Cys Ile Tyr Ser Ala Ser Phe Cys Thr Thr Met
1               5                   10                  15

Arg

<210> SEQ ID NO 193
<211> LENGTH: 34
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 193

Val Gln Ala Asn Thr His Ser Gln Cys His Gln Thr Ala Met Phe Leu
1               5                   10                  15

His Ala Leu Arg Thr Gly Leu Ala Thr Arg Gly Asn Ala Thr Leu Phe
            20                  25                  30

Leu Leu

<210> SEQ ID NO 194
<211> LENGTH: 32
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 194

Ser Pro Arg Ser Trp Ala Gly Pro Val Leu Arg Asp Ser Ala Arg Arg
1               5                   10                  15

Cys Ala Trp Asn Ser Trp Thr Thr Arg Ala Asp Pro Ser Ser Ala Met
            20                  25                  30

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 195

Ala Thr Ser Thr Leu Gly Ala Ser Ser Ala Met
1               5                   10

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 196

Val Leu Ala Ser Leu Pro Val Tyr Leu Leu Val Gly Leu
1               5                   10
```

```
<210> SEQ ID NO 197
<211> LENGTH: 13
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 197

Val Leu Ala Leu Val Val Ser Val Gln Thr Gly Thr Val
1               5                   10

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 198

Val Ser Asp Gly Val Ile Lys Gly Val Gln Arg His Glu Gly Ala
1               5                   10                  15

<210> SEQ ID NO 199
<211> LENGTH: 25
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 199

Val His Gln Gly Pro Cys Trp Pro Pro Trp Ser Pro Trp Pro Ser Trp
1               5                   10                  15

Thr Ser Arg Cys Lys Arg Trp Trp Leu
            20                  25

<210> SEQ ID NO 200
<211> LENGTH: 22
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 200

Trp Ala Ala Ser Pro Leu Ser Cys Leu Gln Thr Arg Ser Gln Arg Gln
1               5                   10                  15

Gln Lys Ile Phe Val Leu
            20

<210> SEQ ID NO 201
<211> LENGTH: 13
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 201

Leu Gly Ala Ser Ser Leu Val Met Pro Gly Thr Leu Leu
1               5                   10

<210> SEQ ID NO 202
```

```
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 202

Trp Thr Phe Leu Val Ile Pro Thr Trp
1               5

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 203

Cys Gly Leu Gln Val Val Asp Pro Ile Phe His
1               5                   10

<210> SEQ ID NO 204
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 204

Leu Gln Val Asp Val Gly Ile Tyr Leu Cys Trp Cys Leu Val
1               5                   10

<210> SEQ ID NO 205
<211> LENGTH: 16
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 205

Val Leu Val Ser Ser Pro Ser Pro Thr Gln Ser Met Leu Gln Leu Pro
1               5                   10                  15

<210> SEQ ID NO 206
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 206

Met Leu Arg Leu Met Met Asp Met Met Met Met
1               5                   10

<210> SEQ ID NO 207
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 207
```

```
Leu Gln Val Asp Val Gly Ile Tyr Leu Cys Trp Cys Leu Val
 1               5                  10
```

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 208

```
Leu Val Ser Ser Pro Ser Pro Thr Gln Ser Met Leu Gln Leu Pro
 1               5                  10                  15
```

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 209

```
Leu Glu Val Val Ala Arg Phe His Arg Lys Lys
 1               5                  10
```

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 210

```
Trp Leu Met Ser Ser Arg Ser Glu Trp Val Asn
 1               5                  10
```

<210> SEQ ID NO 211
<211> LENGTH: 24
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 211

```
Val Ile Gln Arg Pro Ala Ala Thr Leu Arg Thr Thr Trp Ala Leu Ser
 1               5                  10                  15

His Trp Leu Met Thr Val Lys Cys
                20
```

<210> SEQ ID NO 212
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 212

```
Val Asp Glu Asn Trp Glu Gly Ser Leu Lys Ser Lys Leu Cys
 1               5                  10
```

<210> SEQ ID NO 213
<211> LENGTH: 13

```
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 213

Cys Glu Tyr Ser Thr Pro Thr Ser Met Gly Gly Gly Lys
1               5                   10

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 214

Ser Leu Gln Ser Trp Tyr Leu Arg Leu
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 215

Lys Ser Leu Gln Ser Trp Tyr Leu Arg
1               5

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 216

Phe Leu Ser Pro Met Ser Gly Leu
1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 217

Gln Ser Ala Cys Thr Gly Ile His Arg
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 218

Gly Val Val Arg Pro Ile Leu Asp Val
```

-continued

```
1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 219

Val Val Arg Pro Ile Leu Asp Val Gly
1               5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 220

Gly Pro Gly Val Val Arg Pro Ile Leu
1               5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 221

Val Arg Pro Ile Leu Asp Val Gly Lys
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 222

Arg Pro Ile Leu Asp Val Gly Lys Ile
1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 223

Lys Leu Ala Ala Glu Gly Leu Ala Pro
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence; note =
```

-continued

```
      synthetic construct

<400> SEQUENCE: 224

Gly Thr Lys Leu Ala Ala Glu Gly Leu
 1               5
```